(12) United States Patent
Ahrens et al.

(10) Patent No.: US 8,053,639 B2
(45) Date of Patent: Nov. 8, 2011

(54) HYDROXYPROLINE-RICH GLYCOPROTEIN PROMOTER

(75) Inventors: Jeffrey Ahrens, Manchester, MO (US); Robert Bensen, Niantic, CT (US); Paolo Castiglioni, Westerly, RI (US); Erin Bell, Ladue, MO (US); Paul Loida, Kirkwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 474 days.

(21) Appl. No.: 12/144,509

(22) Filed: Jun. 23, 2008

(65) Prior Publication Data

US 2009/0083886 A1   Mar. 26, 2009

Related U.S. Application Data

(63) Continuation of application No. 10/839,092, filed on May 5, 2004, now Pat. No. 7,410,800.

(60) Provisional application No. 60/467,910, filed on May 5, 2003, provisional application No. 60/487,273, filed on Jul. 15, 2003.

(51) Int. Cl.
*A01H 1/00* (2006.01)
*C12N 5/14* (2006.01)
*C07H 21/04* (2006.01)

(52) U.S. Cl. ............... 800/295; 435/419; 435/320.1; 536/24.1

(58) Field of Classification Search ............ None
See application file for complete search history.

(56) References Cited

U.S. PATENT DOCUMENTS

| | | | | |
|---|---|---|---|---|
| 5,990,387 | A | * 11/1999 | Tomes et al. ............ | 800/293 |
| 2002/0123118 | A1 | 9/2002 | Allen et al. ............ | 435/190 |
| 2002/0188964 | A1* | 12/2002 | Grotewold ............ | 800/282 |
| 2004/0034888 | A1 | 2/2004 | Liu et al. ............ | 536/23.1 |
| 2007/0011783 | A1 | 1/2007 | Liu et al. ............ | 800/278 |

FOREIGN PATENT DOCUMENTS

| WO | WO 96/29857 | 3/1996 |
|---|---|---|
| WO | WO 98/30702 | 7/1998 |
| WO | WO 2004/101741 | 5/2004 |

OTHER PUBLICATIONS

Tagu et al. (Plant Molecular Biology, 20:529-538, 1992).*
Stiefel et al. (GenBank Sequence Accession No. AJ131535, Published Dec. 11, 1998).*
Kim et al., (Plant Mol. Biol. 24:105-117, 1994).*
Donald et al. (EMBO J. 9:1717-1726, 1990).*
Benfey et al., (Science 250:959-966, 1990).*
Appendix A (Claims in U.S. Appl. No. 10/839,092 as allowed in Notice of Allowance mailed Mar. 20, 2007). Petition for Withdrawal from Issue under 37 CFR § 1.313(a) for U.S. Appl. No. 10/839,092, filed May 15, 2007.
Appendix B (Claims pending in U.S. Appl. No. 11/520,715) Petition for Withdrawal from issue under 37 CFR § 1.313(a) for U.S. Appl. No. 10/839,092, filed May 15, 2007.
Appendix C (nucleic acid alignment between SEQ ID No. 19 of U.S. Appl. No. 10/839,092 and SEQ ID No. 25824 of U.S. Appl. No. 11/520,715). Petition for Withdrawal from Issue under 37 CFR § 1.313(a) for U.S. Appl. No. 10/839,092, filed May 15, 2007.
Appendix D (amino acid alignment between SEQ ID No. 1 of U.S. Appl. No. 10/839,092 and SEQ ID No. 52139 of U.S. Appl. No. 11/520,715). Petition for Withdrawal from Issue under 37 CFR § 1.313(a) for U.S. Appl. No. 10/839,092, filed May 15, 2007.
EPO Communication EP04751446.8-2406 (PCT/US/2004/014054) European Search Report, dated Aug. 29, 2007.
EPO Communication EP04751446.8-2406 (PCT/US/2004/014054) Supplementary European Search Report, dated Jan. 30, 2008.
GenBank Accession No. AAP54879, Jul. 12, 2006.
Keskin et al., "A new, structurally nonredundant, diverse data set of protein-protein interfaces and its implications," *Protein Science*, 13:1043-1055, 2004.
Nuccio et al., "The endogenous choline supply limits glycine betaine synthesis in transgenic tobacco expressing choline monooxygenase," *Plant J.*, 16:487-496, 1998.
Thornton et al., "From structure to function: approaches and limitations," *Nature Structural Biology, Structural Genomics Supplement*, 7:(11):991-994, Nov. 2000.
Office Action regarding U.S. Appl. No. 10/839,092, dated Aug. 18, 2005.
Response to Office Action regarding U.S. Appl. No. 10/839,092, dated Sep. 16, 2005.
Office Action regarding U.S. Appl. No. 10/839,092, dated Nov. 7, 2005.
Request for Interview with Supervisory Examiner regarding U.S. Appl. No. 10/839,092, dated Feb. 22, 2006.
Interview Summary regarding U.S. Appl. No. 10/839,092, dated Mar. 31, 2006.
Response to Office Action and Amendment regarding U.S. Appl. No. 10/839,092, dated May 2, 2006.
Office Action regarding U.S. Appl. No. 10/839,092, dated Jun. 14, 2006.
Notice of Appeal from the Examiner to the Board of Patent Appeals and Interferences regarding U.S. Appl. No. 10/839,092, dated Sep. 14, 2006.
Amendment After Appeal Under 37 CFR §41.33 regarding U.S. Appl. No. 10/839,092, dated Nov. 10, 2006.
Office Communication—Advisory Action Before the Filing of an Appeal Brief regarding U.S. Appl. No. 10/839,092, dated Nov. 30, 2006.
Appellants' Brief regarding U.S. Appl. No. 10/839,092, dated Dec. 14, 2006.

(Continued)

*Primary Examiner* — Vinod Kumar
(74) *Attorney, Agent, or Firm* — SNR Denton US LLP; Erin C. Robert, Esq.

(57) ABSTRACT

The present invention provides transgenic plants transformed with novel DNA constructs comprising promoter sequences useful for driving the expression of heterologous DNA sequences. Such promoter sequences include promoters hydroxyproline-rich glycoprotein promoters. Also included in the invention are plant cells and seeds produced by the transgenic plants that comprise the novel DNA sequences.

6 Claims, 5 Drawing Sheets

OTHER PUBLICATIONS

Petition for Withdrawal from Issue Under 37 CFR § 1.313(a) regarding U.S. Appl. No. 10/839,092, dated May 15, 2007.
Decision on Petition regarding U.S. Appl. No. 10/839,092, dated May 16, 2007.
Office Action regarding U.S. Appl. No. 10/839,092, dated Jul. 11, 2007.
Response to Non-Final Office Action regarding U.S. Appl. No. 10/839,092, dated Jan. 11, 2008.
Notice of Allowance regarding U.S. Appl. No. 10/839,092, dated Mar. 20, 2008.

* cited by examiner

Figure 1

```
Maize GB1      MIPYATAAEAEGALGRTMTWAETAWYEYSAVMPDSWLHCHTTFILFVIYS
Maize GB1-2    MMPYGTAAEAEAALGRSMTWAEALWFRYSAGMPDLCLTWHVSLVYLVLYA
Rice GB1-1     MLPYATAAEAEAAVGRGLTWAEAAWFRYSAAIPDYCLYCHNVPILLLVYT
Barley GB1-1   MLPYATTGDAEAALGRALTWAEAAWLRYSASVPDRYLHWPNIAITLVVYT
Consensus      MXPYXTXXXAEXAXGRXXTWAEXXWXXYSAXXPDXXL Maize GB1      IAPLPLLLLEQFAPSVVLPYKLQPRVRLPP--AASLSCYMDAACIFPLAV
Maize GB1-2    LVPLPVMVIQKLAPGYALRHKLQPGVPEPSPVSTYVEYIRDSRGVTLAAL
Rice GB1       LAPLPLALLELRR-HLPLPHKLQPGVRHPP--AAFLRCYAATARVLLLAV
Barley GB1     LAPLPLALFDLAAPAVAAPYKLQPKVQHPP--ATFFRCYMDAVRVSLLII Maize GB1      GLQFVSYPAVAKILRTRMGLPLPSVRETIAQLVVYSLVEDYLSYWMHRLL
Maize GB1-2    GPFPLIYSIAFKLFGVRTGLPLPSVWETATHLAVYSLVEDYTSYWLHRFL
Rice GB1       GPVQLASFPAVRAVGIRTGLPLPSAGETAAQVAVYLLVEDYLGYWIHRLL
Barley GB1     GPYQLISYPAAKIMDIRTGLPLPSMGEIAAQLTVYFLVEDYLNYWLHRLL Maize GB1      HTQWCYEKIHRVHHEFTAPTGFAMSYSHWAENVVLSIPALAGPVLVPCHV
Maize GB1-2    HTRWGYEKIHRVHHEKTAPSGFAAAYATGTELSLYLTTLFLGPAIVPSHV
Rice GB1       HTPWAYHHIHRVHHEFTAPMGYAAPYAHWAEILILGFPAFAGPAIVPCHM
Barley GB1     HTKWCYEKIHHVHHEFTAPMAYAAWYGHWAEMLILAXPSLAGPALVPCHV Maize GB1      TTQWLWFSIRLIEGINTHSGYHFPFSPCRLIPFYGGAAYHDYHHYAGGRS
Maize GB1-2    TTHWLLFSIRIMEAFDTHSGYHFPFSLARFIPFYGGAEFHDYHHYAGEKT
Rice GB1       TTFWLWFVLRHLEAIHIHSGFKLPFDPTKYIPLYGGVEYHDYHHFVGGHS
Barley GB1     TTLWIWFAARLVESLNIHSGFKLPFNAEKYIPFYGGAEHHDYHHYIGGQS Maize GB1      DYQSNFAPLFTYCLYRTDKGYRYHKLKQEKLKSLAENSADKGGNYSFDEG
Maize GB1-2    RSNFSSVFTYCDYIYGTNKGYMYHKRSLAELKTKEAEHSGKED-------
Rice GB1       QSNFSSVFTFCDYIYGTDRGYRYHKASLSKMRIFVRA-------------
Barley GB1     KSNFAPVFTYCDYIYGTDKGYRYHKATLAKLKELAGNEVQKGVDNGFNSG Maize GB1      KKNRYFCA
Maize GB1-2    --------
Rice GB1       --------
Barley GB1     KQE-----
```

Figure 2 (sheet 1)

```
     Maize GB1    MIPYATAAEAEGALGRTMTWAETAWYEYSAVMPDSWLHCHTTFIL
    Maize GB1-2   MMPYGTAAEAEAALGRSMTWAEALWFRYSAGMPDLCLTWHVSLVY
     Rice GB1-1   MLPYATAAEAEAAVGRGLTWAEAAWFRYSAAIPDYCLYCHNVPIL
    Barley GB1-1  MLPYATTGDAEAALGRALTWAEAAWLRYSASVPDRYLHWPNIAIT
    Maize GB1-3-1 MLPYATAAEAEAALGRPMTPAEALWFRYTAGVSDYHLYCCNILFL
     Leek GB1-3-1 MIPYPSLTAAEAALNRPLTYAETIWFNYSATIPDPLLYYHNTIFL
       At GB1-3-1 MIPYATVEEASIALGRNLTRLETLWFDYSATKSDYYLYCHNILFL
       At GB1-3-2 MIPYATIEEASIALSRNLTWLETLWFDYSATKSDYYLYCHNILFL
       At GB1-3-3 MIPYPTVEDASVALGRNLTWFETVWFDYSATKSNFHVYCHTILVL
       At GB1-3-4 MIPYATIEEASIALSRNLTWLETLWFDYSATKSDYYLYCHNILFL
       Bn GB1-3-1 MIPYATIEEASLALGRNLTTLETLWFDYSATKSDYYLYCHNILFL
      soy GB1-3-1 MLPYASIPEAVAALGRNLTFAETLWFNYSAAKSDYFLYCHNILFL
      soy GB1-3-2 MLPYHTLEGAQVALGRGLTLAETIWFKYSANKPDFVLHCHNTLFL
   barley GB1-3-1 MLPWATAAEAEAALGRPMTPAEALWFRWTAGTPDYGLYCLNILFL
     rice GB1-3-1 MLPYATAAEAEAALGRAMTAAESLWFRYSAGIPDYVLFWHNILFL
    wheat GB1-3-1 MLPWATAAEAEAALERAMTAAEALWFRWTAEASDYYLYCLNILFL
    Consensus     MXPXXXXXXAXXAXXRXXTXXEXXWXXXXA Maize GB1    FVIYSIAPLPLLLLEQFAP--SVVLPYKLQPRVR--LPPAASLSC
    Maize GB1-2   LVLYALVPLPVMVIQKLAP--GYALRHKLQPGVPEPSPVSTYVEY
     Rice GB1     LLVYTLAPLPLALLELRR---HLPLPHKLQPGVR--HPPAAFLRC
    Barley GB1    LVVYTLAPLPLALFDLAAP--AVAAPYKLQPKVQ--HPPATFFRC
    Maize GB1-3-1 FVVFTVAPLPIALLELRAP--AAVSPYKLQPRVR--LSRAEFVRC
     Leek GB1-3-1 FVIFTLVPLPLALLELYWP--SVLKPFKIQPKVY--LSKSEFLEC
       At GB1-3-1 FLVFSLVPLPLVFVELARSASGLFNRYKIQPKVN--YSLSDMFKC
       At GB1-3-2 FLIFSLVPLPLVFIESSQSTSDLFNRYKIQPKVK--NSFSSMFKC
       At GB1-3-3 FLVFSLAPFPLVIVEWT----GWFDQFKIQKKVK--YSLSDMFQC
       At GB1-3-4 FLIFSLVPLPLVLIESAQSTSDLFNRYKIQPKVK--NSFSSMLKC
       Bn GB1-3-1 FLIFSLVPLPLVFVELARSASGWFDRYKIQPKVK--NSFSDMFRC
      soy GB1-3-1 FLVFSLVPLPLVFLEFKR--FSFVSSHKIQPKVR--LSLAETFKC
      soy GB1-3-2 CLFYSIAPIPFVLMELSG--YEKLNKHKIQPSVK--RSFKEMFKC
   barley GB1-3-1 LLVFTLAPLPVALLELRAP--RAVGPYKLQPRVR--LSRADFLKC
     rice GB1-3-1 FVVFTLAPLPVALLELRAP--AAVGPFKLQPKVR--LSREEFFRC
    wheat GB1-3-1 LVVFTLAPLPVALLELRAP--RAVGPYKLQPRVR--LSRAEFIKC Maize GB1    YMDAACIFPLAVGLQFVSYPAVAK----------ILRTRMGLPLP
    Maize GB1-2   IRDSRGVTLAALGPFPLIYSIAFK----------LFGVRTGLPLP
     Rice GB1     YAATARVLLLAVGPVQLASFPAVR----------AVGIRTGLPLP
    Barley GB1    YMDAVRVSLLIIGPYQLISYPAAK----------IMDIRTGLPLP
    Maize GB1-3-1 YKDVLRIFFLVIGPLQLVSYPAVK----------FVGIHTKLPLP
     Leek GB1-3-1 YKNVIKVFFLVVCPLQLLSYPTVK----------FVGIRTGLPLP
       At GB1-3-1 YKDVMTMFILVVGPLQLVSYPSIQ----------MIEIRSGLPLP
       At GB1-3-2 YKDVMKMFILVVGPLQLVSYPSIQVDFVFRVLKQMIEIRSGLPLP
       At GB1-3-3 YKEVMKLFLLVVGTLQIVSYPSIQ----------MVGIRSGLPLP
       At GB1-3-4 YKDVMKMFILVVGPLQLVSYPSIQ----------MIEIRSGLPLP
       Bn GB1-3-1 YRDVMKMFILVVGPLQLVSYPSIQ----------MIEIRSGLPLP
      soy GB1-3-1 YKDVMRMFFLVVGPLQLISYPSIQ----------MIGIRTGLPLP
      soy GB1-3-2 YKDVMETFVIAVSPLQIISYPTIK----------WIGIRTGLSLP
   barley GB1-3-1 YGDVMRIFFLVIGPLQLVSYPAVK----------MVGIHTGLPLP
     rice GB1-3-1 YRDVMRLFFLVIGPLQLVSYPTVK----------MVGIHTGLPLP
    wheat GB1-3-1 YGDVMRIFFLVIGPLQLVSYPAVK----------MVGIHTGLPLP
```

Figure 2 (sheet 2)

```
     Maize GB1    SVRETIAQLVVYSLVEDYLSYWMHRLLHTQWCYEKIHRVHHEFTA
   Maize GB1-2    SVWETATHLAVYSLVEDYTSYWLHRFLHTRWGYEKIHRVHHEKTA
      Rice GB1    SAGETAAQVAVYLLVEDYLGYWIHRLLHTPWAYHHIHRVHHEFTA
    Barley GB1    SMGEIAAQLTVYFLVEDYLNYWLHRLLHTKWCYEKIHHVHHEFTA
   Maize GB1-3-1  SLAELAAQLLVYFLVEDYLNYWIHRFLHGEWGYQNIHRVHHEFTA
    Leek GB1-3-1  SVWEVASQLAVYFLLEDFGNYWIHRWLHGKWGYEKIHKVHHEYTA
      At GB1-3-1  TITEMLSQLVVYFLIEDYTNYWVHRFFHSKWGYDKIHRVHHEYTA
      At GB1-3-2  SCMEIVAQLVVYFLVEDYTNYWVHRFFHCKWGYEKFHHIHHEYTA
      At GB1-3-3  SLMEIVAQLVVYFLIEDYTNYWIHRWMHCKWGYEKIHRIHHEYTS
      At GB1-3-4  SCMEIVAQFVVYFLVEDYTNYWVHRFFHCKWGYEKFHHIHHEYTA
      Bn GB1-3-1  SFGEIAAQLVVYFLVEDYTNYWVHRFFHSKWGYEKIHHIHHEYTA
     soy GB1-3-1  SWREILSQLLVYFLVEDYTNYWIHRFLHNDWGYEKIHRVHHEYHA
     soy GB1-3-2  SGWELFWQLFIYFVIEDFSNYWIHRMLHCKWAFEKIHKVHHEYVA
  barleyGB1-3-1   SLGEMAAQLVVYFLVEDYLNYWIHRLLHGEWGYEKIHRIHHEYTA
    rice GB1-3-1  SLGEMAAQLLVYFLVEDYLNYWIHRLLHGEWGYEKIHRVHHEFTA
   wheat GB1-3-1  SLGEMAAQLLVYFLVEDYLNYWIHRLLHGEWGYEKIHRIHHEYTA Maize GB1    PTGFAMSYSHWAENVVLSIPALAGPVLVPCHVTTQWLWFSIRLIE
   Maize GB1-2    PSGFAAAYATGTELSLYLTTLFLGPAIVPSHVTTHWLLFSIRIME
      Rice GB1    PMGYAAPYAHWAEILILGFPAFAGPAIVPCHMTTFWLWFVLRHLE
    Barley GB1    PMAYAAWYGHWAEMLILAXPSLAGPALVPCHVTTWIWFAARLVE
   Maize GB1-3-1  PIGFAAPYAHWAEVLILGIPSFVGPAIVPGHMITFWLWIILRQVE
    Leek GB1-3-1  PIGFAAPYAHWAEVLILGIPSFLGPAIVPGHMITLWLWIALRQIE
      At GB1-3-1  PIGYAAPYAHWAEVLLLGIPTFMGPAIAPGHMITFWLWIALRQME
      At GB1-3-2  PIGYAAPYAHWAEVLLLGIPTFLGPAIAPGHMITFWLWIALRQIE
      At GB1-3-3  PIGYASPYAHWAEILILGIPTFLGPAIAPGHIMTFWLWISLRQFE
      At GB1-3-4  PIGYAAPYAHWAEVLLLGIPTFLGPAIAPGHMITFWLWIALRQIE
      Bn GB1-3-1  PIGYAAPYAHWAEVLLLGVPTFLGPAIAPGHMITFWLWIALRQIE
     soy GB1-3-1  PIGFAAPYAHWAEILILGIPSFLGPAMVPGHIITFWLWIALRQIE
     soy GB1-3-2  PIGLSAPYAHWAEIIILGIPXFLGPALVPGHITTYWLWFILRQLE
  barleyGB1-3-1   PIGFAAPYAHWAEVLILGIPSFAGPAIAPGHMITFWLWIILRQME
    rice GB1-3-1  PIGFAAPYAHWAEVLILGIPSFVGPALAPGHMITFWLWIVLRQME
   wheat GB1-3-1  PIGFAAPYAHWAEVLILGIPSFAGPAIAPGHMITFWLWIILRQME Maize GB1    GINTHSGYHFPFSPCRLIPFYGGAAYHDYHHYAGGRSQSNFAPLF
   Maize GB1-2    AFDTHSGYHFPFSLARFIPFYGGAEFHDYHHYAGEKTRSNFSSVF
      Rice GB1    AIHIHSGFKLPFDPTKYIPLYGGVEYHDYHHFVGGHSQSNFSSVF
    Barley GB1    SLNIHSGFKLPFNAEKYIPFYGGAEHHDYHHYIGGQSKSNFAPVF
   Maize GB1-3-1  AIETHSGFDFPFTPTKYIPFYGGAEYHDYHHYVGGQSQSNFASVF
    Leek GB1-3-1  ALDTHSGYDFPLSFTKFIPFYGGAEYHDYHHYVGGQSQSNFASVF
      At GB1-3-1  AIETHSGYDFPWSPTKYIPFYGGAEYHDYHHYVGGQSQSNFASVF
      At GB1-3-2  AIETHSGYDFPWSLTKYIPFYGGAEYHDYHHYVGGQSQSNFASVF
      At GB1-3-3  AIETHSGYDFPWSVTKLIPFYGGPEYHDYHHYVGGQSQSNFASVF
      At GB1-3-4  AIETHSGYDFPWSLTKYIPFYGGAEYHDYHHYVGGQSQSNFASVF
      Bn GB1-3-1  AIETHSGYDFPWTLTKFIPFYGGAEYHDYHHYVGGQSQSNFASVF
     soy GB1-3-1  AIDTHSGYDFPRSITKYIPFYGGAEYHDYHHYVGRQSQSNFASVF
     soy GB1-3-2  AIETHSGYDFSWEXTKYIPFYGGPAYHDYHHYVGGKSQSNFAS--
  barleyGB1-3-1   AIDTHSGFDFPFSLTKYIPFYGGAESHDYHHYVGGQSQSIFASVF
    rice GB1-3-1  AIETHSGFDFPFNLTKYIPFYGGAEYHDYHHYVGRQSQSNFASVF
   wheat GB1-3-1  AIDTHSGFDFPFSLTKYIPFYGGAEYHDYHHYVGGQSQSNFASVF
```

Figure 2 (sheet 3)

```
      Maize GB1    TYCDYLYRTDKGYRYHKLKQEKLKSLAENSADKGGNYSFDEGKKN
    Maize GB1-2    TYCDYIYGTNKGYMYHKRSLAELKTKEAEHSGKED----------
       Rice GB1    TFCDYIYGTDRGYRYHKASLSKMRIFVRA----------------
     Barley GB1    TYCDYIYGTDKGYRYHKATLAKLKELAGNEVQKGVDNGFNSGKQE
  Maize GB1-3-1    TYCDYLYGTDKGYRFHKTYLAKLKDLGHNDGQKGDGSGPSYVKLD
   Leek GB1-3-1    TYCDYVYGTDKGYRYRKACLSMMKEESENQNGVENSFQNQKSD--
     At GB1-3-1    TYCDYIYGTDKGYRFQKKLL-EQIKESS--KKSNKHNGGIKSD--
     At GB1-3-2    TYCDYIYGTDKGYRFQKKLLQQVNKYSIN----------------
     At GB1-3-3    TYCDYIYGTDKGYRIHKKLLHHQIKEEAEEKRVRKHD--------
     At GB1-3-4    TYCDYIYGTDKGYRFQKKLLQQMKEKSKKSNKLVNGGEKFD----
     Bn GB1-3-1    TYCDYIYGTDKGYRFQKKFLQQIKQESKKSN-MQNGGDKLD----
    soy GB1-3-1    TYCDYIYGTDKGYRYQKKILQKLKEELANGVEQNGGLYKTD----
    soy GB1-3-2    ---------------------------------------------
 barleyGB1-3-1    TYCDPLCGTDRGYRFHRASLPMLRALAPPAAKKDAPMGFSSAKGD
   rice GB1-3-1    TYCDYLYGTDKGYRYHKAYQAKMKALGQTEGEKADSNGLSYAKLD
  wheat GB1-3-1    TYCDYLYGTDRGYRFHKAYLAKLKDLAPSDGEKEGADGFAYAKLD Maize GB1    RYFCA
    Maize GB1-2    -----
       Rice GB1    -----
     Barley GB1    -----
  Maize GB1-3-1    -----
   Leek GB1-3-1    -----
     At GB1-3-1    -----
     At GB1-3-2    -----
     At GB1-3-3    -----
     At GB1-3-4    -----
     Bn GB1-3-1    -----
    soy GB1-3-1    -----
    soy GB1-3-2    -----
 barleyGB1-3-1    YVVL-
   rice GB1-3-1    -----
  wheat GB1-3-1    -----
```

HYDROXYPROLINE-RICH GLYCOPROTEIN PROMOTER

REFERENCE TO RELATED APPLICATIONS

This application is a continuation of U.S. application Ser. No. 10/839,092 filed May 5, 2004, now U.S. Pat. No. 7,410,800, which claims benefit under 35 USC §119(e) to U.S. Provisional Patent Application Ser. No. 60/467,910, filed May 5, 2003 and Ser. No. 60/487,273, filed Jul. 15, 2003, each of which are incorporated herein by reference in their entirety.

A sequence listing is contained in the file named "38-15 (52913)C Sequences.ST25.txt" which is 105 kilobytes (measured in MS-Windows 2000) and was created on Apr. 30, 2004 and is located in computer readable form on a 3.5 inch diskette filed herewith and incorporated herein by reference.

BACKGROUND OF THE INVENTION

Disclosed herein are polynucleotide sequences useful for producing transgenic plants with increased glycine-betaine content and methods of using such sequences for producing transgenic plants and seed. Such sequences are useful for producing transgenic plants with increased tolerance to stresses such as water-deficit and cold.

Stress, such as water-deficit, cold, heat, nutrient deficiency and the like, can have many adverse effects on plant performance such as yield reduction, increased susceptibility to disease and pests, reduced plant growth and reproductive failure. Considering the complexity of stress response in land plants, especially during conditions that produce water-deficit or cold, relatively few genes specifically associated with this aspect of physiology have been identified. It would be of benefit to the art to increase the number and variety of genes involved in regulating water use or temperature tolerance in plants, more particularly, in maize plants, and even more particularly in maize plants experiencing water-deficit and/or cold.

Glycine-betaine (N,N,N-trimethylglycine) is an osmoprotectant metabolite. Osmoprotectant metabolites, including betaines, such as glycine-betaine, sugars, sugar-alcohols, and amino acids, such as proline, are known to accumulate in plants under water-deficit and other stressful conditions such as cold conditions. Historically, applications of osmoprotectants to seeds and plants has been shown to have beneficial effects upon stress tolerance. Allard et al. (WO 99/01032) found that application of glycine-betaine to wheat plants increased the freezing tolerance of the plants by several degrees and Mottram (U.S. Pat. No. 5,952,267) disclose the foliar application of glycine-betaine to cotton plants under water-deficit which resulted in an increased number of cotton bolls.

The pathways for the synthesis of glycine-betaine are similar in higher plants and microorganisms. In both kingdoms, a two-step oxidation of choline occurs to produce glycine-betaine via an unstable glycine-betaine aldehyde intermediate. Choline is ubiquitous in higher plants. In spinach, the first step conversion of choline to glycine-betaine aldehyde utilizes a ferredoxin dependent choline monooxygenase. In *E. coli*, a membrane bound choline dehydrogenase performs this step. The second step, conversion of the unstable aldehyde to glycine-betaine, is carried out by glycine-betaine aldehyde dehydrogenase. This enzyme has been found to share strong similarity between plant and bacterial species.

Spinach, sugar beet and some varieties of maize are examples of higher plants in which glycine-betaine is found to accumulate under water-deficit stress. In contrast, many other plants, such as tomato, tobacco, rice and some varieties of maize, do not accumulate significant amounts of glycine-betaine, regardless of growing conditions.

Hanson et al., (U.S. Pat. No. 6,310,271) disclose tobacco transformed with a choline monooxygenase gene which exhibited increased accumulation of glycine-betaine. The transgenic plants also demonstrated increased tolerance to irrigation with saline solution when compared to non-transgenic controls. Bulow et al., (PCT Publication WO 98/26801) disclose the use of an *E. coli* choline dehydrogenase gene to impart increased freezing and choline tolerance in transformed potato plants. Allen et al., (U.S. Application No. 2002/0123118A1) disclose the proposed use of choline oxidase, L-allo-threonine aldolase, phosphoserine phosphatase and sarcosine oxidase genes for altering the levels of glycine metabolism in a transformed cell. Adams et al., (U.S. Pat. No. 6,281,411; incorporated herein by reference in its entirety) disclose naturally occurring metabolites, such as glycine-betaine (Wyn-Jones and Storey, 1982) that are osmotically active and/or provide some direct protective effect during drought and/or desiccation.

We have discovered DNA useful for the production of a transgenic plant with increased glycine-betaine. As used herein "GB1" is the name of a protein and its homologs, e.g., a protein at least 40% identical to GB1, the expression of which results in increased glycine-betaine in plants and "gb1" is the name of the DNA coding sequence and its homologs encoding and used to express the GB1 protein. "GB" is used herein to refer to the glycine-betaine metabolite.

SUMMARY OF THE INVENTION

One aspect of this invention provides novel DNA constructs comprising DNA sequences which express GB1 proteins which, when expressed in a transgenic plant, can increase the glycine-betaine content of a transgenic plant. Certain plants expressing such DNA constructs for enhanced levels of glycine-betaine can exhibit increased tolerance to water-deficit, cold or freezing growing conditions or increased yield. The plants expressing the DNA constructs leading to increased glycine-betaine may be inbred or hybrid, preferably soybean, cotton, canola or maize.

In one aspect, the invention provides transgenic seed and plants having in the genome an exogenous DNA comprising a gb1 coding sequence having the sequence of SEQ ID NO:19 which expresses a GB1 protein having the amino acid sequence of SEQ ID NO:1 where the transgenic plants and seeds accumulate increased glycine-betaine as compared to plants and seed of substantially the same genotype lacking this exogenous DNA. In another aspect of the invention, the transgenic seed and plants accumulating increased glycine-betaine as a result of expressing an exogenous DNA comprising a gb1 coding sequence having the sequence of SEQ ID NO:19 which expresses a GB1 protein of SEQ ID NO:1, exhibit increased tolerance to water-deficit and to cold, and exhibit increased yield under normal growing conditions, water-deficit inducing conditions and cold conditions.

An important aspect of this invention provides transgenic seed and plants having in the genome an exogenous DNA comprising a gb1 coding sequence which expresses a protein having an amino acid sequence comprising at least 25 contiguous amino acids of the consensus amino acid sequence of SEQ ID NO:17 or SEQ ID NO:18. In yet another aspect of the invention such transgenic seed or plants have in the genome an exogenous DNA construct which expresses a GB1 protein having an amino acid sequence which is at least 40% identical SEQ ID NO:1. In another aspect, the invention provides transgenic seed and plants having in the genome an exogenous DNA comprising a gb1 coding sequence which has at least 98% identity to a nucleotide sequence in the group consisting of SEQ ID NOS:19-34, the sequences of which encode proteins having amino acid sequences of SEQ ID NOS:1-16, which result in increased accumulation of glycine-betaine in transgenic plants. The invention also provides transgenic seed and plants wherein the exogenous DNA comprising a gb1 DNA coding sequence is operably linked to a promoter which functions in plants. Operable promoters include constitutive, water-deficit-inducible, cold inducible, native, viral, tissue specific, or other promoters functional in a plant.

Still another aspect of this invention provides plants grown from such transgenic seed. The seed expressing exogenous DNA comprising gb1 coding sequence and GB1 protein leading to increased glycine-betaine may be inbred or hybrid, preferably soybean, cotton, canola or maize. Additionally, the invention provides for transgenic plants grown from the transgenic seed, for example, maize, cotton or soybean plants.

In another aspect, the invention provides for transgenic plants and seed comprising an exogenous DNA comprising a gb1 coding sequence which exhibit increased tolerance to cold temperatures. In one aspect, the transgenic plants and seed of the invention enable farmers to plant seed earlier and/or under cooler than normal temperatures for the seed type lacking the gb1 transgene, i.e., at a shorter relative maturity zone or a more polar latitude, increased germination under cold conditions, increased tolerance of newly germinated seed or young seedlings to cold, and increased tolerance of mature plants to cold allowing for later harvest and/or improved harvest, e.g. increased yield, under cold conditions, e.g., about ° C.-10° C. In another aspect, the invention provides transgenic plants and seed comprising an exogenous DNA comprising a gb1 coding sequence which exhibit increased germination, emergence and/or seedling survival at about 110 growing degree units (GDU) or less.

Additionally, the invention provides for a transgenic organism, e.g. a bacterium or plant, having in its genome an exogenous DNA construct which encodes a GB1 protein or homolog as define herein.

This invention also provides promoters for use in transgenic plants, e.g. a maize gb1 promoter and a *coix* hrgp promoter.

BRIEF DESCRIPTION OF THE DRAWINGS

FIG. 1 is an alignment of proteins of SEQ ID NOS:1-4 and a consensus sequence SEQ ID NO:17.

FIG. 2 is an alignment of proteins of SEQ ID NOS:1-16 and a consensus sequence SEQ ID NO:18.

DETAILED DESCRIPTION OF THE INVENTION

Sequences of the Invention

Figure 3:
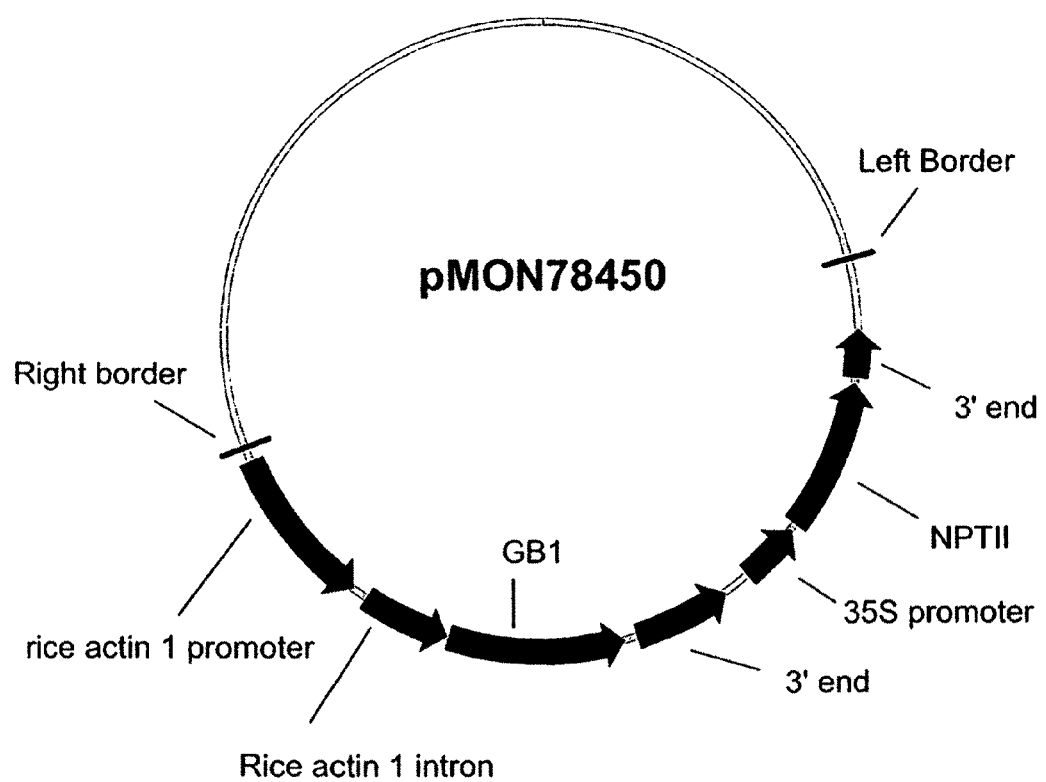
FIG. 3 is a plasmid map of pMON78450, the polynucleotide sequence from right border to left border is found in SEQ ID NO:57.

The following sequences are disclosed in the description of various aspects of this invention:

SEQ ID NO:1 is an amino acid sequence of a maize protein designated as GB1.
SEQ ID NO:2 is an amino acid sequence of a maize protein designated as maize GB1-2 homolog.
SEQ ID NO:3 is an amino acid sequence of a rice protein designated as rice GB1-1 homolog.
SEQ ID NO:4 is an amino acid sequence of a barley protein designated as barley GB1-1 homolog.
SEQ ID NO:5 is an amino acid sequence of a maize protein designated as maize GB1-3-1 homolog.
SEQ ID NO:6 is an amino acid sequence of a leek protein designated as leek GB1-3-1 homolog.
SEQ ID NO:7 is an amino acid sequence of an *Arabidopsis thaliana* protein designated as At GB1-3-1 homolog.
SEQ ID NO:8 is an amino acid sequence of an *Arabidopsis thaliana* protein designated as At GB1-3-2 homolog.
SEQ ID NO:9 is an amino acid sequence of an *Arabidopsis thaliana* protein designated as At GB1-3-3 homolog.
SEQ ID NO:10 is an amino acid sequence of an *Arabidopsis thaliana* protein designated as At GB1-3-4 homolog.
SEQ ID NO:11 is an amino acid sequence of a *Brassica napus* protein designated as Bn GB1-3-1 homolog.
SEQ ID NO:12 is an amino acid sequence of a soybean protein designated as soy GB1-3-1 homolog.
SEQ ID NO:13 is an amino acid sequence of a soybean protein designated as soy GB1-3-2 homolog.
SEQ ID NO:14 is an amino acid sequence of a barley protein designated as barley GB1-3-1 homolog.
SEQ ID NO:15 is an amino acid sequence of a rice protein designated as rice GB1-3-1 homolog.
SEQ ID NO:16 is an amino acid sequence of a wheat protein designated as wheat GB1-3-1 homolog.
SEQ ID NO:17 is a consensus amino acid sequence comprising amino acid residues of SEQ ID NOS:1-4.
SEQ ID NO:18 is a consensus amino acid sequence comprising amino acid residues of SEQ ID NOS:1-16.
SEQ ID NO:19 is a polynucleotide sequence of a maize gb1 coding sequence encoding the protein of SEQ ID NO:1.
SEQ ID NO:20 is a polynucleotide sequence of a maize gb1-2 homolog coding sequence encoding the protein of SEQ ID NO:2.
SEQ ID NO:21 is a polynucleotide sequence of a rice gb1-1 homolog coding sequence encoding the protein of SEQ ID NO:3.
SEQ ID NO:22 is a polynucleotide sequence of a barley gb1-1 homolog coding sequence encoding the protein of SEQ ID NO:4.
SEQ ID NO:23 is a polynucleotide sequence of a maize gb1-3-1 homolog coding sequence encoding the protein of SEQ ID NO:5.
SEQ ID NO:24 is a polynucleotide sequence of a leek gb1-3-1 homolog coding sequence encoding the protein of SEQ ID NO:6.
SEQ ID NO:25 is a polynucleotide sequence of an *Arabidopsis thaliana* gb1-3-1 homolog coding sequence encoding protein of SEQ ID NO:7.
SEQ ID NO:26 is a polynucleotide sequence of an *Arabidopsis thaliana* gb1-3-2 homolog coding sequence encoding the protein of SEQ ID NO:8.
SEQ ID NO:27 is a polynucleotide sequence of an *Arabidopsis thaliana* gb1-3-3 homolog coding sequence encoding the protein of SEQ ID NO:9.
SEQ ID NO:28 is a polynucleotide sequence of an *Arabidopsis thaliana* gb1-3-4 homolog coding sequence encoding the protein of SEQ ID NO:10.
SEQ ID NO:29 is a polynucleotide sequence of a *Brassica napus* gb1-3-1 homolog coding sequence encoding the protein of SEQ ID NO:11.
SEQ ID NO:30 is a polynucleotide sequence of a soybean gb1-3-1 homolog coding sequence encoding the protein of SEQ ID NO:12.
SEQ ID NO:31 is a polynucleotide sequence of a soybean gb1-3-2 homolog coding sequence encoding the protein of SEQ ID NO:13.

SEQ ID NO:32 is a polynucleotide sequence of a barley gb1-3-1 homolog coding sequence encoding the protein of SEQ ID NO:14.

SEQ ID NO:33 is a polynucleotide sequence of a rice gb1-3-1 homolog coding sequence encoding the protein of SEQ ID NO:15.

SEQ ID NO:34 is a polynucleotide sequence of a wheat gb1-3-1 homolog coding sequence encoding the protein of SEQ ID NO:16.

SEQ ID NO:35 is a polynucleotide sequence of a rice actin 1 intron promoter.

SEQ ID NO:36 is a polynucleotide sequence of a maize hsp1 7.5 promoter.

SEQ ID NO:37 is a polynucleotide sequence of a maize hva22 promoter.

SEQ ID NO:38 is a polynucleotide sequence of a maize ca4h promoter.

SEQ ID NO:39 is a polynucleotide sequence of a maize rab-17 promoter.

SEQ ID NO:40 is a polynucleotide sequence of a maize rab-17 promoter.

SEQ ID NO:41 is a polynucleotide sequence of a rice hsp 17.5 promoter.

SEQ ID NO:42 is a polynucleotide sequence of a rice hva22 promoter.

SEQ ID NO:43 is a polynucleotide sequence of a rice ca4h promoter.

SEQ ID NO:44 is a polynucleotide sequence of a rice hsp16.9 promoter.

SEQ ID NO:45 is a polynucleotide sequence of a rice hsp22 promoter.

SEQ ID NO:46 is a polynucleotide sequence of a rice rab-17 promoter.

SEQ ID NO:47 is a polynucleotide sequence of a maize gb1 promoter.

SEQ ID NO:48 is a polynucleotide sequence of a maize cvy-cik1 promoter.

SEQ ID NO:49 is a polynucleotide sequence of a maize cvy-cik1 promoter.

SEQ ID NO:50 is a polynucleotide sequence of a maize cvy-cik1 promoter.

SEQ ID NO:51 is a polynucleotide sequence of a maize cvy-cik1 promoter.

SEQ ID NO:52 is a polynucleotide sequence of a maize cvy-cik1 promoter.

SEQ ID NO:53 is a polynucleotide sequence of a rice cvy-cik1 promoter.

SEQ ID NO:54 is a polynucleotide sequence of a maize rtbv promoter.

SEQ ID NO:55 is a polynucleotide sequence of a maize nas promoter.

SEQ ID NO:56 is a polynucleotide sequence of a *coix* hrgp promoter.

SEQ ID NO:57 is a polynucleotide sequence from the right border to the left border, inclusive, of pMON78450 shown in FIG. 3. Base pairs 1 to 357 are the right border, base pairs 390 to 1232 are the rice actin 1 promoter, base pairs 1310 to 1778 are the rice actin 1 intron, base pairs 1781 to 2698 are the maize GB1 coding sequence of SEQ ID NO:19, base pairs 2767 to 3274 are the 3' untranslated region, base pairs 3409 to 3701 are the 35S promoter, base pairs 3766 to 4560 are the NPTII marker coding sequence, base pairs 4592 to 4844 are the nos 3' untranslated region, and base pairs 4924 to 5365 are the left border.

Traits of the Invention

A plant or seed that shows a desired trait, e.g., increased glycine-betaine, or increased tolerance or increased resistance to water-deficit condition, to cold condition, to freezing condition, or a plant with increased yield, is a plant or seed comprising a particular exogenous DNA which imparts a desired, measurable change in the trait in comparison to a control plant, e.g., a plant or seed of substantially the same genotype that lacks that particular exogenous DNA. Preferably, the enhanced desired trait is measured by comparing the trait in a transgenic plant or seed with the particular exogenous DNA associated with the enhanced desired trait to the trait in a control plant or seed. As used herein, a "control plant" or a "control seed" is a plant or seed of substantially the same genotype as the plant or seed it is being compared to, but lacking a particular exogenous DNA construct. A control plant or control seed can be a natural, non-transgenic wild-type plant preferably of the same species as the transgenic plant comprising the particular exogenous DNA. A control plant or control seed can be a second transgenic plant, preferably of the same species as the transgenic plant comprising the particular exogenous DNA, but lacking that same particular exogenous DNA. Preferably, the control plant or control seed lacking the exogenous DNA is a sibling of the plant or seed comprising the particular exogenous DNA, e.g. a negative segregant. Such a sibling control plant or control seed may comprise other exogenous DNA.

This invention provides for a transgenic maize plant exhibiting increased glycine-betaine content. The transgenic maize plant comprises an exogenous DNA comprising a gb1 coding sequence (SEQ ID NOS:19-34) expressing a GB1 protein (SEQ ID NOS:1-16) which exhibits at least about a 2-fold, about a 5-fold, about a 10-fold, about a 20-fold, about a 50-fold or even about a 70-fold or greater increase in glycine-betaine content as compared to a non-transgenic maize plant. Increased tolerance or resistance to water-deficit or cold or freezing may be exhibited by the plant accumulating at least a 2-fold increase in glycine-betaine and may be measured in a variety of ways including increased plant height, leaf length, leaf extension rate, number of leaves, root length, root mass, shoot mass, seed set, number of seed, yield, photosynthesis, turgor pressure, osmotic potential, amount of pollen, silking, germination, chlorophyll fluorescence, necrosis, and the like.

As used herein "stress response" is a plant or seed condition occurring in response to external influences capable of affecting the physical or biochemical characteristics of a plant or seed. These external influences are "stress." Stresses include, but are not limited to, all biotic and abiotic stresses that could influence a plant or seed, from infection to environment. For example, cold, heat, water-deficit, salinity, chemicals, weather conditions, fungal or bacterial infection, insect infestation, soil nutrient deficiencies or excesses, soil compaction or density, light, shade, or soil pH, or any combination of these conditions, are types of stresses a plant or seed may experience and respond to. Those physical or biochemical characteristics of a plant or seed that may be influenced by stress include, for example, yield, height, color, vigor, root growth, shoot growth, flowering times and qualities, seed quality, pollen quality, reproductive potential, germination or development, or any combination of these or other plant characteristics.

As used herein "water-deficit" is a plant condition characterized by water potential in a plant tissue of less than about −0.5 megapascals (MPa), e.g. −0.6 MPa. Water potential in maize is conveniently measured by clamping a leaf segment in a pressurizable container so that a cut cross section of leaf is open to atmospheric pressure. Gauge pressure (above atmospheric pressure) on the contained leaf section is increased until water begins to exude from the atmospheric-pressure-exposed cross section; the gauge pressure at incipient water exudation is reported as negative water potential in the plant tissue, e.g. 0.5 MPa gauge pressure is reported as =0.5 MPa water potential. A water-deficit may be induced in plant or seed by a number of manners, including growing in a geographical location in which rainfall is usually limiting, or growing in a growth chamber or greenhouse where water is provided or withheld in a monitored manner. In addition, water-deficit condition may be brought about in a plant or seed by exposure to solutions that may cause or mimic water-deficit such as saline solutions, PEG solutions and the like. A transgenic seed or plant is said to have improved water-deficit tolerance if it is able to germinate, germinate more quickly, grow, mature, and/or reproduce under water-deficit conditions as compared to a seed or plant of substantially the same genotype but lacking that exogenous DNA construct. A seed or plant with improved water-deficit tolerance would enable farmers to plant and grow crops in less than ideal water conditions, for example, in a drier location or in a location exposed with higher saline levels than normal in the soil and/or water used for irrigation, thus expanding the locations or conditions in which the plant or seed may be grown.

As used herein "non-water-deficit" conditions describe plant conditions characterized by water potential in a plant tissue of greater than about −0.5 megapascals (MPa), e.g. −0.4 MPa and may be measured as previously described. Non-water-deficit conditions may be induced in a plant by a number of manners, including growing plants in a geographical location in which rainfall is usually not limiting, growing plants in a geographical location in which rainfall is usually limiting and providing water by irrigation methods, or growing in a growth chamber or greenhouse where water is provided in a monitored manner.

As used herein "increased yield" identifies a measurable increase in the amount of useable product from a first plant, e.g., a plant comprising a particular exogenous DNA, compared to a second plant, e.g. a non-transgenic control plant or other control plant lacking a particular exogenous DNA, when the plants are grown under substantially identical conditions. Yield is based upon the weight of the grain produced from all the plants of a given line grown in a given plot and is measured in bushels per acre. Yield is typically measured in field trials using methods known to those of skill in the art.

As used herein, "cold tolerance" is defined as the ability of a seed, seedling, young plant, or mature plant, or parts thereof, to germinate and/or continue growth for a significant period of time after being placed at or exposed to a temperature below that normally encountered by a plant of that species at that growth stage. This invention provides a transgenic maize plant and seed with increased glycine-betaine comprising an exogenous DNA construct comprising a gb1 coding sequence (SEQ ID NOS:19-34) expressing a GB1 protein (SEQ ID NOS:1-16) that exhibits increased cold tolerance relative to a control plant or control seed.

"Germination" is defined as the beginning of growth or development in a seed, especially after a period of dormancy. Germination is often considered to begin when the seed takes up water (imbibes) and is considered to be essentially complete when the embryonic axis beings to elongate. As used herein, "cold germination" is germination occurring at temperatures below (two or more degrees Celsius below) those normal for a particular species or particular strain of plant. A transgenic seed is said to have improved cold germination if it is able to germinate more quickly in the cold temperature and/or if a greater percentage of the seed germinate in the cold temperature in a given amount of time as compared to a control seed or control plant. The temperature may be about 1° C. colder than normal, about 2° C. colder than normal, about 4° C., 6° C., 8° C. or even about 10° C. or more colder than normal.

A convenient way to measure cold stress conditions is to measure the accumulation of growing degree units (GDU) over time from the planting date. It is well known to one skilled in the art that approximately 120 GDUs are required for commercial maize hybrids to germinate and emerge from the soil. GDUs, which reflect the warming of the air, are measured on a daily basis in a cumulative manner using the following calculation:

$$GDU = \frac{(\text{Daily Max Temp}^* + \text{Daily Min Temp}^{**}) - 50}{2}$$

where * is the daily maximum temperature up to 86° F.;
if the temperature exceeds 86° F. then the value of 86° F. is used
and where ** is the daily minimum temperature down to 50° F.;
if the temp is lower than 50° F. then the value of 50° F. is used.

Under cold conditions, therefore, it takes more days to reach a given number of GDUs and, conversely, under warm conditions it takes fewer days to reach that same number of GDUs. For example, the United States National Weather Service daily high and low normal temperatures for the last 30 years indicate that for Spencer, Iowa, (latitude 42.97, Longitude 90.10, a central location within the US maize growing territories) 20 days are required to accumulate 120 GDUs if planting occurs on April 15$^{th}$ whereas 11 days are required if planting occurs on May 15$^{th}$. Typically, it takes about 12 to about 15 days to accumulate the about 120 to 140 GDU required for maize to germinate in early spring conditions although one skilled in the art would know that this may vary slightly with respect to some variables such as planting depth and date of planting.

If it takes more than about 16, e.g., about 18, or 20 or even about 24 days, to accumulate about 120 to 140 GDUs, then a cold stress is imposed on a plant or seed. A transgenic seed having in its genome an exogenous DNA comprising a gb1 coding sequence, the expression of which results in increased glycine-betaine, will demonstrate improved germination and growth as compared to a control seed or control plant when about 16, or more, e.g. 18, 20 or 24 days are required to accumulate about 120 to 140 GDUs.

A transgenic maize seed having in its genome an exogenous DNA comprising a gb1 coding sequence resulting in increased glycine-betaine shows increased tolerance to cold conditions as compared to control plant or control seed. The transgenic maize seed germinates more quickly, emerges from the soil more rapidly and/or with more kernels germinated, and exhibits better seedling survival, in about 110 GDU, or less, e.g., 100 GDU or 90 GDU, than a control seed or control plant. It is known to one skilled in the art that hot and dry conditions during the reproductive phase damage the female organs and tissues, thereby reducing the harvested yield of commercial maize. The hot and dry conditions typically begin in early July within the US maize growing territories. A transgenic maize seed that emerges from the soil more quickly and/or with more kernels germinated and exhibits better seedling survival, in about 110 GDU or less, will reach reproductive developmental stages earlier in the growing season, thus avoiding damage during hot and dry conditions and thereby enabling farmers to effectively increase the harvested yield of maize in bushel/acre.

A seed or plant may be exposed to cold conditions at many points in time and thus it is desirable to have cold tolerance at many stages of development. For example, for a seed, cold germination is a form of cold tolerance that may be exhibited during germination at temperatures below the normal germination temperature for that seed. Cold tolerance may benefit a newly germinated seed as it may experience cold temperature after the embryonic axis begins to elongate. A young plant may benefit from cold tolerance as it may experience cold temperature as new leaves are developing above the ground. A more mature plant may benefit from cold tolerance as it may experience cold temperature during the periods of fertilization, seed set, grain fill and other reproductive activities. "Freezing tolerance" is defined as the ability of a seed, seedling, young plant, or mature plant, or parts thereof, to continue growth for a significant period of time after being placed at a temperature about freezing (e.g., about 32° F.) or below.

For a crop such as maize, a normal field planting is carried out when the temperature in the top two inches of soil is at least 10-12° C. during the day, therefore a transgenic seed that germinates more quickly and/or to a greater percentage at about 12° C., about 10° C., 8° C., 6° C., 4° C., or about 2° C. or even about 1° C. as compared to a seed or plant of substantially the same genotype but lacking that exogenous DNA construct, is considered to have improved or enhanced cold germination. A transgenic seed of the invention with enhanced cold tolerance, especially improved cold germination, would enable farmers to plant and grow crops at an earlier time in the season, in a cooler location than normal, at both an earlier time in the season and at a cooler location than normal, or allow for a later harvest, thus expanding the times and/or locations in which the plant may be grown as compared to control plants or control seed.

In a field, the cold temperatures may be imposed upon seeds and plants by planting at an earlier time than is normal for a particular location and/or planting at a geographical location that is typically colder than the geographical location in which the seed is normally planted, e.g., a shorter relative maturity (RM) zone. Relative maturity is a universal term of the art describing the time required for a given maize genotype to reach maturity. RM is determined during the development of a maize hybrid line by constantly assessing how many days the genotype takes to reach maturity in different environments. Most commercial hybrids fall into RM zones which range from 85 (in the more Northern areas of the US maize growing territories) to 125 (in the more Southern areas of the US maize growing territories). In other parts of the world growing maize, commercial hybrids typically have RMs of about 75-120 in Europe, about 108-138 in Africa, about 105-135 in Argentina, about 118-140 in Brazil, about 115-138 in Mexico and about 80-145 in Asia. Those skilled in the art know that maize varieties adapted to longer RM zones (100-120 or more) produce greater yield than those at shorter RM zones (85-100 or less); enabling farmers to grow a higher RM variety in a shorter RM zone would effectively increase the harvested yield of maize in bushel/acre worldwide. A transgenic seed or plant comprising an exogenous DNA comprising a gb1 DNA coding sequence of SEQ ID NOS:19-34 expressing proteins of SEQ ID NOS:1-6 exhibiting increased glycine-betaine and increased cold tolerance, would enable farmers to plant and grow crops in a shorter RM zone as compared to control seed or control plants.

Recombinant DNA Constructs

The present invention contemplates the use of polynucleotides which encode a protein effective for imparting increased tolerance to water-deficit or cold in plants, increased glycine-betaine, and/or increased yield. Such polynucleotides are assembled in recombinant DNA constructs using methods known to those of ordinary skill in the art. A useful technology for building DNA constructs and vectors for transformation is the GATEWAY™ cloning technology (available from Invitrogen Life Technologies, Carlsbad, Calif.) which uses the site-specific recombinase LR cloning reaction of the Integrase/att system from bacteriophage lambda for vector construction instead of restriction endonucleases and ligases. The LR cloning reaction is disclosed in U.S. Pat. Nos. 5,888,732 and 6,277,608, U.S. Patent Application Publications 2001283529, 2001282319 and 20020007051, all of which are incorporated herein by reference. The GATEWAY™ Cloning Technology Instruction Manual which is supplied by Invitrogen also provides concise directions for routine cloning of any desired RNA into a vector comprising operable plant expression elements.

As used herein "exogenous DNA" refers to DNA which is not normally found next to the adjacent DNA, i.e., a sequence not normally found in the host genome in an identical context, or any two sequences adjacent to each other which are not normally or naturally adjacent to each other. Exogenous DNA may include a DNA or RNA sequence native to the host genome or may comprise the native sequence altered by the addition or deletion of one or more different regulatory elements or other sequences as discussed below. The exogenous DNA may encode a protein or non-protein product. A DNA construct comprising a coding sequence of interest, which originates or is produced outside of an organism, is also an example of an exogenous DNA.

Exogenous DNA constructs used for transforming plant cells will comprise the coding sequence of interest and usually other elements as discussed below such as, but not limited to introns, 5' and 3' untranslated regions, and enhancers. An exogenous DNA of the present invention is exemplified by a rice actin 1 promoter and intron operably linked to a gb1 coding sequence operably linked to a 3' untranslated region. As used herein "transgene" means an exogenous DNA which has been incorporated into a host genome or is capable of autonomous replication in a host cell and is capable of causing the expression of one or more cellular products. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the exogenous DNA.

As used herein "coding sequence" means a DNA sequence from which an RNA molecule is transcribed. The RNA may be an mRNA which encodes a protein product, an RNA which functions as an anti-sense molecule, or a structural RNA molecule such as a tRNA, rRNA, or snRNA, or other RNA. As used herein "expression" refers to the combination of intracellular processes, including transcription and translation, undergone by a DNA molecule to produce a protein or an RNA molecule. As used herein, a "gene" is a hereditary unit of DNA which comprises at least coding sequence; optionally included are other sequences such as introns, promoters, untranslated regions and other signal sequences.

As used herein "promoter" means a region of DNA sequence that is essential for the initiation of transcription of RNA from DNA; this region may also be referred to as a "5' regulatory region." Promoters are located upstream of DNA to be translated and have regions that act as binding sites for RNA polymerase and have regions that work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the site of initiation of transcription. The CAAT box element is usually located approximately 40 to 200 nucleotides upstream of the start site of transcription. The location of these basal promoter elements result in the synthesis of an RNA transcript comprising some number of nucleotides upstream of the translational ATG start site. The region of RNA upstream of the ATG is commonly referred to as a 5' untranslated region or 5' UTR. It is possible to use standard molecular biology techniques to make combinations of basal promoters, that is regions comprising sequences from the CAAT box to the translational start site, with other upstream promoter elements to enhance or otherwise alter promoter activity or specificity.

As is well known in the art, DNA constructs for use in transforming plants and expressing a coding sequence typically also comprise other regulatory elements in addition to a promoter, such as but not limited to 3' untranslated regions (such as polyadenylation sites), transit or signal peptides and marker coding sequences elements. For instance, see U.S. Pat. No. 6,437,217 which discloses a maize RS81 promoter, U.S. Pat. No. 5,641,876 which discloses a rice actin promoter, U.S. Pat. No. 6,426,446 which discloses a maize RS324 promoter, U.S. Pat. No. 6,429,362 which discloses a maize PR-1 promoter, U.S. Pat. No. 6,232,526 which discloses a maize A3 promoter, U.S. Pat. No. 6,177,611 which discloses constitutive maize promoters, U.S. Pat. Nos. 5,322,938, 5,352,605, 5,359,142 and 5,530,196 which disclose a 35S promoter, U.S. Pat. No. 6,433,252 which discloses a maize L3 oleosin promoter, U.S. Pat. No. 6,429,357 which discloses a rice actin 2 promoter and intron, U.S. Pat. No. 5,837,848 which discloses a root specific promoter, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, U.S. Pat. No. 6,175,060 which discloses phosphorus deficiency inducible promoters, U.S. Pat. No. 6,635,806, which discloses a coixin promoter, and U.S. Pat. No. 7,151,204, which discloses a maize chloroplast aldolase promoter, all of which are incorporated herein by reference. One skilled in the art would know that various introns, enhancers, transit peptides, targeting signal sequences, 5' and 3' untranslated regions (UTRs) useful in the design of effective plant expression vectors, such as those disclosed, for example, in U.S. Patent Application Publication 2003/01403641 (incorporated herein by reference), may be used in the promoter and coding sequence combination clones, such as, for example, those described in Table 2, to obtain and optimize expression of the gb1 coding sequence (SEQ ID NO:19) and homologs (SEQ ID NOS:20-34) of the invention.

In some aspects of the invention it is preferred that the promoter element in the exogenous DNA construct should be capable of causing sufficient expression of SEQ ID NOS:19-34 to result in the production of an effective amount of the proteins of SEQ ID NOS: 1-16 only under water-deficit conditions, cold conditions or other stress situations. By avoiding continuous high-level expression of transgenes, any undesired effects caused by continual over-expression of transgenes, or ectopic expression in various tissues or at various times, can be minimized or eliminated. Such promoters can be identified and isolated from the regulatory region of plant genes which are up-regulated in water-deficit conditions, cold or other stress conditions.

Specific water-deficit-inducible promoters for the expression of a maize gb1 coding sequence (SEQ ID NO:19) and homologs of a maize gb1 coding sequence (SEQ ID NOS:20-34) useful in the practice of this invention are derived from the 5' regulatory region of genes identified as a heat shock protein 17.5 gene (hsp17.5; SEQ ID NO:36), an HVA22 gene (hva22; SEQ ID NO:37), and a cinnamic acid 4-hydroxylase gene (ca4h; SEQ ID NO:38) of *Zea mays*. Such water-deficit-inducible promoters are disclosed in U.S. application Ser. No. 10/739,565, incorporated herein by reference. Additional specific water-deficit-inducible promoters useful in the practice of this invention are derived from the 5' regulatory region of genes identified as a heat shock protein 17.5 gene (hsp17.5; SEQ ID NO:41), an HVA22 gene (hva22; SEQ ID NO:42), a cinnamic acid 4-hydroxylase gene (ca4h; SEQ ID NO:43), an HSP16.9 gene (hsp16.9; SEQ ID NO:44), an HSP22 gene (hsp22; SEQ ID NO:45), and a rab-17 promoter (SEQ ID NO:47) of rice. Such water-deficit-inducible promoters are disclosed in U.S. provisional application Ser. No. 60/547,761, incorporated herein by reference. Additionally preferred water-deficit inducible promoters contemplated to be particularly useful in the practice of this invention include the rab-17 promoter reported by Vilardell et al., (*Plant Molecular Biology*, 17(5):985-993, 1990; SEQ ID NO:39) as well as a second, independently isolated rab-17 promoter (SEQ ID NO:40; disclosed in U.S. application Ser. No. 10/739,565).

It is also contemplated that a cold inducible promoter is a useful promoter for the expression of a maize gb1 coding sequence (SEQ ID NO:19) and homologs of a maize gb1 coding sequence (SEQ ID NOS:20-34). Cold inducible promoters have been isolated from a variety of plants and useful promoters include, for example, a wcs120 promoter from wheat (Oullet, F. et al., *FEBS Letters*. 423: 324-328, 1998), a ci7 promoter from potato (Kirch, H. et al., *Plant Mol Biol*., March; 33(5):897-909, 1997), an hva22 coding sequence from barley (Shen, Q., et al., *Plant Mol. Biol.*, February; 45(3):327-40, 2001), a cor15 promoter from *Arabidopsis* (Baker, S. et al., *Plant Mol. Biol.* March; 24(5):701-13, 1994), a kin1 or cor6.6 cold inducible promoter also from *Arabidopsis* (Wang H., et al., *Plant Mol. Biol*. July; 28(4):605-17, 1995) or the cold inducible promoters described in U.S. Pat. No. 6,084,089. A preferred cold inducible promoter is the maize cvy-cik1 promoter (SEQ ID NOS:48-52) or its rice homolog (SEQ ID NO:53). The cvy-cik1 promoter is induced in transgenic maize plants following cold treatment and is disclosed in U.S. provisional application Ser. No. 60/463,974, incorporated herein by reference in its entirety.

A useful promoter for expression a maize gb1 coding sequence is a promoter isolated from a maize gb1 gene (SEQ ID NO:47).

Tissue-specific promoters are also contemplated to be useful promoters for driving the expression of maize gb1 coding sequences and homologous sequences (SEQ ID NOS: 19-34). Such promoters include, but are not limited to, a phloem specific rice tungro bacilliform virus promoter (RTBV; SEQ ID NO:54 and U.S. Pat. No. 5,824,857), a maize root specific nicotianamine synthase promoter (SEQ ID NO:55), or a silk specific hydroxyproline rich glycoprotein promoter (hrgp; SEQ ID NOS:56).

During transformation, exogenous DNA may be introduced randomly, i.e. at a non-specific location, in the plant genome. In some cases, it may be useful to target an exogenous DNA insertion in order to achieve site-specific integration, e.g. to replace an existing gene sequence or region in the genome. In some other cases it may be useful to target an exogenous DNA integration into the genome at a predetermined site from which it is known that gene expression occurs. Several site-specific recombination systems exist which are known to function in plants include Cre/lox as disclosed in U.S. Pat. No. 4,959,317 and FLP/FRT as disclosed in U.S. Pat. No. 5,527,695, both incorporated herein by reference.

Constructs and vectors may also include a transit peptide for targeting of a protein or RNA product to a plant organelle, particularly to a chloroplast, leucoplast or other plastid organelle. For a description of the use of a chloroplast transit peptide see U.S. Pat. No. 5,188,642, incorporated herein by reference.

In practice DNA is introduced into only a small percentage of target cells in any one experiment. Marker genes are used to provide an efficient system for identification of those cells that are stably transformed by receiving and integrating an exogenous DNA construct into their genomes. Preferred marker genes provide selective markers which confer resistance to a selective agent, such as an antibiotic or herbicide. Potentially transformed cells are exposed to the selective agent. In the population of surviving cells will be those cells where, generally, the resistance-conferring coding sequence has been integrated and expressed at sufficient levels to permit cell survival. Cells may be tested further to confirm stable integration of the exogenous DNA. Useful selective marker genes include those conferring resistance to antibiotics such as kanamycin (nptII), hygromycin B (aph IV) and gentamycin (aac3 and aacC4) or resistance to herbicides such as glufosinate (bar or pat) and glyphosate (EPSPS; CP4). Examples of such selectable markers are illustrated in U.S. Pat. Nos. 5,550,318; 5,633,435; 5,780,708 and 6,118,047, all of which are incorporated herein by reference. Screenable markers which provide an ability to visually identify transformants can also be employed, e.g., a gene expressing a colored or fluorescent protein such as a luciferase or green fluorescent protein (GFP) or a gene expressing a beta-glucuronidase or uidA gene (GUS) for which various chromogenic substrates are known.

Protein Molecules

Proteins of the present invention which represent whole proteins or at least a sufficient portion of the entire protein to impart the relevant biological activity of the protein, e.g. increased glycine-betaine content in a transgenic organism. The term "protein" also includes molecules consisting of one or more polypeptide chains. Thus, a protein useful in the present invention may constitute an entire gene product or one or more functional portions of a natural protein which provides the agronomic trait of this invention, i.e. increased glycine-betaine, increased yield despite exposure to water-deficit, increased yield despite exposure to cold, increased yield under non-water-deficit conditions or increased yield under normal growing temperatures.

Homologs of the proteins of the present invention may be identified by comparison of the amino acid sequence of the GB1 protein of SEQ ID NO:1 to amino acid sequences of proteins from the same or different plant sources, e.g. manually or by using known homology-based search algorithms such as those commonly known and referred to as BLAST, FASTA, and Smith-Waterman.

A further aspect of the invention provides coding sequences which encode functional homologous proteins which differ in one or more amino acids from those of a GB1 protein provided herein as the result of one or more of the well-known conservative amino acid substitutions, e.g. valine is a conservative substitute for alanine and threonine is a conservative substitute for serine. When such a homologous protein is expressed in a transgenic plant, the homologous protein will affect the transgenic plant in a substantially equivalent manner as the GB1 protein.

Conservative substitutions for an amino acid within the native protein sequence can be selected from other members of a class to which the naturally occurring amino acid belongs. Representative amino acids within these various classes include, but are not limited to: (I) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine. Conserved substitutes for an amino acid within a native amino acid sequence can be selected from other members of the group to which the naturally occurring amino acid belongs. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Naturally conservative amino acids substitution groups are: valine-leucine, valine-isoleucine, phenylalanine-tyrosine, lysine-arginine, alanine-valine, aspartic acid-glutamic acid, and asparagine-glutamine.

A further aspect of the invention comprises proteins which differ in one or more amino acids from those of a described GB1 protein sequence as the result of deletion or insertion of one or more amino acids in a native sequence. When such a homologous protein is expressed in a transgenic plant, the homologous protein will affect the transgenic plant in a substantially equivalent manner as the GB1 protein, e.g., result in increased glycine-betaine content.

Proteins of the present invention that are variants of the proteins provided herein will generally demonstrate significant identity with the proteins provided herein. Of particular interest are proteins having at least 50% sequence identity, more preferably at least about 70% sequence identity or higher, e.g. at least about 80% sequence identity with a consensus amino acid sequence of SEQ ID NO:17 or SEQ ID NO:18. Of course useful proteins also include those with higher identity to a consensus sequence, e.g. 90%, to 100% identity. Other proteins of interest have at least 50% or more, e.g. at least 60% or 70% of homology with the proteins as defined by SEQ ID NO:1 through SEQ ID NO:16. Of course useful proteins also include those with higher percentage homology with the amino acids in a protein segment of SEQ ID NO:1 through SEQ ID NO:16, e.g., 80%, 90%, 95%, 98% or up to 100% homology.

Transformation Methods and Transgenic Plants

Methods and compositions for transforming plants by introducing an exogenous DNA into a plant genome in the practice of this invention can include any of the well-known and demonstrated methods. Preferred methods of plant transformation are microprojectile bombardment as illustrated in U.S. Pat. Nos. 5,015,580; 5,550,318; 5,538,880; 6,160,208; 6,399,861 and 6,403,865 and *Agrobacterium*-mediated transformation as illustrated in U.S. Pat. Nos. 5,635,055; 5,824, 877; 5,591,616; 5,981,840 and 6,384,301, all of which are incorporated herein by reference.

Transformation methods of this invention to provide plants with increased water-deficit, cold or other stress tolerance are preferably practiced in tissue culture on media and in a controlled environment. "Media" refers to the numerous liquid, solid, or semi-solid nutrient mixtures that are used to grow cells in vitro, that is, outside of the intact living organism. Recipient cell targets include, but are not limited to, meristem cells, callus, immature embryos and gametic cells such as microspores, pollen, sperm and egg cells. "Propagation" or "propagating" as used herein means the process of multiplying or breeding plant material. Therefore, propagation may involve maintaining a viable tissue on a media, e.g. a callus tissue on a solid medium, or growing a plant from seed or tissue, such as callus and cuttings.

As used herein "regeneration" means the process of growing a plant from a plant cell (e.g., plant protoplast, callus or explant). It is contemplated that any cell from which a fertile plant may be regenerated is useful as a recipient cell. Callus may be initiated from tissue sources including, but not limited to, immature embryos, seedling apical meristems, microspores and the like. Those cells which are capable of proliferating as callus also are recipient cells for genetic transformation. Practical transformation methods and materials for making transgenic plants of this invention, e.g. various media and recipient target cells, transformation of immature embryos and subsequent regeneration of fertile transgenic plants are disclosed in U.S. Pat. No. 6,194,636 and U.S. patent application Ser. No. 09/757,089, both of which are incorporated herein by reference.

As used herein a "transgenic" organism is one whose genome has been altered by the incorporation of foreign genetic material or additional copies of native genetic material, e.g. by transformation or recombination. The transgenic organism may be a plant, mammal, fungus, bacterium or virus. As used herein "transgenic plant" means a plant or progeny plant of any subsequent generation derived therefrom, wherein the DNA of the plant or progeny thereof contains an introduced exogenous DNA not originally present in a non-transgenic plant of the same strain. The transgenic plant may additionally contain sequences which are native to the plant being transformed, but wherein the exogenous DNA has been altered in order to alter the level or pattern of expression of the coding sequence.

As used herein an "$R_o$ transgenic plant" is a plant which has been directly transformed with an exogenous DNA or has been regenerated from a cell or cell cluster which has been transformed with an exogenous DNA. As used herein "progeny" means any subsequent generation, including the seeds and plants therefrom, which is derived from a particular parental plant or set of parental plants; the resultant progeny line may be inbred or hybrid. Progeny of a transgenic plant of this invention can be, for example, self-crossed, crossed to a transgenic plant, crossed to a non-transgenic plant, and/or back crossed. Thus, a transgenic maize plant prepared according to the invention may be an Ro plant, and progeny plants may be inbred or hybrid maize plants and may be heterozygous or homozygous for the exogenous DNA insertion. As used herein "crop plants" of interest include, but are not limited to soy, cotton, canola, wheat, sunflower, sorghum, alfalfa, barley, millet, rice, tobacco, fruit and vegetable crops, and turf grass. A preferred crop plant is Zea mays, commonly known as maize or corn.

The seeds of this invention are harvested from fertile transgenic plants and used to grow progeny generations of plants of this invention including a hybrid plant line comprising the exogenous DNA encoding proteins of SEQ ID NOS: 1-16 which provides the benefits of increased resistance and/or tolerance to stresses such as, but not limited to, water-deficit or cold and increase yield. The seeds of the invention also comprise increased glycine-betaine content as compared to a non-transgenic seed.

EXAMPLES

Having now generally described the invention, the same will be more readily understood through reference to the following examples which are provided by way of illustration, and are not intended to be limiting of the present invention, unless specified.

Example 1

Identification of a gb1 Gene from *Zea mays*

Plants from a number of non-transgenic inbred lines of *Zea mays* were field-grown under water-deficit (non-irrigated) or non-water-deficit (irrigated) conditions. Leaf samples were taken from plants before the tassel stage for each condition, and RNA and metabolites were isolated. RNA from the water-deficit and non-water-deficit samples was analyzed for differences using transcriptional profiling array methods. A number of RNAs were found to show differences in accumulation, to either higher or lower levels in the plants, depending upon the water treatment.

In addition to RNA transcription profiling, the glycine-betaine (GB) content was determined in leaf tissue samples from the inbred lines grown under water-deficit and non-water-deficit conditions. The characterized inbred maize lines were grouped into two categories: "GB accumulators," comprising greater than about 0.05 mM GB, and "GB non-accumulators," comprising less than about 0.05 mM GB.

One particular transcriptional profiling array element demonstrated an increase in RNA accumulation under water-deficit conditions compared to non-water-deficit conditions. In addition, under water-deficit conditions, plants in the study designated as "GB accumulators" were shown to have 3 to 12-fold higher levels of RNA transcript of this array element when compared to "GB non-accumulator" maize plants. These correlations were significant at the $p<0.005$ level across more than 85 commercial inbred lines of *Zea mays*. This array element was designated as the GB1 array element.

The GB1 array element was used as a probe in a Northern blot analysis using RNA samples from GB accumulator maize plants which were grown under both water-deficit and non-water-deficit conditions. The Northern blot analysis showed that the GB1 array element probe hybridized to a single RNA species which accumulated to much higher levels in water-deficit plants as compared to non-water-deficit plants. In contrast, when the GB1 array element was used as a probe against RNA samples from water-deficit and non-water-deficit plant tissues from GB non-accumulator lines, no hybridization was observed.

Sequence of the GB1 array element was used to identify a full-length sequence, designated the gb1 DNA, in a proprietary database of maize DNA sequences. Translation of the full-length gb1 DNA sequence (SEQ ID NO:19) indicated that the GB1 peptide sequence (SEQ ID NO:1) shares limited homology with particular histidine domains found in a sterol-4α-methyl oxidase cDNA from *Arabidopsis thaliana* (Darnet et al., 2001) and a C-4 methyl sterol oxidase from *Saccharomyces cerevisiae* (Bard et al., 1996). In these systems, however, these enzymes are thought to be involved in sterol metabolism and no role has been identified for the participation of these enzymes in the synthesis of glycine-betaine. Rafalski and Famodu (U.S. Pat. No. 6,479,733) propose the use of C-4 methyl sterol oxidase in the manipulation of sterol metabolism in a plant; the sequence of the present invention and that of Rafalski and Famodu are only distantly related at the polynucleotide and amino acid levels. Additionally, Lalgudi et al., (U.S. Patent Application Publication No. 2001/0051335 A1) disclose short DNA and protein fragments identified only as "corn tassel-derived polynucleotides (cdps) which encode corn tassel-derived proteins (CDPs)" which show sequence similarity to the GB1 sequence identified by the current inventors. Lalgudi et al., do not disclose a function for the cdps and CDPs in the synthesis of glycine-betaine, for water-deficit or cold tolerance, nor for increased yield. Alignments of proteins exhibiting homology to the maize GB1 protein of the current invention as well as alignments describing consensus regions are shown in FIG. 1 and FIG. 2 which are used to identify consensus amino acid sequences of SEQ ID NO:17 and SEQ ID NO:18, respectively.

Example 2

Over-Expression of Exogenous DNA Constructs Comprising gb1 Coding Sequence in Transgenic *Zea mays*

Transgenic *Zea mays* of a GB non-accumulator line was prepared with an exogenous DNA comprising a constitutive promoter region comprising a rice actin 1 promoter and a rice actin 1 intron operably linked to the gb1 coding sequence of SEQ ID NO:19 encoding the GB1 polynucleotide of SEQ ID NO:1 (see pMON78450 in FIG. 3 and SEQ ID NO:57). $R_o$ transgenic plants comprising low copy number events (that is, about 1-2 copies based upon molecular analysis) were selected for study. Transgenic non-accumulator plants comprising the gb1 exogenous DNA and non-transgenic control plants of both a GB non-accumulator line and a GB accumulator line were grown under greenhouse conditions and leaf samples taken at approximately the V6-V8 stage. Leaf samples from a total of 45 different transgenic events were examined for GB accumulation. Leaf samples were lyophilized, ground to a fine powder and metabolites extracted into an ethanol-based extraction buffer supplemented with deuterated glycine-betaine as an internal standard metabolite. Samples were analyzed by liquid chromatography-mass spectrometry/mass spectrometry and the amount of glycine-betaine (in mM) determined by analyzing the ratio of the deuterated and non-deuterated glycine-betaine in a sample.

Glycine-betaine was found to accumulate to significantly higher levels in the gb1 transgenic plants when compared to both the GB non-accumulator (LH59) and GB accumulator (FBLL) non-transgenic plants. On average, in the V6-V8 plants, the gb1 transgenic plants contained approximately 7.2 mM GB per sample as compared to 3.0 mM and 0.1 mM in the non-transgenic GB accumulator FBLL and GB non-accumulator LH244 lines, respectively. This represents an approximately 70-fold increase in GB in the transgenic plants compared to the non-transgenic GB non-accumulator lines and an approximately 2.4-fold increase compared to the GB non-transgenic accumulator line. As can been seen from Table 1, the range of accumulated GB in the transgenic plants was from 0.1 mM to 22.6 mM. $R_o$ transgenic plants were outcrossed and progeny seed prepared for propagation of $F_1$, $F_2$ and other generations of progeny plants and seeds and additional analysis of glycine-betaine indicated that the metabolite continued to accumulate to increased levels in the progeny plants (see for example, Tables 3 and 4 in Example 5).

Studies also indicated that the amount of GB in tissue increased with the age of the plant. For example, older VT leaves of a non-transgenic FBLL×LH59 hybrid accumulated more of the metabolite than younger V5 leaves.

TABLE 1

Glycine-betaine accumulation in $R_0$ gb1 transgenic plants.

| Line | Accumulator Type* | n | Mean GB(mM) | Std Dev | Min | Max |
|---|---|---|---|---|---|---|
| LH59/GB1 | Non-accumulator with transgene | 45[a] | 7.2 | 4.70 | 0.1 | 22.6 |
| LH59 | Non-accumulator | 11[b] | 0.1 | 0.14 | 0.008 | 0.4 |
| FBLL | Accumulator | 4[b] | 3.0 | 0.59 | 2.1 | 3.66 |

*Indicates characterization of maize line without transgene.
[a] = represents 45 different events, one plant from each event.
[b] = represents the number of individual plants of each non-transgenic line Example 3

Expression of Exogenous DNA Constructs Comprising gb1 Coding Sequence and Homologs in Transgenic *Zea mays*

In substantially the same manner as in Example 2, a variety of exogenous DNA constructs comprising a gb1 coding sequence are transformed into the GB non-accumulating maize line (LH59) and a GB accumulating maize line (FBLL MAB, U.S Patent Application Publication 20040016030, incorporated herein by reference). The gb1-containing DNA constructs are substantially similar to the construct illustrated in FIG. 3 except for combinations of promoter and gb1 coding sequence as described Table 2 where the promoter identified by "promoter sequence" replaces the rice actin 1 promoter and the gb1 coding sequence identified by "gb1 DNA sequence" replaces the maize gb1 coding sequence. The rice actin 1 intron is retained or deleted or replaced with other introns in the various constructs.

TABLE 2

Coding sequence and promoter combinations for the expression of gb1 coding sequences.

| Promoter | Promoter sequence | gb1 | gb1 coding sequence |
|---|---|---|---|
| hsp17.5 promoter | SEQ ID NO: 36 | maize gb1 | SEQ ID NO: 19 |
| hva22 promoter | SEQ ID NO: 37 | maize gb1 | SEQ ID NO: 19 |
| ca4h promoter | SEQ ID NO: 38 | maize gb1 | SEQ ID NO: 19 |
| rab-17 promoter | SEQ ID NO: 39 | maize gb1 | SEQ ID NO: 19 |
| rab-17 promoter | SEQ ID NO: 40 | maize gb1 | SEQ ID NO: 19 |
| hsp17.5 promoter | SEQ ID NO: 41 | maize gb1 | SEQ ID NO: 19 |
| hva22 promoter | SEQ ID NO: 42 | maize gb1 | SEQ ID NO: 19 |
| ca4h promoter | SEQ ID NO: 43 | maize gb1 | SEQ ID NO: 19 |
| hsp16.9 promoter | SEQ ID NO: 44 | maize gb1 | SEQ ID NO: 19 |
| hsp22 promoter | SEQ ID NO: 45 | maize gb1 | SEQ ID NO: 19 |
| rab-17 promoter | SEQ ID NO: 46 | maize gb1 | SEQ ID NO: 19 |

TABLE 2-continued

Coding sequence and promoter combinations for the expression of gb1 coding sequences.

| Promoter | Promoter sequence | gb1 | gb1 coding sequence |
|---|---|---|---|
| maize gb1 promoter | SEQ ID NO: 47 | maize gb1 | SEQ ID NO: 19 |
| maize cvy-cik1 promoter | SEQ ID NO: 48 | maize gb1 | SEQ ID NO: 19 |
| maize cvy-cik1 promoter | SEQ ID NO: 49 | maize gb1 | SEQ ID NO: 19 |
| maize cvy-cik1 promoter | SEQ ID NO: 50 | maize gb1 | SEQ ID NO: 19 |
| maize cvy-cik1 promoter | SEQ ID NO: 51 | maize gb1 | SEQ ID NO: 19 |
| maize cvy-cik1 promoter | SEQ ID NO: 52 | maize gb1 | SEQ ID NO: 19 |
| rice cvy-cik1 promoter | SEQ ID NO: 53 | maize gb1 | SEQ ID NO: 19 |
| rtbv promoter | SEQ ID NO: 54 | maize gb1 | SEQ ID NO: 19 |
| maize nas promoter | SEQ ID NO: 55 | maize gb1 | SEQ ID NO: 19 |
| coix hrgp promoter | SEQ ID NO: 56 | maize gb1 | SEQ ID NO: 19 |
| rice actin 1 promoter and intron | SEQ ID NO: 35 | maize gb1-2 | SEQ ID NO: 20 |
| hsp17.5 promoter | SEQ ID NO: 36 | maize gb1-2 | SEQ ID NO: 20 |
| hva22 promoter | SEQ ID NO: 37 | maize gb1-2 | SEQ ID NO: 20 |
| ca4h promoter | SEQ ID NO: 38 | maize gb1-2 | SEQ ID NO: 20 |
| rab-17 promoter | SEQ ID NO: 39 | maize gb1-2 | SEQ ID NO: 20 |
| rab-17 promoter | SEQ ID NO: 40 | maize gb1-2 | SEQ ID NO: 20 |
| hsp17.5 promoter | SEQ ID NO: 41 | maize gb1-2 | SEQ ID NO: 20 |
| hva22 promoter | SEQ ID NO: 42 | maize gb1-2 | SEQ ID NO: 20 |
| ca4h promoter | SEQ ID NO: 43 | maize gb1-2 | SEQ ID NO: 20 |
| hsp16.9 promoter | SEQ ID NO: 44 | maize gb1-2 | SEQ ID NO: 20 |
| hsp22 promoter | SEQ ID NO: 45 | maize gb1-2 | SEQ ID NO: 20 |
| rab-17 promoter | SEQ ID NO: 46 | maize gb1-2 | SEQ ID NO: 20 |
| maize gb1 promoter | SEQ ID NO: 47 | maize gb1-2 | SEQ ID NO: 20 |
| maize cvy-cik1 promoter | SEQ ID NO: 48 | maize gb1-2 | SEQ ID NO: 20 |
| maize cvy-cik1 promoter | SEQ ID NO: 49 | maize gb1-2 | SEQ ID NO: 20 |
| maize cvy-cik1 promoter | SEQ ID NO: 50 | maize gb1-2 | SEQ ID NO: 20 |
| maize cvy-cik1 promoter | SEQ ID NO: 51 | maize gb1-2 | SEQ ID NO: 20 |
| maize cvy-cik1 promoter | SEQ ID NO: 52 | maize gb1-2 | SEQ ID NO: 20 |
| rice cvy-cik1 promoter | SEQ ID NO: 53 | maize gb1-2 | SEQ ID NO: 20 |
| rtbv promoter | SEQ ID NO: 54 | maize gb1-2 | SEQ ID NO: 20 |
| maize nas promoter | SEQ ID NO: 55 | maize gb1-2 | SEQ ID NO: 20 |
| coix hrgp promoter | SEQ ID NO: 56 |

TABLE 2-continued

Coding sequence and promoter combinations for the expression of gb1 coding sequences.

| Promoter | Promoter sequence | gb1 | gb1 coding sequence |
|---|---|---|---|
| rice actin 1 promoter and intron | SEQ ID NO: 35 | barley gb1-1 | SEQ ID NO: 22 |
| hsp17.5 promoter | SEQ ID NO: 36 | barley gb1-1 | SEQ ID NO: 22 |
| hva22 promoter | SEQ ID NO: 37 | barley gb1-1 | SEQ ID NO: 22 |
| ca4h promoter | SEQ ID NO: 38 | barley gb1-1 | SEQ ID NO: 22 |
| rab-17 promoter | SEQ ID NO: 39 | barley gb1-1 | SEQ ID NO: 22 |
| rab-17 promoter | SEQ ID NO: 40 | barley gb1-1 | SEQ ID NO: 22 |
| hsp17.5 promoter | SEQ ID NO: 41 | barley gb1-1 | SEQ ID NO: 22 |
| hva22 promoter | SEQ ID NO: 42 | barley gb1-1 | SEQ ID NO: 22 |
| ca4h promoter | SEQ ID NO: 43 | barley gb1-1 | SEQ ID NO: 22 |
| hsp16.9 promoter | SEQ ID NO: 44 | barley gb1-1 | SEQ ID NO: 22 |
| hsp22 promoter | SEQ ID NO: 45 | barley gb1-1 | SEQ ID NO: 22 |
| rab-17 promoter | SEQ ID NO: 46 | barley gb1-1 | SEQ ID NO: 22 |
| maize gb1 promoter | SEQ ID NO: 47 | barley gb1-1 | SEQ ID NO: 22 |
| maize cvy-cik1 promoter | SEQ ID NO: 48 | barley gb1-1 | SEQ ID NO: 22 |
| maize cvy-cik1 promoter | SEQ ID NO: 49 | barley gb1-1 | SEQ ID NO: 22 |
| maize cvy-cik1 promoter | SEQ ID NO: 50 | barley gb1-1 | SEQ ID NO: 22 |
| maize cvy-cik1 promoter | SEQ ID NO: 51 | barley gb1-1 | SEQ ID NO: 22 |
| maize cvy-cik1 promoter | SEQ ID NO: 52 | barley gb1-1 | SEQ ID NO: 22 |
| rice cvy-cik1 promoter | SEQ ID NO: 53 | barley gb1-1 | SEQ ID NO: 22 |
| rtbv promoter | SEQ ID NO: 54 | barley gb1-1 | SEQ ID NO: 22 |
| maize nas promoter | SEQ ID NO: 55 | barley gb1-1 | SEQ ID NO: 22 |
| coix hrgp promoter | SEQ ID NO: 56 | barley gb1-1 | SEQ ID NO: 22 |
| rice actin 1 promoter and intron | SEQ ID NO: 35 | maize gb1-3-1 | SEQ ID NO: 23 |
| hsp17.5 promoter | SEQ ID NO: 36 | maize gb1-3-1 | SEQ ID NO: 23 |
| hva22 promoter | SEQ ID NO: 37 | maize gb1-3-1 | SEQ ID NO: 23 |
| ca4h promoter | SEQ ID NO: 38 | maize gb1-3-1 | SEQ ID NO: 23 |
| rab-17 promoter | SEQ ID NO: 39 | maize gb1-3-1 | SEQ ID NO: 23 |
| rab-17 promoter | SEQ ID NO: 40 | maize gb1-3-1 | SEQ ID NO: 23 |
| hsp17.5 promoter | SEQ ID NO: 41 | maize gb1-3-1 | SEQ ID NO: 23 |
| hva22 promoter | SEQ ID NO: 42 | maize gb1-3-1 | SEQ ID NO: 23 |
| ca4h promoter | SEQ ID NO: 43 | maize gb1-3-1 | SEQ ID NO: 23 |
| hsp16.9 promoter | SEQ ID NO: 44 | maize gb1-3-1 | SEQ ID NO: 23 |
| hsp22 promoter | SEQ ID NO: 45 | maize gb1-3-1 | SEQ ID NO: 23 |
| rab-17 promoter | SEQ ID NO: 46 | maize gb1-3-1 | SEQ ID NO: 23 |
| maize gb1 promoter | SEQ ID NO: 47 | maize gb1-3-1 | SEQ ID NO: 23 |
| maize cvy-cik1 promoter | SEQ ID NO: 48 | maize gb1-3-1 | SEQ ID NO: 23 |
| maize cvy-cik1 promoter | SEQ ID NO: 49 | maize gb1-3-1 | SEQ ID NO: 23 |
| maize cvy-cik1 promoter | SEQ ID NO: 50 | maize gb1-3-1 | SEQ ID NO: 23 |
| maize cvy-cik1 promoter | SEQ ID NO: 51 | maize gb1-3-1 | SEQ ID NO: 23 |
| maize cvy-cik1 promoter | SEQ ID NO: 52 | maize gb1-3-1 | SEQ ID NO: 23 |
| rice cvy-cik1 promoter | SEQ ID NO: 53 | maize gb1-3-1 | SEQ ID NO: 23 |
| rtbv promoter | SEQ ID NO: 54 | maize gb1-3-1 | SEQ ID NO: 23 |
| maize nas promoter | SEQ ID NO: 55 | maize gb1-3-1 | SEQ ID NO: 23 |
| coix hrgp promoter | SEQ ID NO: 56 | maize gb1-3-1 | SEQ ID NO: 23 |
| rice actin 1 promoter and intron | SEQ ID NO: 35 | leek gb1-3-1 | SEQ ID NO: 24 |
| hsp17.5 promoter | SEQ ID NO: 36 | leek gb1-3-1 | SEQ ID NO: 24 |
| hva22 promoter | SEQ ID NO: 37 | leek gb1-3-1 | SEQ ID NO: 24 |
| ca4h promoter | SEQ ID NO: 38 | leek gb1-3-1 | SEQ ID NO: 24 |
| rab-17 promoter | SEQ ID NO: 39 | leek gb1-3-1 | SEQ ID NO: 24 |
| rab-17 promoter | SEQ ID NO: 40 | leek gb1-3-1 | SEQ ID NO: 24 |
| hsp17.5 promoter | SEQ ID NO: 41 | leek gb1-3-1 | SEQ ID NO: 24 |
| hva22 promoter | SEQ ID NO: 42 | leek gb1-3-1 | SEQ ID NO: 24 |
| ca4h promoter | SEQ ID NO: 43 | leek gb1-3-1 | SEQ ID NO: 24 |
| hsp16.9 promoter | SEQ ID NO: 44 | leek gb1-3-1 | SEQ ID NO: 24 |
| hsp22 promoter | SEQ ID NO: 45 | leek gb1-3-1 | SEQ ID NO: 24 |
| rab-17 promoter | SEQ ID NO: 46 | leek gb1-3-1 | SEQ ID NO: 24 |
| maize gb1 promoter | SEQ ID NO: 47 | leek gb1-3-1 | SEQ ID NO: 24 |
| maize cvy-cik1 promoter | SEQ ID NO: 48 | leek gb1-3-1 | SEQ ID NO: 24 |

TABLE 2-continued

Coding sequence and promoter combinations for the expression of gb1 coding sequences.

| Promoter | Promoter sequence | gb1 | gb1 coding sequence |
|---|---|---|---|
| maize cvy-cik1 promoter | SEQ ID NO: 49 | leek gb1-3-1 | SEQ ID NO: 24 |
| maize cvy-cik1 promoter | SEQ ID NO: 50 | leek gb1-3-1 | SEQ ID NO: 24 |
| maize cvy-cik1 promoter | SEQ ID NO: 51 | leek gb1-3-1 | SEQ ID NO: 24 |
| maize cvy-cik1 promoter | SEQ ID NO: 52 | leek gb1-3-1 | SEQ ID NO: 24 |
| rice cvy-cik1 promoter | SEQ ID NO: 53 | leek gb1-3-1 | SEQ ID NO: 24 |
| rtbv promoter | SEQ ID NO: 54 | leek gb1-3-1 | SEQ ID NO: 24 |
| maize nas promoter | SEQ ID NO: 55 | leek gb1-3-1 | SEQ ID NO: 24 |
| coix hrgp promoter | SEQ ID NO: 56 | leek gb1-3-1 | SEQ ID NO: 24 |
| rice actin 1 promoter and intron | SEQ ID NO: 35 | At gb1-3-1 | SEQ ID NO: 25 |
| hsp17.5 promoter | SEQ ID NO: 36 | At gb1-3-1 | SEQ ID NO: 25 |
| hva22 promoter | SEQ ID NO: 37 | At gb1-3-1 | SEQ ID NO: 25 |
| ca4h promoter | SEQ ID NO: 38 | At gb1-3-1 | SEQ ID NO: 25 |
| rab-17 promoter | SEQ ID NO: 39 | At gb1-3-1 | SEQ ID NO: 25 |
| rab-17 promoter | SEQ ID NO: 40 | At gb1-3-1 | SEQ ID NO: 25 |
| hsp17.5 promoter | SEQ ID NO: 41 | At gb1-3-1 | SEQ ID NO: 25 |
| hva22 promoter | SEQ ID NO: 42 | At gb1-3-1 | SEQ ID NO: 25 |
| ca4h promoter | SEQ ID NO: 43 | At gb1-3-1 | SEQ ID NO: 25 |
| hsp16.9 promoter | SEQ ID NO: 44 | At gb1-3-1 | SEQ ID NO: 25 |
| hsp22 promoter | SEQ ID NO: 45 | At gb1-3-1 | SEQ ID NO: 25 |
| rab-17 promoter | SEQ ID NO: 46 | At gb1-3-1 | SEQ ID NO: 25 |
| maize gb1 promoter | SEQ ID NO: 47 | At gb1-3-1 | SEQ ID NO: 25 |
| maize cvy-cik1 promoter | SEQ ID NO: 48 | At gb1-3-1 | SEQ ID NO: 25 |
| maize cvy-cik1 promoter | SEQ ID NO: 49 | At gb1-3-1 | SEQ ID NO: 25 |
| maize cvy-cik1 promoter | SEQ ID NO: 50 | At gb1-3-1 | SEQ ID NO: 25 |
| maize cvy-cik1 promoter | SEQ ID NO: 51 | At gb1-3-1 | SEQ ID NO: 25 |
| maize cvy-cik1 promoter | SEQ ID NO: 52 | At gb1-3-1 | SEQ ID NO: 25 |
| rice cvy-cik1 promoter | SEQ ID NO: 53 | At gb1-3-1 | SEQ ID NO: 25 |
| rtbv promoter | SEQ ID NO: 54 | At gb1-3-1 | SEQ ID NO: 25 |
| maize nas promoter | SEQ ID NO: 55 | At gb1-3-1 | SEQ ID NO: 25 |
| coix hrgp promoter | SEQ ID NO: 56 | At gb1-3-1 | SEQ ID NO: 25 |
| rice actin 1 promoter and intron | SEQ ID NO: 35 | At gb1-3-2 | SEQ ID NO: 26 |
| hsp17.5 promoter | SEQ ID NO: 36 | At gb1-3-2 | SEQ ID NO: 26 |
| hva22 promoter | SEQ ID NO: 37 | At gb1-3-2 | SEQ ID NO: 26 |
| ca4h promoter | SEQ ID NO: 38 | At gb1-3-2 | SEQ ID NO: 26 |
| rab-17 promoter | SEQ ID NO: 39 | At gb1-3-2 | SEQ ID NO: 26 |
| rab-17 promoter | SEQ ID NO: 40 | At gb1-3-2 | SEQ ID NO: 26 |
| hsp17.5 promoter | SEQ ID NO: 41 | At gb1-3-2 | SEQ ID NO: 26 |
| hva22 promoter | SEQ ID NO: 42 | At gb1-3-2 | SEQ ID NO: 26 |
| ca4h promoter | SEQ ID NO: 43 | At gb1-3-2 | SEQ ID NO: 26 |
| hsp16.9 promoter | SEQ ID NO: 44 | At gb1-3-2 | SEQ ID NO: 26 |
| hsp22 promoter | SEQ ID NO: 45 | At gb1-3-2 | SEQ ID NO: 26 |
| rab-17 promoter | SEQ ID NO: 46 | At gb1-3-2 | SEQ ID NO: 26 |
| maize gb1 promoter | SEQ ID NO: 47 | At gb1-3-2 | SEQ ID NO: 26 |
| maize cvy-cik1 promoter | SEQ ID NO: 48 | At gb1-3-2 | SEQ ID NO: 26 |
| maize cvy-cik1 promoter | SEQ ID NO: 49 | At gb1-3-2 | SEQ ID NO: 26 |
| maize cvy-cik1 promoter | SEQ ID NO: 50 | At gb1-3-2 | SEQ ID NO: 26 |
| maize cvy-cik1 promoter | SEQ ID NO: 51 | At gb1-3-2 | SEQ ID NO: 26 |
| maize cvy-cik1 promoter | SEQ ID NO: 52 | At gb1-3-2 | SEQ ID NO: 26 |
| rice cvy-cik1 promoter | SEQ ID NO: 53 | At gb1-3-2 | SEQ ID NO: 26 |
| rtbv promoter | SEQ ID NO: 54 | At gb1-3-2 | SEQ ID NO: 26 |
| maize nas promoter | SEQ ID NO: 55 | At gb1-3-2 | SEQ ID NO: 26 |
| coix hrgp promoter | SEQ ID NO: 56 | At gb1-3-2 | SEQ ID NO: 26 |
| rice actin 1 promoter and intron | SEQ ID NO: 35 | At gb1-3-3 | SEQ ID NO: 27 |
| hsp17.5 promoter | SEQ ID NO: 36 | At gb1-3-3 | SEQ ID NO: 27 |

TABLE 2-continued

Coding sequence and promoter combinations for the expression of gb1 coding sequences.

| Promoter | Promoter sequence | gb1 | gb1 coding sequence |
|---|---|---|---|
| hva22 promoter | SEQ ID NO: 37 | At gb1-3-3 | SEQ ID NO: 27 |
| ca4h promoter | SEQ ID NO: 38 | At gb1-3-3 | SEQ ID NO: 27 |
| rab-17 promoter | SEQ ID NO: 39 | At gb1-3-3 | SEQ ID NO: 27 |
| rab-17 promoter | SEQ ID NO: 40 | At gb1-3-3 | SEQ ID NO: 27 |
| hsp17.5 promoter | SEQ ID NO: 41 | At gb1-3-3 | SEQ ID NO: 27 |
| hva22 promoter | SEQ ID NO: 42 | At gb1-3-3 | SEQ ID NO: 27 |
| ca4h promoter | SEQ ID NO: 43 | At gb1-3-3 | SEQ ID NO: 27 |
| hsp16.9 promoter | SEQ ID NO: 44 | At gb1-3-3 | SEQ ID NO: 27 |
| hsp22 promoter | SEQ ID NO: 45 | At gb1-3-3 | SEQ ID NO: 27 |
| rab-17 promoter | SEQ ID NO: 46 | At gb1-3-3 | SEQ ID NO: 27 |
| maize gb1 promoter | SEQ ID NO: 47 | At gb1-3-3 | SEQ ID NO: 27 |
| maize cvy-cik1 promoter | SEQ ID NO: 48 | At gb1-3-3 | SEQ ID NO: 27 |
| maize cvy-cik1 promoter | SEQ ID NO: 49 | At gb1-3-3 | SEQ ID NO: 27 |
| maize cvy-cik1 promoter | SEQ ID NO: 50 | At gb1-3-3 | SEQ ID NO: 27 |
| maize cvy-cik1 promoter | SEQ ID NO: 51 | At gb1-3-3 | SEQ ID NO: 27 |
| maize cvy-cik1 promoter | SEQ ID NO: 52 | At gb1-3-3 | SEQ ID NO: 27 |
| rice cvy-cik1 promoter | SEQ ID NO: 53 | At gb1-3-3 | SEQ ID NO: 27 |
| rtbv promoter | SEQ ID NO: 54 | At gb1-3-3 | SEQ ID NO: 27 |
| maize nas promoter | SEQ ID NO: 55 | At gb1-3-3 | SEQ ID NO: 27 |
| coix hrgp promoter | SEQ ID NO: 56 | At gb1-3-3 | SEQ ID NO: 27 |
| rice actin 1 promoter and intron | SEQ ID NO: 35 | At gb1-3-4 | SEQ ID NO: 28 |
| hsp17.5 promoter | SEQ ID NO: 36 | At gb1-3-4 | SEQ ID NO: 28 |
| hva22 promoter | SEQ ID NO: 37 | At gb1-3-4 | SEQ ID NO: 28 |
| ca4h promoter | SEQ ID NO: 38 | At gb1-3-4 | SEQ ID NO: 28 |
| rab-17 promoter | SEQ ID NO: 39 | At gb1-3-4 | SEQ ID NO: 28 |
| rab-17 promoter | SEQ ID NO: 40 | At gb1-3-4 | SEQ ID NO: 28 |
| hsp17.5 promoter | SEQ ID NO: 41 | At gb1-3-4 | SEQ ID NO: 28 |
| hva22 promoter | SEQ ID NO: 42 | At gb1-3-4 | SEQ ID NO: 28 |
| ca4h promoter | SEQ ID NO: 43 | At gb1-3-4 | SEQ ID NO: 28 |
| hsp16.9 promoter | SEQ ID NO: 44 | At gb1-3-4 | SEQ ID NO: 28 |
| hsp22 promoter | SEQ ID NO: 45 | At gb1-3-4 | SEQ ID NO: 28 |
| rab-17 promoter | SEQ ID NO: 46 | At gb1-3-4 | SEQ ID NO: 28 |
| maize gb1 promoter | SEQ ID NO: 47 | At gb1-3-4 | SEQ ID NO: 28 |
| maize cvy-cik1 promoter | SEQ ID NO: 48 | At gb1-3-4 | SEQ ID NO: 28 |
| maize cvy-cik1 promoter | SEQ ID NO: 49 | At gb1-3-4 | SEQ ID NO: 28 |
| maize cvy-cik1 promoter | SEQ ID NO: 50 | At gb1-3-4 | SEQ ID NO: 28 |
| maize cvy-cik1 promoter | SEQ ID NO: 51 | At gb1-3-4 | SEQ ID NO: 28 |
| maize cvy-cik1 promoter | SEQ ID NO: 52 | At gb1-3-4 | SEQ ID NO: 28 |
| rice cvy-cik1 promoter | SEQ ID NO: 53 | At gb1-3-4 | SEQ ID NO: 28 |
| rtbv promoter | SEQ ID NO: 54 | At gb1-3-4 | SEQ ID NO: 28 |
| maize nas promoter | SEQ ID NO: 55 | At gb1-3-4 | SEQ ID NO: 28 |
| coix hrgp promoter | SEQ ID NO: 56 | At gb1-3-4 | SEQ ID NO: 28 |
| rice actin 1 promoter and intron | SEQ ID NO: 35 | Bn gb1-3-1 | SEQ ID NO: 29 |
| hsp17.5 promoter | SEQ ID NO: 36 | Bn gb1-3-1 | SEQ ID NO: 29 |
| hva22 promoter | SEQ ID NO: 37 | Bn gb1-3-1 | SEQ ID NO: 29 |
| ca4h promoter | SEQ ID NO: 38 | Bn gb1-3-1 | SEQ ID NO: 29 |
| rab-17 promoter | SEQ ID NO: 39 | Bn gb1-3-1 | SEQ ID NO: 29 |
| rab-17 promoter | SEQ ID NO: 40 | Bn gb1-3-1 | SEQ ID NO: 29 |
| hsp17.5 promoter | SEQ ID NO: 41 | Bn gb1-3-1 | SEQ ID NO: 29 |
| hva22 promoter | SEQ ID NO: 42 | Bn gb1-3-1 | SEQ ID NO: 29 |
| ca4h promoter | SEQ ID NO: 43 | Bn gb1-3-1 | SEQ ID NO: 29 |
| hsp16.9 promoter | SEQ ID NO: 44 | Bn gb1-3-1 | SEQ ID NO: 29 |
| hsp22 promoter | SEQ ID NO: 45 | Bn gb1-3-1 | SEQ ID NO: 29 |
| rab-17 promoter | SEQ ID NO: 46 | Bn gb1-3-1 | SEQ ID NO: 29 |
| maize gb1 promoter | SEQ ID NO: 47 | Bn gb1-3-1 | SEQ ID NO: 29 |
| maize cvy-cik1 promoter | SEQ ID NO: 48 | Bn gb1-3-1 | SEQ ID NO: 29 |
| maize cvy-cik1 promoter | SEQ ID NO: 49 | Bn gb1-3-1 | SEQ ID NO: 29 |

TABLE 2-continued

Coding sequence and promoter combinations for the expression of gb1 coding sequences.

| Promoter | Promoter sequence | gb1 | gb1 coding sequence |
|---|---|---|---|
| maize cvy-cik1 promoter | SEQ ID NO: 50 | Bn gb1-3-1 | SEQ ID NO: 29 |
| maize cvy-cik1 promoter | SEQ ID NO: 51 | Bn gb1-3-1 | SEQ ID NO: 29 |
| maize cvy-cik1 promoter | SEQ ID NO: 52 | Bn gb1-3-1 | SEQ ID NO: 29 |
| rice cvy-cik1 promoter | SEQ ID NO: 53 | Bn gb1-3-1 | SEQ ID NO: 29 |
| rtbv promoter | SEQ ID NO: 54 | Bn gb1-3-1 | SEQ ID NO: 29 |
| maize nas promoter | SEQ ID NO: 55 | Bn gb1-3-1 | SEQ ID NO: 29 |
| coix hrgp promoter | SEQ ID NO: 56 | Bn gb1-3-1 | SEQ ID NO: 29 |
| rice actin 1 promoter and intron | SEQ ID NO: 35 | soybean gb1-3-1 | SEQ ID NO: 30 |
| hsp17.5 promoter | SEQ ID NO: 36 | soybean gb1-3-1 | SEQ ID NO: 30 |
| hva22 promoter | SEQ ID NO: 37 | soybean gb1-3-1 | SEQ ID NO: 30 |
| ca4h promoter | SEQ ID NO: 38 | soybean gb1-3-1 | SEQ ID NO: 30 |
| rab-17 promoter | SEQ ID NO: 39 | soybean gb1-3-1 | SEQ ID NO: 30 |
| rab-17 promoter | SEQ ID NO: 40 | soybean gb1-3-1 | SEQ ID NO: 30 |
| hsp17.5 promoter | SEQ ID NO: 41 | soybean gb1-3-1 | SEQ ID NO: 30 |
| hva22 promoter | SEQ ID NO: 42 | soybean gb1-3-1 | SEQ ID NO: 30 |
| ca4h promoter | SEQ ID NO: 43 | soybean gb1-3-1 | SEQ ID NO: 30 |
| hsp16.9 promoter | SEQ ID NO: 44 | soybean gb1-3-1 | SEQ ID NO: 30 |
| hsp22 promoter | SEQ ID NO: 45 | soybean gb1-3-1 | SEQ ID NO: 30 |
| rab-17 promoter | SEQ ID NO: 46 | soybean gb1-3-1 | SEQ ID NO: 30 |
| maize gb1 promoter | SEQ ID NO: 47 | soybean gb1-3-1 | SEQ ID NO: 30 |
| maize cvy-cik1 promoter | SEQ ID NO: 48 | soybean gb1-3-1 | SEQ ID NO: 30 |
| maize cvy-cik1 promoter | SEQ ID NO: 49 | soybean gb1-3-1 | SEQ ID NO: 30 |
| maize cvy-cik1 promoter | SEQ ID NO: 50 | soybean gb1-3-1 | SEQ ID NO: 30 |
| maize cvy-cik1 promoter | SEQ ID NO: 51 | soybean gb1-3-1 | SEQ ID NO: 30 |
| maize cvy-cik1 promoter | SEQ ID NO: 52 | soybean gb1-3-1 | SEQ ID NO: 30 |
| rice cvy-cik1 promoter | SEQ ID NO: 53 | soybean gb1-3-1 | SEQ ID NO: 30 |
| rtbv promoter | SEQ ID NO: 54 | soybean gb1-3-1 | SEQ ID NO: 30 |
| maize nas promoter | SEQ ID NO: 55 | soybean gb1-3-1 | SEQ ID NO: 30 |
| coix hrgp promoter | SEQ ID NO: 56 | soybean gb1-3-1 | SEQ ID NO: 30 |
| rice actin 1 promoter and intron | SEQ ID NO: 35 | soybean gb1-3-2 | SEQ ID NO: 31 |
| hsp17.5 promoter | SEQ ID NO: 36 | soybean gb1-3-2 | SEQ ID NO: 31 |
| hva22 promoter | SEQ ID NO: 37 | soybean gb1-3-2 | SEQ ID NO: 31 |
| ca4h promoter | SEQ ID NO: 38 | soybean gb1-3-2 | SEQ ID NO: 31 |
| rab-17 promoter | SEQ ID NO: 39 | soybean gb1-3-2 | SEQ ID NO: 31 |
| rab-17 promoter | SEQ ID NO: 40 | soybean gb1-3-2 | SEQ ID NO: 31 |
| hsp17.5 promoter | SEQ ID NO: 41 | soybean gb1-3-2 | SEQ ID NO: 31 |
| hva22 promoter | SEQ ID NO: 42 | soybean gb1-3-2 | SEQ ID NO: 31 |
| ca4h promoter | SEQ ID NO: 43 | soybean gb1-3-2 | SEQ ID NO: 31 |
| hsp16.9 promoter | SEQ ID NO: 44 | soybean gb1-3-2 | SEQ ID NO: 31 |
| hsp22 promoter | SEQ ID NO: 45 | soybean gb1-3-2 | SEQ ID NO: 31 |
| rab-17 promoter | SEQ ID NO: 46 | soybean gb1-3-2 | SEQ ID NO: 31 |
| maize gb1 promoter | SEQ ID NO: 47 | soybean gb1-3-2 | SEQ ID NO: 31 |
| maize cvy-cik1 promoter | SEQ ID NO: 48 | soybean gb1-3-2 | SEQ ID NO: 31 |
| maize cvy-cik1 promoter | SEQ ID NO: 49 | soybean gb1-3-2 | SEQ ID NO: 31 |
| maize cvy-cik1 promoter | SEQ ID NO: 50 | soybean gb1-3-2 | SEQ ID NO: 31 |
| maize cvy-cik1 promoter | SEQ ID NO: 51 | soybean gb1-3-2 | SEQ ID NO: 31 |
| maize cvy-cik1 promoter | SEQ ID NO: 52 | soybean gb1-3-2 | SEQ ID NO: 31 |
| rice cvy-cik1 promoter | SEQ ID NO: 53 | soybean gb1-3-2 | SEQ ID NO: 31 |
| rtbv promoter | SEQ ID NO: 54 | soybean gb1-3-2 | SEQ ID NO: 31 |
| maize nas promoter | SEQ ID NO: 55 | soybean gb1-3-2 | SEQ ID NO: 31 |
| coix hrgp promoter | SEQ ID NO: 56 | soybean gb1-3-2 | SEQ ID NO: 31 |
| rice actin 1 promoter and intron | SEQ ID NO: 35 | barley gb1-3-1 | SEQ ID NO: 32 |
| hsp17.5 promoter | SEQ ID NO: 36 | barley gb1-3-1 | SEQ ID NO: 32 |
| hva22 promoter | SEQ ID NO: 37 | barley gb1-3-1 | SEQ ID NO: 32 |
| ca4h promoter | SEQ ID NO: 38 | barley gb1-3-1 | SEQ ID NO: 32 |

TABLE 2-continued

Coding sequence and promoter combinations for the expression of gb1 coding sequences.

| Promoter | Promoter sequence | gb1 | gb1 coding sequence |
|---|---|---|---|
| rab-17 promoter | SEQ ID NO: 39 | barley gb1-3-1 | SEQ ID NO: 32 |
| rab-17 promoter | SEQ ID NO: 40 | barley gb1-3-1 | SEQ ID NO: 32 |
| hsp17.5 promoter | SEQ ID NO: 41 | barley gb1-3-1 | SEQ ID NO: 32 |
| hva22 promoter | SEQ ID NO: 42 | barley gb1-3-1 | SEQ ID NO: 32 |
| ca4h promoter | SEQ ID NO: 43 | barley gb1-3-1 | SEQ ID NO: 32 |
| hsp16.9 promoter | SEQ ID NO: 44 | barley gb1-3-1 | SEQ ID NO: 32 |
| hsp22 promoter | SEQ ID NO: 45 | barley gb1-3-1 | SEQ ID NO: 32 |
| rab-17 promoter | SEQ ID NO: 46 | barley gb1-3-1 | SEQ ID NO: 32 |
| maize gb1 promoter | SEQ ID NO: 47 | barley gb1-3-1 | SEQ ID NO: 32 |
| maize cvy-cik1 promoter | SEQ ID NO: 48 | barley gb1-3-1 | SEQ ID NO: 32 |
| maize cvy-cik1 promoter | SEQ ID NO: 49 | barley gb1-3-1 | SEQ ID NO: 32 |
| maize cvy-cik1 promoter | SEQ ID NO: 50 | barley gb1-3-1 | SEQ ID NO: 32 |
| maize cvy-cik1 promoter | SEQ ID NO: 51 | barley gb1-3-1 | SEQ ID NO: 32 |
| maize cvy-cik1 promoter | SEQ ID NO: 52 | barley gb1-3-1 | SEQ ID NO: 32 |
| rice cvy-cik1 promoter | SEQ ID NO: 53 | barley gb1-3-1 | SEQ ID NO: 32 |
| rtbv promoter | SEQ ID NO: 54 | barley gb1-3-1 | SEQ ID NO: 32 |
| maize nas promoter | SEQ ID NO: 55 | barley gb1-3-1 | SEQ ID NO: 32 |
| coix hrgp promoter | SEQ ID NO: 56 | barley gb1-3-1 | SEQ ID NO: 32 |
| rice actin 1 promoter and intron | SEQ ID NO: 35 | rice gb1-3-1 | SEQ ID NO: 33 |
| hsp17.5 promoter | SEQ ID NO: 36 | rice gb1-3-1 | SEQ ID NO: 33 |
| hva22 promoter | SEQ ID NO: 37 | rice gb1-3-1 | SEQ ID NO: 33 |
| ca4h promoter | SEQ ID NO: 38 | rice gb1-3-1 | SEQ ID NO: 33 |
| rab-17 promoter | SEQ ID NO: 39 | rice gb1-3-1 | SEQ ID NO: 33 |
| rab-17 promoter | SEQ ID NO: 40 | rice gb1-3-1 | SEQ ID NO: 33 |
| hsp17.5 promoter | SEQ ID NO: 41 | rice gb1-3-1 | SEQ ID NO: 33 |
| hva22 promoter | SEQ ID NO: 42 | rice gb1-3-1 | SEQ ID NO: 33 |
| ca4h promoter | SEQ ID NO: 43 | rice gb1-3-1 | SEQ ID NO: 33 |
| hsp16.9 promoter | SEQ ID NO: 44 | rice gb1-3-1 | SEQ ID NO: 33 |
| hsp22 promoter | SEQ ID NO: 45 | rice gb1-3-1 | SEQ ID NO: 33 |
| rab-17 promoter | SEQ ID NO: 46 | rice gb1-3-1 | SEQ ID NO: 33 |
| maize gb1 promoter | SEQ ID NO: 47 | rice gb1-3-1 | SEQ ID NO: 33 |
| maize cvy-cik1 promoter | SEQ ID NO: 48 | rice gb1-3-1 | SEQ ID NO: 33 |
| maize cvy-cik1 promoter | SEQ ID NO: 49 | rice gb1-3-1 | SEQ ID NO: 33 |
| maize cvy-cik1 promoter | SEQ ID NO: 50 | rice gb1-3-1 | SEQ ID NO: 33 |
| maize cvy-cik1 promoter | SEQ ID NO: 51 | rice gb1-3-1 | SEQ ID NO: 33 |
| maize cvy-cik1 promoter | SEQ ID NO: 52 | rice gb1-3-1 | SEQ ID NO: 33 |
| rice cvy-cik1 promoter | SEQ ID NO: 53 | rice gb1-3-1 | SEQ ID NO: 33 |
| rtbv promoter | SEQ ID NO: 54 | rice gb1-3-1 | SEQ ID NO: 33 |
| maize nas promoter | SEQ ID NO: 55 | rice gb1-3-1 | SEQ ID NO: 33 |
| coix hrgp promoter | SEQ ID NO: 56 | rice gb1-3-1 | SEQ ID NO: 33 |
| rice actin 1 promoter and intron | SEQ ID NO: 35 | wheat gb1-3-1 | SEQ ID NO: 34 |
| hsp17.5 promoter | SEQ ID NO: 36 | wheat gb1-3-1 | SEQ ID NO: 34 |
| hva22 promoter | SEQ ID NO: 37 | wheat gb1-3-1 | SEQ ID NO: 34 |
| ca4h promoter | SEQ ID NO: 38 | wheat gb1-3-1 | SEQ ID NO: 34 |
| rab-17 promoter | SEQ ID NO: 39 | wheat gb1-3-1 | SEQ ID NO: 34 |
| rab-17 promoter | SEQ ID NO: 40 | wheat gb1-3-1 | SEQ ID NO: 34 |
| hsp17.5 promoter | SEQ ID NO: 41 | wheat gb1-3-1 | SEQ ID NO: 34 |
| hva22 promoter | SEQ ID NO: 42 | wheat gb1-3-1 | SEQ ID NO: 34 |
| ca4h promoter | SEQ ID NO: 43 | wheat gb1-3-1 | SEQ ID NO: 34 |
| hsp16.9 promoter | SEQ ID NO: 44 | wheat gb1-3-1 | SEQ ID NO: 34 |
| hsp22 promoter | SEQ ID NO: 45 | wheat gb1-3-1 | SEQ ID NO: 34 |
| rab-17 promoter | SEQ ID NO: 46 | wheat gb1-3-1 | SEQ ID NO: 34 |
| maize gb1 promoter | SEQ ID NO: 47 | wheat gb1-3-1 | SEQ ID NO: 34 |
| maize cvy-cik1 promoter | SEQ ID NO: 48 | wheat gb1-3-1 | SEQ ID NO: 34 |
| maize cvy-cik1 promoter | SEQ ID NO: 49 | wheat gb1-3-1 | SEQ ID NO: 34 |
| maize cvy-cik1 promoter | SEQ ID NO: 50 | wheat gb1-3-1 | SEQ ID NO: 34 |

TABLE 2-continued

Coding sequence and promoter combinations for the expression of gb1 coding sequences.

| Promoter | Promoter sequence | gb1 | gb1 coding sequence |
|---|---|---|---|
| maize cvy-cik1 promoter | SEQ ID NO: 51 | wheat gb1-3-1 | SEQ ID NO: 34 |
| maize cvy-cik1 promoter | SEQ ID NO: 52 | wheat gb1-3-1 | SEQ ID NO: 34 |
| rice cvy-cik1 promoter | SEQ ID NO: 53 | wheat gb1-3-1 | SEQ ID NO: 34 |
| rtbv promoter | SEQ ID NO: 54 | wheat gb1-3-1 | SEQ ID NO: 34 |
| maize nas promoter | SEQ ID NO: 55 | wheat gb1-3-1 | SEQ ID NO: 34 |
| coix hrgp promoter | SEQ ID NO: 56 | wheat gb1-3-1 | SEQ ID NO: 34 |

Transgenic plants produced with a water-deficit-inducible, cold inducible, other stress inducible or any other promoter operably linked to an exogenous gb1 coding sequence of the present invention (see for example, Table 2) are subjected to various growing conditions to demonstrate the effect of expressing a gb1 coding sequence in the transgenic plants. Plants are exposed to cold conditions, water-deficit conditions, heat, saline and other stresses in the field and under green house conditions. The plants are exposed to the stress condition for a period of time long enough and/or severe enough to induce the action of a stress-inducible promoter, e.g. withholding water for at least three days, before the collection of leaf tissue samples. Sample tissue is collected from transgenic plants expressing an exogenousg b1 coding sequence of the present invention for evaluation. Leaf tissue is collected from leaves of several ages (V2, V4, V6, V8 and V10) following water-deficit treatment or root tissue is collected at 12 hour intervals after a cold treatment. When collected tissue from the transgenic plant comprising and expressing an exogenous gb1 coding sequence described in Table 2 is analyzed for glycine-betaine, elevated levels of glycine-betaine compared to the non-transgenic maize line are measured, similar to elevated levels produced in the transgenic plant reported in the preceding Example 2 and increased stress-protection resulting from the expression of the gb1 coding sequence in the tissues is demonstrated.

Example 4

Tolerance to Water Deficit by Transgenic Plants and Seed

Transgenic maize and seed, prepared as described in Examples 2 and 3, are subjected to water-deficit conditions and examined for increased tolerance to water-deficit.

In a controlled environment such as a greenhouse, water-deficit is imposed upon the plants and seeds by germinating seed under water-deficit conditions, and imposing water-deficit conditions on seedlings and plants at various stage of development, such as at V2, V4, V6, V8 and V10. Water-deficit is induced by withholding or limiting water. Water-deficit is also induced by the application of saline and PEG solutions which induce water-deficit. In a less controlled environment, such as a field, water-deficit conditions are achieved by growing in a geographical location in which rainfall is usually limiting and by withholding irrigation.

Several parameters are measured to determine increased tolerance to water-deficit: plant height, leaf length, shoot mass, seed set, number of seed, yield, photosynthesis, turgor pressure, osmotic potential, leaf extension rate, and germination. In the practice of the current invention, maize plants and seeds expressing an exogenous gb1 coding sequence and producing enhanced glycine-betaine demonstrate increased tolerance to water-deficit compared to control plants lacking the transgene, e.g., a non-transgenic segregant, a plant treated with GB or a plant that naturally accumulates GB. Moreover, a water-deficit tolerant maize plant and seed expressing an exogenous gb1 coding sequence has improved yield similar to, or increased upon, yield inherent in a GB accumulator maize line.

Transgenic soybean, cotton, canola and tobacco plants and seed are prepared with similar DNA constructs as described for maize, and similar water deficit studies carried out as described for maize. As compared to control plants and control seed lacking the exogenous DNA constructs, transgenic soybean cotton, canola and tobacco plants and seed with increased glycine-betaine content show increased tolerance for water-deficit conditions.

Example 5

Tolerance to Cold by Transgenic Plants and Seed

Transgenic maize, prepared as described in Examples 2 and 3, are subjected to cold conditions and examined for increased tolerance to cold. Of particular interest is the ability of the seed of the transgenic maize to germinate under cold temperatures, to tolerate a period of cold temperature after germination, and the ability of a young seedling to tolerate a period of cold temperature.

Several parameters are measured to determine increased tolerance to cold such as measuring germination, plant height, leaf length, root length, root mass, shoot mass, chlorophyll fluorescence, and yield. In the practice of the current invention, transgenic maize plants and seed expressing an exogenous gb1 coding sequence and producing enhanced glycine-betaine demonstrate increased tolerance to cold conditions compared to control plants lacking the transgene, e.g., a non-transgenic segregant, a plant treated with GB or a plant that naturally accumulates GB. For example, a transgenic cold tolerant maize plant or seed expressing an exogenous gb1 coding sequence has improved yield similar to, or increased upon, yield inherent in a GB accumulator maize line.

Germination Under Cold Condition

Hybrid seeds were produced by crossing pMON78450 (FIG. 3) transgenic $R_2$ plants prepared in Example 2 with two different tester lines: FBLL which naturally accumulates glycine-betaine, or LH244 which is naturally a non-accumulator line. The hybrid seeds from several different transgenic events comprising the exogenous gb1 coding sequence from pMON78450, as well as non-transgenic negative segregant maize kernels, were germinated under cold conditions. One hundred kernels were tested for each transgenic event and non-transgenic negative segregant. Batches of ten kernels each were germinated in Petri dishes lined with moistened filter paper in a growth chamber at approximately 9.5-9.8° C. in constant darkness. Water was added to the plates throughout the test as necessary.

Each day, the number of seeds germinated per plate was counted. A seed was considered to be germinated when the root radicle reached 1 cm. At the end of the test, root tip tissue was sampled from a number of seedlings per event and metabolites were extracted in order to determine the levels of glycine-betaine. For glycine-betaine measurements, samples were lyophilized, ground to a fine powder and metabolites extracted into an ethanol-based extraction buffer supplemented with deuterated glycine-betaine as an internal standard metabolite. Samples were analyzed by liquid chromatography-mass spectrometry/mass spectrometry and the amount of glycine-betaine (in ppm) determined by analyzing the ratio of the deuterated and non-deuterated glycine-betaine in comparison to a standard curve.

A control experiment was also performed under non-cold conditions. Batches of ten kernels each were germinated in Petri dishes lined with moistened filter paper in a growth chamber set at 27° C. in constant darkness. Fifty kernels were tested for each transgenic event and non-transgenic negative segregant.

Three different calculations were used to analyze the cold germination data:

1. Germination Index: This is a calculation which takes into account the time required by a given set of seeds, e.g., the 100 kernels representing a transgenic event, to germinate relative to other sets of seeds in the test as well as the total number of seed which germinate in a given experiment. A higher germination index number indicates a faster germination time and better overall germination performance for a given set of seeds. The formula used is:

Germination index=$((T \times P1)+((T-1) \times P2)+((T-2) \times P3)+ \ldots +(1 \times PT))/T$ In which T=the total number of days of the test
P1, P2, P3, and PT=the percentage of seeds which germinated on that specific day of the test 2. Total Percent Germination: The percent of seeds which germinated for each set of seeds at the end of an experiment.

3. Days Until 50% Germination: This calculates the average number of days until half of the seeds being tested for a particular set of seeds have germinated. The model used to estimate the days to 50% germination is a three-parameter logistic model. This nonlinear model was fit using the statistical software package, JMP® (JMP®, version 5.1, 1989-2003 SAS Institute Inc. Cary, N.C.). The fitted model was found using an iterative optimization procedure.

Germination Under Non-Cold Condition Followed by Cold Condition: Early Seedling Test Seeds from a number of gb1 transgenic events and non-transgenic negative segregants were germinated on moistened vertical rolls of germination paper. Three rolls were set up for each selection, with 16 kernels used for each roll. For the cold assay, the seedlings were first germinated at about 23° C. for three days before being transferred to a chamber at a constant 12° C. for an additional 10 days. For the non-cold assay, seedlings were germinated in rolled germination paper at about 23° C. for five days. At the end of the test period, root and shoot length were determined for the seeds exposed to cold and non-cold conditions.

Germination Under Non-Cold Condition Followed by Cold Condition: Young Seedling Soil Test Seeds from a number of gb1 transgenic events and non-transgenic negative segregants were germinated in individual pots of soil at 23° C. until they reached the V1 stage for testing (about 10 days; 12 hour light/dark cycle). The young seedlings were then transferred to cold condition (about 8° C. during the light cycles, 5° C. in the dark cycles) for 8 days, after which they were transferred back to non-cold condition (about 23° C.) for recovery. On the fourth day of the cold treatment, the chlorophyll fluorescence of each of the young seedlings was measured. Three days after the young seedlings were returned to 23° C., two measurements were made: 1) leaf necrosis of each young seedling was estimated on the V2 leaf by visually estimating the percent of each V2 leaf which was still green at this stage and 2) the length of the V3 leaf (from soil to tip) was measured. This length was measured again at six days after recovery, to compare the growth rates after recovery for the transgenic and non-transgenic control young seedlings.

Tables 3 and 4 summarize the results of expressing an exogenous gb1 coding sequence having the sequence of SEQ ID NO:19 encoding a GB1 protein having an amino acid sequence of SEQ ID NO:1 which results in increased glycine-betaine on cold germination of transgenic hybrid maize seeds where one parent was a non-accumulating line (LH244; Table 3) or where one parent naturally accumulated glycine-betaine (FBLL; Table 4). The values for the Germination Index, Total Percent Germination and Days Until 50% Germination are reported as is the average amount of glycine-betaine accumulated by the transgenic or control negative segregant germinating root tip tissue.

The data indicate that of the eight gb1 transgenic events tested in the LH244 hybrid (Table 3), four events exhibited a statistically significant improvement in germination index and in total percent germination relative to the negative segregant seed. In addition, four events also demonstrated an improved germination time, as shown by the reduced number of days until 50% germination was achieved. In the early seedling test, the roots and shoots of the seedlings from one transgenic event were longer relative to the negative segregant, and in the young seedling soil test, the leaf length of one transgenic event was increased relative to the negative segregant. All events exhibiting an improvement in at least one cold germination, early seedling or young seedling characteristic accumulated at least 75 ppm glycine-betaine in the root tip tissue of the germinating seed. One event accumulating more than 75 ppm glycine-betaine did not exhibit an improvement in any of the measured parameters. On average, for all events in the LH244 hybrid plants, the improvement in germination index and total % germination in the cold were statistically significant at P<0.0015 and P<0.0017, respectively. The results from the non-cold condition germination test indicated that all of the seed used in the test were of good quality.

The data indicate that of the eight gb 1 transgenic events tested in the FBLL hybrid (Table 4), three events exhibited a statistically significant improvement in germination index as well as in germination time relative to the negative segregant seed. One event demonstrated an improved total percent germination relative to the negative segregant seed. In the early seedling test, the roots and/or shoots of the seedlings from three transgenic events were longer relative to the negative segregant, and in the young seedling soil test, the leaf length of one transgenic event was increased relative to the negative segregant. On average, for all events in the FBLL hybrid plants, the improvement in germination index and total % germination in the cold were statistically significant at P<0.0037 and P<0.1403, respectively. The results from the non-cold condition germination test indicate that all of the seed used in the test were of good quality.

The results reported in Tables 3 and 4 show that over-expression of the maize gb1 transgene, and resultant increase in glycine-betaine accumulation, increases the cold germination of the non-accumulator LH244 seeds to a greater degree than that of the naturally accumulating FBLL line in these tests.

TABLE 3

Effect of gb1 over-expression in LH244 (non-accumulating line)

| Event | Trans-gene[a] | ppm GB Avg[b] | Germination Index Avg[c] | Total % Germination Avg[c] | Days to 50% Germination Avg[c] |
|---|---|---|---|---|---|
| M44196 | POS | 151 | 27.81 | 77 | 16.7 |
| M44196 | neg | 2 | 41.78 | 98 | 15.6 |
| M44199 | POS | 269 | 41.77 | 96 | 15.3^ |
| M44199 | neg | 2 | 38.06 | 93 | 16.2 |
| M44202 | POS | 113 | 31.82**** | 89* | 16.8^ |
| M44202 | neg | 1 | 19.82 | 77 | 19.2 |
| M45434 | POS | 76 | 31.99 | 90 | 17.3^ |
| M45434 | neg | 2 | 27.74 | 85 | 18.1 |
| M45441 | POS | 48 | 29.91 | 90 | 18.0 |
| M45441 | neg | 2 | 32.36 | 94 | 17.3 |
| M45444 | POS | 181 | 25.19**** | 87*** | 18.8^ |
| M45444 | neg | 2 | 13.34 | 57 | 19.8 |
| M46403 | POS | 184 | 29.74**** | 82**** | 17.1 |
| M46403 | neg | 1 | 17.96 | 48 | 16.6 |
| M46411 | POS | 124 | 27.91* | 83* | 17.9 |
| M46411 | neg | 2 | 22.71 | 72 | 17.9 |
| Average | POS | | 31.2** | 87.2** | |
| Average | Neg | | 27 | 79.4 | |

[a]Pos = presence of the exogenous maize gb1 coding sequence (pMON78450; SEQ ID NO: 19); Neg = the absence of the gb1 transgenic coding sequence.
[b]Average is per 3 replicates of 3 pieces of root tissue measured under cold condition
[c]Average is per set of 100 kernels
*P < 0.06, positive improvement
**P < 0.01, positive improvement
***P < 0.001, positive improvement
****P < 0.0001, positive improvement
^high and low confidence limit values did not overlap and at least about 1 day of improvement

TABLE 4

Effect of gb1 over-expression in FBLL (accumulating line)

| Event | Trans-gene[a] | ppm gb Avg[b] | Germination Index Avg[c] | Total % Germination Avg[c] | Days to 50% Germination Avg[c] |
|---|---|---|---|---|---|
| M44196 | POS | 109 | 46.9** | 99 | 14.4^ |
| M44196 | neg | 12 | 40.5 | 99 | 15.7 |
| M44199 | POS | 204 | 39.9 | 97 | 15.5 |
| M44199 | neg | 3 | 43.7 | 100 | 15.4 |
| M44202 | POS | 114 | 46.4 | 98 | 14.4 |
| M44202 | neg | 4 | 43.4 | 95 | 14.8 |
| M45434 | POS | 95 | 45.6*** | 99* | 14.6^ |
| M45434 | neg | 2 | 39.4 | 94 | 15.6 |
| M45441 | POS | 45 | 44.1* | 96 | 14.8^ |
| M45441 | neg | 2 | 38.1 | 91 | 15.9 |
| M45444 | POS | 133 | 40.6 | 94 | 15.0 |
| M45444 | neg | 7 | 39.2 | 94 | 15.7 |
| M45445 | POS | 99 | 42.2 | 97 | 14.8 |
| M45445 | neg | 1 | 42.8 | 96 | 15.1 |
| M46403 | POS | 140 | 36.9 | 94 | 16 |
| M46403 | neg | 2 | 37.9 | 90 | 15.7 |
| Average | POS | | 42.5** | 96.8 | |
| Average | Neg | | 40.2 | 95.3 | |

[a]Pos = presence of the exogenous maize gb1 coding sequence (pMON78450; SEQ ID NO: 19); Neg = the absence of the gb1 transgenic coding sequence.
[b]Average is per 3 replicates of 3 pieces of root tissue measured under cold condition. Note that by the V2 stage, the non-transgenic FBLL line accumulated about 25-30 ppm GB compared to about 2-2.5 ppm for the non-transgenic LH244 line.
[c]Average is per set of 100 kernels
*P < 0.06, positive improvement
**P < 0.01, positive improvement
***P < 0.001, positive improvement
****P < 0.0001, positive improvement
^high and low confidence limit values did not overlap and at least about 1 day of improvement Transgenic soybean, cotton, canola and tobacco are prepared with similar DNA constructs as described for maize, and similar studies carried out as described for maize. As compared to plants lacking the exogenous DNA constructs, e.g., non-gb1 plants, transgenic soybean, cotton, canola and tobacco with increased glycine-betaine content show increased tolerance for cold conditions.

We claim:

1. A transgenic plant comprising in its genome an exogenous DNA comprising a promoter operably linked to a heterologous DNA, wherein said promoter exhibits promoter activity and comprises SEQ ID NO:56.

2. A DNA construct comprising a promoter operably linked to a heterologous DNA wherein said promoter comprises SEQ ID NO:56.

3. The transgenic plant of claim 1, wherein said plant is a plant selected from the group consisting of maize, soybean, rice, wheat, canola, cotton, sorghum, tobacco, sunflower, alfalfa, barley, millet, and turfgrass.

4. A seed of the transgenic plant of claim 1, wherein said seed comprises said exogenous DNA.

5. A seed of the transgenic plant of claim 3, wherein said seed comprises said exogenous DNA.

6. A transgenic plant cell comprising the DNA construct of claim 2.

* * * * *

SEQUENCE LISTING

<160> NUMBER OF SEQ ID NOS: 57

<210> SEQ ID NO 1
<211> LENGTH: 306
<212> TYPE: PRT
<213> ORGANISM: Zea mays

<400> SEQUENCE: 1

Met Ile Pro Tyr Ala Thr Ala Ala Glu Ala Glu Gly Ala Leu Gly Arg
1               5                   10                  15

Thr Met Thr Trp Ala Glu Thr Ala Trp Tyr Glu Tyr Ser Ala Val Met
            20                  25                  30

Pro Asp Ser Trp Leu His Cys His Thr Thr Phe Ile Leu Phe Val Ile
        35                  40                  45

Tyr Ser Ile Ala Pro Leu Pro Leu Leu Leu Glu Gln Phe Ala Pro
    50                  55                  60

-continued

```
Ser Val Val Leu Pro Tyr Lys Leu Gln Pro Arg Val Arg Leu Pro Pro
 65                  70                  75                  80

Ala Ala Ser Leu Ser Cys Tyr Met Asp Ala Cys Ile Phe Pro Leu
             85                  90                  95

Ala Val Gly Leu Gln Phe Val Ser Tyr Pro Ala Val Ala Lys Ile Leu
            100                 105                 110

Arg Thr Arg Met Gly Leu Pro Leu Pro Ser Val Arg Glu Thr Ile Ala
        115                 120                 125

Gln Leu Val Val Tyr Ser Leu Val Glu Asp Tyr Leu Ser Tyr Trp Met
130                 135                 140

His Arg Leu Leu His Thr Gln Trp Cys Tyr Glu Lys Ile His Arg Val
145                 150                 155                 160

His His Glu Phe Thr Ala Pro Thr Gly Phe Ala Met Ser Tyr Ser His
                165                 170                 175

Trp Ala Glu Asn Val Val Leu Ser Ile Pro Ala Leu Ala Gly Pro Val
            180                 185                 190

Leu Val Pro Cys His Val Thr Thr Gln Trp Leu Trp Phe Ser Ile Arg
        195                 200                 205

Leu Ile Glu Gly Ile Asn Thr His Ser Gly Tyr His Phe Pro Phe Ser
210                 215                 220

Pro Cys Arg Leu Ile Pro Phe Tyr Gly Ala Ala Tyr His Asp Tyr
225                 230                 235                 240

His His Tyr Ala Gly Gly Arg Ser Gln Ser Asn Phe Ala Pro Leu Phe
                245                 250                 255

Thr Tyr Cys Asp Tyr Leu Tyr Arg Thr Asp Lys Gly Tyr Arg Tyr His
            260                 265                 270

Lys Leu Lys Gln Glu Lys Leu Lys Ser Leu Ala Glu Asn Ser Ala Asp
        275                 280                 285

Lys Gly Gly Asn Tyr Ser Phe Asp Glu Gly Lys Asn Arg Tyr Phe
290                 295                 300

Cys Ala
305
```

<210> SEQ ID NO 2
<211> LENGTH: 293
<212> TYPE: PRT
<213> ORGANISM: Zea mays

<400> SEQUENCE: 2

```
Met Met Pro Tyr Gly Thr Ala Ala Glu Ala Glu Ala Ala Leu Gly Arg
 1               5                  10                  15

Ser Met Thr Trp Ala Glu Ala Leu Trp Phe Arg Tyr Ser Ala Gly Met
                20                  25                  30

Pro Asp Leu Cys Leu Thr Trp His Val Ser Leu Val Tyr Leu Val Leu
             35                  40                  45

Tyr Ala Leu Val Pro Leu Pro Val Met Val Ile Gln Lys Leu Ala Pro
 50                  55                  60

Gly Tyr Ala Leu Arg His Lys Leu Gln Pro Gly Val Pro Glu Pro Ser
 65                  70                  75                  80

Pro Val Ser Thr Tyr Val Glu Tyr Ile Arg Asp Ser Arg Gly Val Thr
                 85                  90                  95

Leu Ala Ala Leu Gly Pro Phe Pro Leu Ile Tyr Ser Ile Ala Phe Lys
            100                 105                 110

Leu Phe Gly Val Arg Thr Gly Leu Pro Leu Pro Ser Val Trp Glu Thr
        115                 120                 125
```

```
Ala Thr His Leu Ala Val Tyr Ser Leu Val Glu Asp Tyr Thr Ser Tyr
        130                 135                 140

Trp Leu His Arg Phe Leu His Thr Arg Trp Gly Tyr Glu Lys Ile His
145                 150                 155                 160

Arg Val His His Glu Lys Thr Ala Pro Ser Gly Phe Ala Ala Tyr
                165                 170                 175

Ala Thr Gly Thr Glu Leu Ser Leu Tyr Leu Thr Thr Leu Phe Leu Gly
                180                 185                 190

Pro Ala Ile Val Pro Ser His Val Thr Thr His Trp Leu Leu Phe Ser
        195                 200                 205

Ile Arg Ile Met Glu Ala Phe Asp Thr His Ser Gly Tyr His Phe Pro
210                 215                 220

Phe Ser Leu Ala Arg Phe Ile Pro Phe Tyr Gly Gly Ala Glu Phe His
225                 230                 235                 240

Asp Tyr His His Tyr Ala Gly Glu Lys Thr Arg Ser Asn Phe Ser Ser
                245                 250                 255

Val Phe Thr Tyr Cys Asp Tyr Ile Tyr Gly Thr Asn Lys Gly Tyr Met
                260                 265                 270

Tyr His Lys Arg Ser Leu Ala Glu Leu Lys Thr Lys Gly Ala Glu His
            275                 280                 285

Ser Gly Lys Glu Asp
    290

<210> SEQ ID NO 3
<211> LENGTH: 284
<212> TYPE: PRT
<213> ORGANISM: Oryza sativa

<400> SEQUENCE: 3

Met Leu Pro Tyr Ala Thr Ala Ala Glu Ala Glu Ala Ala Val Gly Arg
1               5                   10                  15

Gly Leu Thr Trp Ala Glu Ala Ala Trp Phe Arg Tyr Ser Ala Ala Ile
                20                  25                  30

Pro Asp Tyr Cys Leu Tyr Cys His Asn Val Pro Ile Leu Leu Leu Val
            35                  40                  45

Tyr Thr Leu Ala Pro Leu Pro Leu Ala Leu Leu Glu Leu Arg Arg His
    50                  55                  60

Leu Pro Leu Pro His Lys Leu Gln Pro Gly Val Arg His Pro Pro Ala
65                  70                  75                  80

Ala Phe Leu Arg Cys Tyr Ala Ala Thr Ala Arg Val Leu Leu Leu Ala
                85                  90                  95

Val Gly Pro Val Gln Leu Ala Ser Phe Pro Ala Val Arg Ala Val Gly
                100                 105                 110

Ile Arg Thr Gly Leu Pro Leu Pro Ser Ala Gly Glu Thr Ala Ala Gln
            115                 120                 125

Val Ala Val Tyr Leu Leu Val Glu Asp Tyr Leu Gly Tyr Trp Ile His
        130                 135                 140

Arg Leu Leu His Thr Pro Trp Ala Tyr His His Ile His Arg Val His
145                 150                 155                 160

His Glu Phe Thr Ala Pro Met Gly Tyr Ala Ala Pro Tyr Ala His Trp
                165                 170                 175

Ala Glu Ile Leu Ile Leu Gly Phe Pro Ala Phe Ala Gly Pro Ala Ile
                180                 185                 190

Val Pro Cys His Met Thr Thr Phe Trp Leu Trp Phe Val Leu Arg His
        195                 200                 205
```

-continued

```
Leu Glu Ala Ile His Ile His Ser Gly Phe Lys Leu Pro Phe Asp Pro
        210                 215                 220

Thr Lys Tyr Ile Pro Leu Tyr Gly Gly Val Glu Tyr His Asp Tyr His
225                 230                 235                 240

His Phe Val Gly Gly His Ser Gln Ser Asn Phe Ser Val Phe Thr
                245                 250                 255

Phe Cys Asp Tyr Ile Tyr Gly Thr Asp Arg Gly Tyr Arg Tyr His Lys
            260                 265                 270

Ala Ser Leu Ser Lys Met Arg Ile Phe Val Arg Ala
        275                 280

<210> SEQ ID NO 4
<211> LENGTH: 301
<212> TYPE: PRT
<213> ORGANISM: Hordeum vulgare
<220> FEATURE:
<221> NAME/KEY: misc_feature
<222> LOCATION: (185)..(185)
<223> OTHER INFORMATION: Xaa can be any naturally occurring amino acid

<400> SEQUENCE: 4

Met Leu Pro Tyr Ala Thr Thr Gly Asp Ala Glu Ala Ala Leu Gly Arg
1               5                   10                  15

Ala Leu Thr Trp Ala Glu Ala Ala Trp Leu Arg Tyr Ser Ala Ser Val
            20                  25                  30

Pro Asp Arg Tyr Leu His Trp Pro Asn Ile Ala Ile Thr Leu Val Val
        35                  40                  45

Tyr Thr Leu Ala Pro Leu Pro Leu Ala Leu Phe Asp Leu Ala Ala Pro
50                  55                  60

Ala Val Ala Ala Pro Tyr Lys Leu Gln Pro Lys Val Gln His Pro Pro
65                  70                  75                  80

Ala Thr Phe Phe Arg Cys Tyr Met Asp Ala Val Arg Val Ser Leu Leu
                85                  90                  95

Ile Ile Gly Pro Tyr Gln Leu Ile Ser Tyr Pro Ala Ala Lys Ile Met
            100                 105                 110

Asp Ile Arg Thr Gly Leu Pro Leu Pro Ser Met Gly Glu Ile Ala Ala
        115                 120                 125

Gln Leu Thr Val Tyr Phe Leu Val Glu Asp Tyr Leu Asn Tyr Trp Leu
130                 135                 140

His Arg Leu Leu His Thr Lys Trp Cys Tyr Glu Lys Ile His His Val
145                 150                 155                 160

His His Glu Phe Thr Ala Pro Met Ala Tyr Ala Ala Trp Tyr Gly His
                165                 170                 175

Trp Ala Glu Met Leu Ile Leu Ala Xaa Pro Ser Leu Ala Gly Pro Ala
            180                 185                 190

Leu Val Pro Cys His Val Thr Thr Leu Trp Ile Trp Phe Ala Ala Arg
        195                 200                 205

Leu Val Glu Ser Leu Asn Ile His Ser Gly Phe Lys Leu Pro Phe Asn
210                 215                 220

Ala Glu Lys Tyr Ile Pro Phe Tyr Gly Ala Glu His His Asp Tyr
225                 230                 235                 240

His His Tyr Ile Gly Gly Gln Ser Lys Ser Asn Phe Ala Pro Val Phe
                245                 250                 255

Thr Tyr Cys Asp Tyr Ile Tyr Gly Thr Asp Lys Gly Tyr Arg Tyr His
            260                 265                 270

Lys Ala Thr Leu Ala Lys Leu Lys Glu Leu Ala Gly Asn Glu Val Gln
        275                 280                 285
```

```
Lys Gly Val Asp Asn Gly Phe Asn Ser Gly Lys Gln Glu
    290                 295                 300
```

<210> SEQ ID NO 5
<211> LENGTH: 301
<212> TYPE: PRT
<213> ORGANISM: Zea mays

<400> SEQUENCE: 5

```
Met Leu Pro Tyr Ala Thr Ala Glu Ala Glu Ala Leu Gly Arg
1               5                   10                  15

Pro Met Thr Pro Ala Glu Ala Leu Trp Phe Arg Tyr Thr Ala Gly Val
            20                  25                  30

Ser Asp Tyr His Leu Tyr Cys Cys Asn Ile Leu Phe Leu Phe Val Val
                35                  40                  45

Phe Thr Val Ala Pro Leu Pro Ile Ala Leu Leu Glu Leu Arg Ala Pro
    50                  55                      60

Ala Ala Val Ser Pro Tyr Lys Leu Gln Pro Arg Val Arg Leu Ser Arg
65                  70                  75                  80

Ala Glu Phe Val Arg Cys Tyr Lys Asp Val Leu Arg Ile Phe Phe Leu
                85                  90                  95

Val Ile Gly Pro Leu Gln Leu Val Ser Tyr Pro Ala Val Lys Phe Val
            100                 105                 110

Gly Ile His Thr Lys Leu Pro Leu Pro Ser Leu Ala Glu Leu Ala Ala
        115                 120                 125

Gln Leu Leu Val Tyr Phe Leu Val Glu Asp Tyr Leu Asn Tyr Trp Ile
    130                 135                 140

His Arg Phe Leu His Gly Glu Trp Gly Tyr Gln Asn Ile His Arg Val
145                 150                 155                 160

His His Glu Phe Thr Ala Pro Ile Gly Phe Ala Ala Pro Tyr Ala His
                165                 170                 175

Trp Ala Glu Val Leu Ile Leu Gly Ile Pro Ser Phe Val Gly Pro Ala
            180                 185                 190

Ile Val Pro Gly His Met Ile Thr Phe Trp Leu Trp Ile Ile Leu Arg
        195                 200                 205

Gln Val Glu Ala Ile Glu Thr His Ser Gly Phe Asp Phe Pro Phe Thr
    210                 215                 220

Pro Thr Lys Tyr Ile Pro Phe Tyr Gly Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Leu Tyr Gly Thr Asp Lys Gly Tyr Arg Phe His
            260                 265                 270

Lys Thr Tyr Leu Ala Lys Leu Lys Asp Leu Gly His Asn Asp Gly Gln
        275                 280                 285

Lys Gly Asp Gly Ser Gly Pro Ser Tyr Val Lys Leu Asp
    290                 295                 300
```

<210> SEQ ID NO 6
<211> LENGTH: 299
<212> TYPE: PRT
<213> ORGANISM: Allium porrum

<400> SEQUENCE: 6

```
Met Ile Pro Tyr Pro Ser Leu Thr Ala Ala Glu Ala Ala Leu Asn Arg
1               5                   10                  15
```

```
Pro Leu Thr Tyr Ala Glu Thr Ile Trp Phe Asn Tyr Ser Ala Thr Ile
            20                  25                  30

Pro Asp Pro Leu Leu Tyr Tyr His Asn Thr Ile Phe Leu Phe Val Ile
        35                  40                  45

Phe Thr Leu Val Pro Leu Pro Leu Ala Leu Leu Glu Leu Tyr Trp Pro
 50                  55                  60

Ser Val Leu Lys Pro Phe Lys Ile Gln Pro Lys Val Tyr Leu Ser Lys
65                  70                  75                  80

Ser Glu Phe Leu Glu Cys Tyr Lys Asn Val Ile Lys Val Phe Phe Leu
                85                  90                  95

Val Val Cys Pro Leu Gln Leu Ser Tyr Pro Thr Val Lys Phe Val
            100                 105                 110

Gly Ile Arg Thr Gly Leu Pro Leu Pro Ser Val Trp Glu Val Ala Ser
            115                 120                 125

Gln Leu Ala Val Tyr Phe Leu Leu Glu Asp Phe Gly Asn Tyr Trp Ile
        130                 135                 140

His Arg Trp Leu His Gly Lys Trp Gly Tyr Glu Lys Ile His Lys Val
145                 150                 155                 160

His His Glu Tyr Thr Ala Pro Ile Gly Phe Ala Ala Pro Tyr Ala His
                165                 170                 175

Trp Ala Glu Val Leu Ile Leu Gly Ile Pro Ser Phe Leu Gly Pro Ala
            180                 185                 190

Ile Val Pro Gly His Met Ile Thr Leu Trp Leu Trp Ile Ala Leu Arg
        195                 200                 205

Gln Ile Glu Ala Leu Asp Thr His Ser Gly Tyr Asp Phe Pro Leu Ser
210                 215                 220

Phe Thr Lys Phe Ile Pro Phe Tyr Gly Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Val Tyr Gly Thr Asp Lys Gly Tyr Arg Tyr Arg
            260                 265                 270

Lys Ala Cys Leu Ser Met Met Lys Glu Glu Ser Glu Asn Gln Asn Gly
        275                 280                 285

Val Glu Asn Ser Phe Gln Asn Gln Lys Ser Asp
    290                 295

<210> SEQ ID NO 7
<211> LENGTH: 298
<212> TYPE: PRT
<213> ORGANISM: Arabidopsis thaliana

<400> SEQUENCE: 7

Met Ile Pro Tyr Ala Thr Val Glu Glu Ala Ser Ile Ala Leu Gly Arg
1               5                   10                  15

Asn Leu Thr Arg Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Val
        35                  40                  45

Phe Ser Leu Val Pro Leu Pro Leu Val Phe Val Glu Leu Ala Arg Ser
 50                  55                  60

Ala Ser Gly Leu Phe Asn Arg Tyr Lys Ile Gln Pro Lys Val Asn Tyr
65                  70                  75                  80

Ser Leu Ser Asp Met Phe Lys Cys Tyr Lys Asp Val Met Thr Met Phe
                85                  90                  95
```

```
Ile Leu Val Val Gly Pro Leu Gln Leu Val Ser Tyr Pro Ser Ile Gln
                100                 105                 110

Met Ile Glu Ile Arg Ser Gly Leu Pro Leu Pro Thr Ile Thr Glu Met
            115                 120                 125

Leu Ser Gln Leu Val Val Tyr Phe Leu Ile Glu Asp Tyr Thr Asn Tyr
        130                 135                 140

Trp Val His Arg Phe Phe His Ser Lys Trp Gly Tyr Asp Lys Ile His
145                 150                 155                 160

Arg Val His His Glu Tyr Thr Ala Pro Ile Gly Tyr Ala Ala Pro Tyr
                165                 170                 175

Ala His Trp Ala Glu Val Leu Leu Gly Ile Pro Thr Phe Met Gly
            180                 185                 190

Pro Ala Ile Ala Pro Gly His Met Ile Thr Phe Trp Leu Trp Ile Ala
        195                 200                 205

Leu Arg Gln Met Glu Ala Ile Glu Thr His Ser Gly Tyr Asp Phe Pro
210                 215                 220

Trp Ser Pro Thr Lys Tyr Ile Pro Phe Tyr Gly Ala Glu Tyr His
225                 230                 235                 240

Asp Tyr His His Tyr Val Gly Gly Gln Ser Gln Ser Asn Phe Ala Ser
                245                 250                 255

Val Phe Thr Tyr Cys Asp Tyr Ile Tyr Gly Thr Asp Lys Gly Tyr Arg
            260                 265                 270

Phe Gln Lys Lys Leu Leu Glu Gln Ile Lys Glu Ser Ser Lys Lys Ser
        275                 280                 285

Asn Lys His Asn Gly Gly Ile Lys Ser Asp
290                 295

<210> SEQ ID NO 8
<211> LENGTH: 297
<212> TYPE: PRT
<213> ORGANISM: Arabidopsis thaliana

<400> SEQUENCE: 8

Met Ile Pro Tyr Ala Thr Ile Glu Glu Ala Ser Ile Ala Leu Ser Arg
1               5                   10                  15

Asn Leu Thr Trp Leu Glu Thr Leu Trp Phe Tyr Ser Ala Thr Lys
            20                  25                  30

Ser Asp Tyr Tyr Leu Tyr Cys His Asn Ile Leu Phe Leu Phe Leu Ile
        35                  40                  45

Phe Ser Leu Val Pro Leu Pro Leu Val Phe Ile Glu Ser Ser Gln Ser
    50                  55                  60

Thr Ser Asp Leu Phe Asn Arg Tyr Lys Ile Gln Pro Lys Val Lys Asn
65                  70                  75                  80

Ser Phe Ser Ser Met Phe Lys Cys Tyr Lys Asp Val Met Lys Met Phe
                85                  90                  95

Ile Leu Val Val Gly Pro Leu Gln Leu Val Ser Tyr Pro Ser Ile Gln
                100                 105                 110

Val Asp Phe Val Phe Arg Val Leu Lys Gln Met Ile Glu Ile Arg Ser
            115                 120                 125

Gly Leu Pro Leu Pro Ser Cys Met Glu Ile Val Ala Gln Leu Val Val
        130                 135                 140

Tyr Phe Leu Val Glu Asp Tyr Thr Asn Tyr Trp Val His Arg Phe Phe
145                 150                 155                 160

His Cys Lys Trp Gly Tyr Glu Lys Phe His His Ile His Glu Tyr
                165                 170                 175
```

```
Thr Ala Pro Ile Gly Tyr Ala Ala Pro Tyr Ala His Trp Ala Glu Val
            180                 185                 190

Leu Leu Leu Gly Ile Pro Thr Phe Leu Gly Pro Ala Ile Ala Pro Gly
            195                 200                 205

His Met Ile Thr Phe Trp Leu Trp Ile Ala Leu Arg Gln Ile Glu Ala
210                 215                 220

Ile Glu Thr His Ser Gly Tyr Asp Phe Pro Trp Ser Leu Thr Lys Tyr
225                 230                 235                 240

Ile Pro Phe Tyr Gly Ala Glu Tyr His Asp Tyr His His Tyr Val
                245                 250                 255

Gly Gly Gln Ser Gln Ser Asn Phe Ala Ser Val Phe Thr Tyr Cys Asp
            260                 265                 270

Tyr Ile Tyr Gly Thr Asp Lys Gly Tyr Arg Phe Gln Lys Lys Leu Leu
            275                 280                 285

Gln Gln Val Asn Lys Tyr Ser Ile Asn
        290                 295

<210> SEQ ID NO 9
<211> LENGTH: 291
<212> TYPE: PRT
<213> ORGANISM: Arabidopsis thaliana

<400> SEQUENCE: 9

Met Ile Pro Tyr Pro Thr Val Glu Asp Ala Ser Val Ala Leu Gly Arg
1               5                   10                  15

Asn Leu Thr Trp Phe Glu Thr Val Trp Phe Asp Tyr Ser Ala Thr Lys
            20                  25                  30

Ser Asn Phe His Val Tyr Cys His Thr Ile Leu Val Leu Phe Leu Val
        35                  40                  45

Phe Ser Leu Ala Pro Phe Pro Leu Val Ile Val Glu Trp Thr Gly Trp
50                  55                  60

Phe Asp Gln Phe Lys Ile Gln Lys Lys Val Lys Tyr Ser Leu Ser Asp
65                  70                  75                  80

Met Phe Gln Cys Tyr Lys Glu Val Met Lys Leu Phe Leu Leu Val Val
                85                  90                  95

Gly Thr Leu Gln Ile Val Ser Tyr Pro Ser Ile Gln Met Val Gly Ile
            100                 105                 110

Arg Ser Gly Leu Pro Leu Pro Ser Leu Met Glu Ile Val Ala Gln Leu
            115                 120                 125

Val Val Tyr Phe Leu Ile Glu Asp Tyr Thr Asn Tyr Trp Ile His Arg
        130                 135                 140

Trp Met His Cys Lys Trp Gly Tyr Glu Lys Ile His Arg Ile His His
145                 150                 155                 160

Glu Tyr Thr Ser Pro Ile Gly Tyr Ala Ser Pro Tyr Ala His Trp Ala
                165                 170                 175

Glu Ile Leu Ile Leu Gly Ile Pro Thr Phe Leu Gly Pro Ala Ile Ala
            180                 185                 190

Pro Gly His Ile Met Thr Phe Trp Leu Trp Ile Ser Leu Arg Gln Phe
            195                 200                 205

Glu Ala Ile Glu Thr His Ser Gly Tyr Asp Phe Pro Trp Ser Val Thr
210                 215                 220

Lys Leu Ile Pro Phe Tyr Gly Gly Pro Glu Tyr His Asp Tyr His His
225                 230                 235                 240

Tyr Val Gly Gly Gln Ser Gln Ser Asn Phe Ala Ser Val Phe Thr Tyr
                245                 250                 255
```

```
Cys Asp Tyr Ile Tyr Gly Thr Asp Lys Gly Tyr Arg Ile His Lys Lys
            260                 265                 270

Leu Leu His His Gln Ile Lys Glu Glu Ala Glu Lys Arg Val Arg
        275                 280                 285

Lys His Asp
    290

<210> SEQ ID NO 10
<211> LENGTH: 299
<212> TYPE: PRT
<213> ORGANISM: Arabidopsis thaliana

<400> SEQUENCE: 10

Met Ile Pro Tyr Ala Thr Ile Glu Glu Ala Ser Ile Ala Leu Ser Arg
1               5                   10                  15

Asn Leu Thr Trp Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Ile
        35                  40                  45

Phe Ser Leu Val Pro Leu Pro Leu Val Leu Ile Glu Ser Ala Gln Ser
50                  55                  60

Thr Ser Asp Leu Phe Asn Arg Tyr Lys Ile Gln Pro Lys Val Lys Asn
65                  70                  75                  80

Ser Phe Ser Ser Met Leu Lys Cys Tyr Lys Asp Val Met Lys Met Phe
                85                  90                  95

Ile Leu Val Val Gly Pro Leu Gln Leu Val Ser Tyr Pro Ser Ile Gln
            100                 105                 110

Met Ile Glu Ile Arg Ser Gly Leu Pro Leu Pro Ser Cys Met Glu Ile
        115                 120                 125

Val Ala Gln Phe Val Val Tyr Phe Leu Val Glu Asp Tyr Thr Asn Tyr
130                 135                 140

Trp Val His Arg Phe Phe His Cys Lys Trp Gly Tyr Glu Lys Phe His
145                 150                 155                 160

His Ile His His Glu Tyr Thr Ala Pro Ile Gly Tyr Ala Ala Pro Tyr
                165                 170                 175

Ala His Trp Ala Glu Val Leu Leu Leu Gly Ile Pro Thr Phe Leu Gly
            180                 185                 190

Pro Ala Ile Ala Pro Gly His Met Ile Thr Phe Trp Leu Trp Ile Ala
        195                 200                 205

Leu Arg Gln Ile Glu Ala Ile Glu Thr His Ser Gly Tyr Asp Phe Pro
210                 215                 220

Trp Ser Leu Thr Lys Tyr Ile Pro Phe Tyr Gly Gly Ala Glu Tyr His
225                 230                 235                 240

Asp Tyr His His Tyr Val Gly Gly Gln Ser Gln Ser Asn Phe Ala Ser
                245                 250                 255

Val Phe Thr Tyr Cys Asp Tyr Ile Tyr Gly Thr Asp Lys Gly Tyr Arg
            260                 265                 270

Phe Gln Lys Lys Leu Leu Gln Gln Met Lys Glu Lys Ser Lys Lys Ser
        275                 280                 285

Asn Lys Leu Val Asn Gly Gly Glu Lys Phe Asp
    290                 295

<210> SEQ ID NO 11
<211> LENGTH: 298
<212> TYPE: PRT
<213> ORGANISM: Brassica napus
```

```
<400> SEQUENCE: 11

Met Ile Pro Tyr Ala Thr Ile Glu Glu Ala Ser Leu Ala Leu Gly Arg
1               5                   10                  15

Asn Leu Thr Thr Leu Glu Thr Leu Trp Phe Asp Tyr Ser Ala Thr Lys
            20                  25                  30

Ser Asp Tyr Tyr Leu Tyr Cys His Asn Ile Leu Phe Leu Phe Leu Ile
        35                  40                  45

Phe Ser Leu Val Pro Leu Pro Leu Val Phe Val Glu Leu Ala Arg Ser
50                  55                  60

Ala Ser Gly Trp Phe Asp Arg Tyr Lys Ile Gln Pro Lys Val Lys Asn
65                  70                  75                  80

Ser Phe Ser Asp Met Phe Arg Cys Tyr Arg Asp Val Met Lys Met Phe
                85                  90                  95

Ile Leu Val Val Gly Pro Leu Gln Leu Val Ser Tyr Pro Ser Ile Gln
            100                 105                 110

Met Ile Glu Ile Arg Ser Gly Leu Pro Leu Pro Ser Phe Gly Glu Ile
        115                 120                 125

Ala Ala Gln Leu Val Val Tyr Phe Leu Val Glu Asp Tyr Thr Asn Tyr
130                 135                 140

Trp Val His Arg Phe Phe His Ser Lys Trp Gly Tyr Glu Lys Ile His
145                 150                 155                 160

His Ile His His Glu Tyr Thr Ala Pro Ile Gly Tyr Ala Ala Pro Tyr
                165                 170                 175

Ala His Trp Ala Glu Val Leu Leu Leu Gly Val Pro Thr Phe Leu Gly
            180                 185                 190

Pro Ala Ile Ala Pro Gly His Met Ile Thr Phe Trp Leu Trp Ile Ala
        195                 200                 205

Leu Arg Gln Ile Glu Ala Ile Glu Thr His Ser Gly Tyr Asp Phe Pro
210                 215                 220

Trp Thr Leu Thr Lys Phe Ile Pro Phe Tyr Gly Gly Ala Glu Tyr His
225                 230                 235                 240

Asp Tyr His His Tyr Val Gly Gly Gln Ser Gln Ser Asn Phe Ala Ser
                245                 250                 255

Val Phe Thr Tyr Cys Asp Tyr Ile Tyr Gly Thr Asp Lys Gly Tyr Arg
            260                 265                 270

Phe Gln Lys Lys Phe Leu Gln Gln Ile Lys Gln Glu Ser Lys Lys Ser
        275                 280                 285

Asn Met Gln Asn Gly Gly Asp Lys Leu Asp
290                 295

<210> SEQ ID NO 12
<211> LENGTH: 297
<212> TYPE: PRT
<213> ORGANISM: Glycine max

<400> SEQUENCE: 12

Met Leu Pro Tyr Ala Ser Ile Pro Glu Ala Val Ala Ala Leu Gly Arg
1               5                   10                  15

Asn Leu Thr Phe Ala Glu Thr Leu Trp Phe Asn Tyr Ser Ala Ala Lys
            20                  25                  30

Ser Asp Tyr Phe Leu Tyr Cys His Asn Ile Leu Phe Leu Phe Leu Val
        35                  40                  45

Phe Ser Leu Val Pro Leu Pro Leu Val Phe Leu Glu Phe Lys Arg Phe
50                  55                  60

Ser Phe Val Ser Ser His Lys Ile Gln Pro Lys Val Arg Leu Ser Leu
```

-continued

```
                65                  70                  75                  80
Ala Glu Thr Phe Lys Cys Tyr Lys Asp Val Met Arg Met Phe Phe Leu
                    85                  90                  95
Val Val Gly Pro Leu Gln Leu Ile Ser Tyr Pro Ser Ile Gln Met Ile
                    100                 105                 110
Gly Ile Arg Thr Gly Leu Pro Leu Pro Ser Trp Arg Glu Ile Leu Ser
                    115                 120                 125
Gln Leu Leu Val Tyr Phe Leu Val Glu Asp Tyr Thr Asn Tyr Trp Ile
            130                 135                 140
His Arg Phe Leu His Asn Asp Trp Gly Tyr Glu Lys Ile His Arg Val
145                 150                 155                 160
His His Glu Tyr His Ala Pro Ile Gly Phe Ala Ala Pro Tyr Ala His
                    165                 170                 175
Trp Ala Glu Ile Leu Ile Leu Gly Ile Pro Ser Phe Leu Gly Pro Ala
                    180                 185                 190
Met Val Pro Gly His Ile Ile Thr Phe Trp Leu Trp Ile Ala Leu Arg
                    195                 200                 205
Gln Ile Glu Ala Ile Asp Thr His Ser Gly Tyr Asp Phe Pro Arg Ser
            210                 215                 220
Ile Thr Lys Tyr Ile Pro Phe Tyr Gly Gly Ala Glu Tyr His Asp Tyr
225                 230                 235                 240
His His Tyr Val Gly Arg Gln Ser Gln Ser Asn Phe Ala Ser Val Phe
                    245                 250                 255
Thr Tyr Cys Asp Tyr Ile Tyr Gly Thr Asp Lys Gly Tyr Arg Tyr Gln
                    260                 265                 270
Lys Lys Ile Leu Gln Lys Leu Lys Glu Glu Leu Ala Asn Gly Val Glu
            275                 280                 285
Gln Asn Gly Gly Leu Tyr Lys Thr Asp
        290                 295
```

<210> SEQ ID NO 13
<211> LENGTH: 254
<212> TYPE: PRT
<213> ORGANISM: Glycine max
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid

<400> SEQUENCE: 13

```
Met Leu Pro Tyr His Thr Leu Glu Gly Ala Gln Val Ala Leu Gly Arg
1               5                   10                  15
Gly Leu Thr Leu Ala Glu Thr Ile Trp Phe Lys Tyr Ser Ala Asn Lys
                    20                  25                  30
Pro Asp Phe Val Leu His Cys His Asn Thr Leu Phe Leu Cys Leu Phe
                    35                  40                  45
Tyr Ser Ile Ala Pro Ile Pro Phe Val Leu Met Glu Leu Ser Gly Tyr
            50                  55                  60
Glu Lys Leu Asn Lys His Lys Ile Gln Pro Ser Val Lys Arg Ser Phe
65                  70                  75                  80
Lys Glu Met Phe Lys Cys Tyr Lys Asp Val Met Glu Thr Phe Val Ile
                    85                  90                  95
Ala Val Ser Pro Leu Gln Ile Ile Ser Tyr Pro Thr Ile Lys Trp Ile
                    100                 105                 110
```

```
Gly Ile Arg Thr Gly Leu Ser Leu Pro Ser Gly Trp Glu Leu Phe Trp
            115                 120                 125

Gln Leu Phe Ile Tyr Phe Val Ile Glu Asp Phe Ser Asn Tyr Trp Ile
130                 135                 140

His Arg Met Leu His Cys Lys Trp Ala Phe Glu Lys Ile His Lys Val
145                 150                 155                 160

His His Glu Tyr Val Ala Pro Ile Gly Leu Ser Ala Pro Tyr Ala His
                165                 170                 175

Trp Ala Glu Ile Ile Ile Leu Gly Ile Pro Xaa Phe Leu Gly Pro Ala
                180                 185                 190

Leu Val Pro Gly His Ile Thr Thr Tyr Trp Leu Trp Phe Ile Leu Arg
            195                 200                 205

Gln Leu Glu Ala Ile Glu Thr His Ser Gly Tyr Asp Phe Ser Trp Glu
210                 215                 220

Xaa Thr Lys Tyr Ile Pro Phe Tyr Gly Pro Ala Tyr His Asp Tyr
225                 230                 235                 240

His His Tyr Val Gly Gly Lys Ser Gln Ser Asn Phe Ala Ser
                245                 250

<210> SEQ ID NO 14
<211> LENGTH: 305
<212> TYPE: PRT
<213> ORGANISM: Hordeum vulgare

<400> SEQUENCE: 14

Met Leu Pro Trp Ala Thr Ala Ala Glu Ala Glu Ala Ala Leu Gly Arg
1               5                   10                  15

Pro Met Thr Pro Ala Glu Ala Leu Trp Phe Arg Trp Thr Ala Gly Thr
            20                  25                  30

Pro Asp Tyr Gly Leu Tyr Cys Leu Asn Ile Leu Phe Leu Leu Leu Val
                35                  40                  45

Phe Thr Leu Ala Pro Leu Pro Val Ala Leu Leu Glu Leu Arg Ala Pro
50                  55                  60

Arg Ala Val Gly Pro Tyr Lys Leu Gln Pro Arg Val Arg Leu Ser Arg
65                  70                  75                  80

Ala Asp Phe Leu Lys Cys Tyr Gly Asp Val Met Arg Ile Phe Phe Leu
                85                  90                  95

Val Ile Gly Pro Leu Gln Leu Val Ser Tyr Pro Ala Val Lys Met Val
            100                 105                 110

Gly Ile His Thr Gly Leu Pro Leu Pro Ser Leu Gly Met Ala Ala
            115                 120                 125

Gln Leu Val Val Tyr Phe Leu Val Glu Asp Tyr Leu Asn Tyr Trp Ile
130                 135                 140

His Arg Leu Leu His Gly Glu Trp Gly Tyr Glu Lys Ile His Arg Ile
145                 150                 155                 160

His His Glu Tyr Thr Ala Pro Ile Gly Phe Ala Ala Pro Tyr Ala His
                165                 170                 175

Trp Ala Glu Val Leu Ile Leu Gly Ile Pro Ser Phe Ala Gly Pro Ala
                180                 185                 190

Ile Ala Pro Gly His Met Ile Thr Phe Trp Leu Trp Ile Ile Leu Arg
            195                 200                 205

Gln Met Glu Ala Ile Asp Thr His Ser Gly Phe Asp Phe Pro Phe Ser
210                 215                 220

Leu Thr Lys Tyr Ile Pro Phe Tyr Gly Gly Ala Glu Ser His Asp Tyr
225                 230                 235                 240
```

```
His His Tyr Val Gly Gly Gln Ser Gln Ser Ile Phe Ala Ser Val Phe
                245                 250                 255

Thr Tyr Cys Asp Pro Leu Cys Gly Thr Asp Arg Gly Tyr Arg Phe His
            260                 265                 270

Arg Ala Ser Leu Pro Met Leu Arg Ala Leu Ala Pro Pro Ala Ala Lys
            275                 280                 285

Lys Asp Ala Pro Met Gly Phe Ser Ser Ala Lys Gly Asp Tyr Val Val
290                 295                 300

Leu
305

<210> SEQ ID NO 15
<211> LENGTH: 301
<212> TYPE: PRT
<213> ORGANISM: Oryza sativa

<400> SEQUENCE: 15

Met Leu Pro Tyr Ala Thr Ala Ala Glu Ala Glu Ala Ala Leu Gly Arg
1               5                   10                  15

Ala Met Thr Ala Ala Glu Ser Leu Trp Phe Arg Tyr Ser Ala Gly Ile
            20                  25                  30

Pro Asp Tyr Val Leu Phe Trp His Asn Ile Leu Phe Leu Phe Val Val
        35                  40                  45

Phe Thr Leu Ala Pro Leu Pro Val Ala Leu Leu Glu Leu Arg Ala Pro
50                  55                  60

Ala Ala Val Gly Pro Phe Lys Leu Gln Pro Lys Val Arg Leu Ser Arg
65                  70                  75                  80

Glu Glu Phe Phe Arg Cys Tyr Arg Asp Val Met Arg Leu Phe Phe Leu
                85                  90                  95

Val Ile Gly Pro Leu Gln Leu Val Ser Tyr Pro Thr Val Lys Met Val
            100                 105                 110

Gly Ile His Thr Gly Leu Pro Leu Pro Ser Leu Gly Glu Met Ala Ala
        115                 120                 125

Gln Leu Leu Val Tyr Phe Leu Val Glu Asp Tyr Leu Asn Tyr Trp Ile
    130                 135                 140

His Arg Leu Leu His Gly Glu Trp Gly Tyr Glu Lys Ile His Arg Val
145                 150                 155                 160

His His Glu Phe Thr Ala Pro Ile Gly Phe Ala Ala Pro Tyr Ala His
                165                 170                 175

Trp Ala Glu Val Leu Ile Leu Gly Ile Pro Ser Phe Val Gly Pro Ala
            180                 185                 190

Leu Ala Pro Gly His Met Ile Thr Phe Trp Leu Trp Ile Val Leu Arg
        195                 200                 205

Gln Met Glu Ala Ile Glu Thr His Ser Gly Phe Asp Phe Pro Phe Asn
    210                 215                 220

Leu Thr Lys Tyr Ile Pro Phe Tyr Gly Gly Ala Glu Tyr His Asp Tyr
225                 230                 235                 240

His His Tyr Val Gly Arg Gln Ser Gln Ser Asn Phe Ala Ser Val Phe
                245                 250                 255

Thr Tyr Cys Asp Tyr Leu Tyr Gly Thr Asp Lys Gly Tyr Arg Tyr His
            260                 265                 270

Lys Ala Tyr Gln Ala Lys Met Lys Ala Leu Gly Gln Thr Glu Gly Glu
        275                 280                 285

Lys Ala Asp Ser Asn Gly Leu Ser Tyr Ala Lys Leu Asp
    290                 295                 300
```

<210> SEQ ID NO 16
<211> LENGTH: 301
<212> TYPE: PRT
<213> ORGANISM: Triticum sp.

<400> SEQUENCE: 16

Met Leu Pro Trp Ala Thr Ala Glu Ala Glu Ala Leu Glu Arg
1               5                   10                  15

Ala Met Thr Ala Ala Glu Ala Leu Trp Phe Arg Trp Thr Ala Glu Ala
            20                  25                  30

Ser Asp Tyr Tyr Leu Tyr Cys Leu Asn Ile Leu Phe Leu Leu Val Val
        35                  40                  45

Phe Thr Leu Ala Pro Leu Pro Val Ala Leu Leu Glu Leu Arg Ala Pro
    50                  55                  60

Arg Ala Val Gly Pro Tyr Lys Leu Gln Pro Arg Val Arg Leu Ser Arg
65                  70                  75                  80

Ala Glu Phe Ile Lys Cys Tyr Gly Asp Val Met Arg Ile Phe Phe Leu
                85                  90                  95

Val Ile Gly Pro Leu Gln Leu Val Ser Tyr Pro Ala Val Lys Met Val
            100                 105                 110

Gly Ile His Thr Gly Leu Pro Leu Pro Ser Leu Gly Glu Met Ala Ala
        115                 120                 125

Gln Leu Leu Val Tyr Phe Leu Val Glu Asp Tyr Leu Asn Tyr Trp Ile
    130                 135                 140

His Arg Leu Leu His Gly Glu Trp Gly Tyr Glu Lys Ile His Arg Ile
145                 150                 155                 160

His His Glu Tyr Thr Ala Pro Ile Gly Phe Ala Ala Pro Tyr Ala His
                165                 170                 175

Trp Ala Glu Val Leu Ile Leu Gly Ile Pro Ser Phe Ala Gly Pro Ala
            180                 185                 190

Ile Ala Pro Gly His Met Ile Thr Phe Trp Leu Trp Ile Ile Leu Arg
        195                 200                 205

Gln Met Glu Ala Ile Asp Thr His Ser Gly Phe Asp Phe Pro Phe Ser
    210                 215                 220

Leu Thr Lys Tyr Ile Pro Phe Tyr Gly Gly Ala Glu Tyr His Asp Tyr
225                 230                 235                 240

His His Tyr Val Gly Gly Gln Ser Gln Ser Asn Phe Ala Ser Val Phe
                245                 250                 255

Thr Tyr Cys Asp Tyr Leu Tyr Gly Thr Asp Arg Gly Tyr Arg Phe His
            260                 265                 270

Lys Ala Tyr Leu Ala Lys Leu Lys Asp Leu Ala Pro Ser Asp Gly Glu
        275                 280                 285

Lys Glu Gly Ala Asp Gly Phe Ala Tyr Ala Lys Leu Asp
    290                 295                 300

<210> SEQ ID NO 17
<211> LENGTH: 37
<212> TYPE: PRT
<213> ORGANISM: Artificial
<220> FEATURE:
<223> OTHER INFORMATION: Synthetic sequence, consensus of SEQ ID NOS:1-4
<220> FEATURE:
<221> NAME/KEY: misc_feature
<222> LOCATION: (2)..(2)
<223> OTHER INFORMATION: Xaa can be Leu or Ile or Met
<220> FEATURE:
<221> NAME/KEY: misc_feature
<222> LOCATION: (5)..(5)

-continued

```
<223> OTHER INFORMATION: Xaa can be Ala or Gly
<220> FEATURE:
<221> NAME/KEY: misc_feature
<222> LOCATION: (7)..(7)
<223> OTHER INFORMATION: Xaa can be Thr or Ala
<220> FEATURE:
<221> NAME/KEY: misc_feature
<222> LOCATION: (8)..(8)
<223> OTHER INFORMATION: Xaa can be Gly or Ala
<220> FEATURE:
<221> NAME/KEY: misc_feature
<222> LOCATION: (9)..(9)
<223> OTHER INFORMATION: Xaa can be Asp or Glu
<220> FEATURE:
<221> NAME/KEY: misc_feature
<222> LOCATION: (12)..(12)
<223> OTHER INFORMATION: Xaa can be Ala or Gly
<220> FEATURE:
<221> NAME/KEY: misc_feature
<222> LOCATION: (14)..(14)
<223> OTHER INFORMATION: Xaa can be Leu or Val
<220> FEATURE:
<221> NAME/KEY: misc_feature
<222> LOCATION: (17)..(17)
<223> OTHER INFORMATION: Xaa can be Ala or Thr or Ser or Gly
<220> FEATURE:
<221> NAME/KEY: misc_feature
<222> LOCATION: (18)..(18)
<223> OTHER INFORMATION: Xaa can be Leu or Met
<220> FEATURE:
<221> NAME/KEY: misc_feature
<222> LOCATION: (23)..(23)
<223> OTHER INFORMATION: Xaa can be Ala or Thr
<220> FEATURE:
<221> NAME/KEY: misc_feature
<222> LOCATION: (24)..(24)
<223> OTHER INFORMATION: Xaa can be Ala or Leu
<220> FEATURE:
<221> NAME/KEY: misc_feature
<222> LOCATION: (26)..(26)
<223> OTHER INFORMATION: Xaa can be Tyr or Phe
<220> FEATURE:
<221> NAME/KEY: misc_feature
<222> LOCATION: (27)..(27)
<223> OTHER INFORMATION: Xaa can be Arg or Glu
<220> FEATURE:
<221> NAME/KEY: misc_feature
<222> LOCATION: (31)..(31)
<223> OTHER INFORMATION: Xaa can be Ser or Val or Gly or Ala
<220> FEATURE:
<221> NAME/KEY: misc_feature
<222> LOCATION: (32)..(32)
<223> OTHER INFORMATION: Xaa can be Val or Met or Ile
<220> FEATURE:
<221> NAME/KEY: misc_feature
<222> LOCATION: (35)..(35)
<223> OTHER INFORMATION: Xaa can be Arg or Ser or Leu or Tyr
<220> FEATURE:
<221> NAME/KEY: misc_feature
<222> LOCATION: (36)..(36)
<223> OTHER INFORMATION: Xaa can be Tyr or Trp or Cys

<400> SEQUENCE: 17

Met Xaa Pro Tyr Xaa Thr Xaa Xaa Xaa Ala Glu Xaa Ala Xaa Gly Arg
1               5                   10                  15

Xaa Xaa Thr Trp Ala Glu Xaa Xaa Trp Xaa Xaa Tyr Ser Ala Xaa Xaa
            20                  25                  30

Pro Asp Xaa Xaa Leu
        35

<210> SEQ ID NO 18
<211> LENGTH: 30
<212> TYPE: PRT
<213> ORGANISM: Artificial
<220> FEATURE:
<223> OTHER INFORMATION: Synthetic sequence, consensus of SEQ ID NOS:1-
```

```
                16 with X defined
<220> FEATURE:
<221> NAME/KEY: misc_feature
<222> LOCATION: (2)..(2)
<223> OTHER INFORMATION: Xaa can be Ile or Met or Leu
<220> FEATURE:
<221> NAME/KEY: misc_feature
<222> LOCATION: (4)..(4)
<223> OTHER INFORMATION: Xaa can be Tyr or Trp
<220> FEATURE:
<221> NAME/KEY: misc_feature
<222> LOCATION: (5)..(5)
<223> OTHER INFORMATION: Xaa can be Ala or Gly or Pro or His
<220> FEATURE:
<221> NAME/KEY: misc_feature
<222> LOCATION: (6)..(6)
<223> OTHER INFORMATION: Xaa can be Thr or Ser
<220> FEATURE:
<221> NAME/KEY: misc_feature
<222> LOCATION: (7)..(7)
<223> OTHER INFORMATION: Xaa can be Ala or Thr or Leu or Val or Ile
<220> FEATURE:
<221> NAME/KEY: misc_feature
<222> LOCATION: (8)..(8)
<223> OTHER INFORMATION: Xaa can be Ala or Gly or Thr or Glu or Pro
<220> FEATURE:
<221> NAME/KEY: misc_feature
<222> LOCATION: (9)..(9)
<223> OTHER INFORMATION: Xaa can be Glu or Asp or Ala or Gly
<220> FEATURE:
<221> NAME/KEY: misc_feature
<222> LOCATION: (11)..(11)
<223> OTHER INFORMATION: Xaa can be Ser or Glu or Val or Gln
<220> FEATURE:
<221> NAME/KEY: misc_feature
<222> LOCATION: (12)..(12)
<223> OTHER INFORMATION: Xaa can be Gly or Ala or Ile or Val or Leu
<220> FEATURE:
<221> NAME/KEY: misc_feature
<222> LOCATION: (14)..(14)
<223> OTHER INFORMATION: Xaa can be Val or Leu
<220> FEATURE:
<221> NAME/KEY: misc_feature
<222> LOCATION: (15)..(15)
<223> OTHER INFORMATION: Xaa can be Gly or Asn or Ser or Glu
<220> FEATURE:
<221> NAME/KEY: misc_feature
<222> LOCATION: (17)..(17)
<223> OTHER INFORMATION: Xaa can be Thr or Ser or Gly or Ala or Pro or
        Asn
<220> FEATURE:
<221> NAME/KEY: misc_feature
<222> LOCATION: (18)..(18)
<223> OTHER INFORMATION: Xaa can be Met or Leu
<220> FEATURE:
<221> NAME/KEY: misc_feature
<222> LOCATION: (20)..(20)
<223> OTHER INFORMATION: Xaa can be Trp or Pro or Tyr or Arg or Thr or
        Phe or Leu or Ala
<220> FEATURE:
<221> NAME/KEY: misc_feature
<222> LOCATION: (21)..(21)
<223> OTHER INFORMATION: Xaa can be Ala or Leu or Phe
<220> FEATURE:
<221> NAME/KEY: misc_feature
<222> LOCATION: (23)..(23)
<223> OTHER INFORMATION: Xaa can be Thr or Ala or Ser
<220> FEATURE:
<221> NAME/KEY: misc_feature
<222> LOCATION: (24)..(24)
<223> OTHER INFORMATION: Xaa can be Ala or Leu or Ile or Val
<220> FEATURE:
<221> NAME/KEY: misc_feature
<222> LOCATION: (26)..(26)
<223> OTHER INFORMATION: Xaa can be Tyr or Phe or Leu
<220> FEATURE:
<221> NAME/KEY: misc_feature
<222> LOCATION: (27)..(27)
<223> OTHER INFORMATION: Xaa can be Glu or Arg or Asn or Asp or Lys
<220> FEATURE:
```

<221> NAME/KEY: misc_feature
<222> LOCATION: (28)..(28)
<223> OTHER INFORMATION: Xaa can be Trp or Tyr
<220> FEATURE:
<221> NAME/KEY: misc_feature
<222> LOCATION: (29)..(29)
<223> OTHER INFORMATION: Xaa can be Ser or Thr

<400> SEQUENCE: 18

Met Xaa Pro Xaa Xaa Xaa Xaa Xaa Ala Xaa Xaa Ala Xaa Xaa Arg
1               5                   10                  15

Xaa Xaa Thr Xaa Xaa Glu Xaa Xaa Trp Xaa Xaa Xaa Xaa Ala
            20                  25                  30

<210> SEQ ID NO 19
<211> LENGTH: 921
<212> TYPE: DNA
<213> ORGANISM: Zea mays

<400> SEQUENCE: 19

```
atgatcccct acgcgactgc ggcggaggcg gagggagcac tggggcgcac catgacgtgg      60
gctgagacag catggtacga gtactcggcg gtgatgccag attcctggct gcactgccac     120
accacattta tcctgttcgt catctacagc atcgccccgc tgcccctgct actcctagag     180
cagttcgctc cgtccgtcgt gctgccgtac aagctgcagc ccgggtacg gctgccccccg     240
gcagcctccc tcagctgcta catggacgcg gcctgcatct ttccgctcgc cgttggcctt     300
cagttcgtct cctatcctgc ggtcgccaag atactaagga cccgaatggg actgccgttg     360
ccgtcggtga gggagaccat cgcgcagcta gtcgtatact ctctagtgga ggattacctc     420
agctactgga tgcaccgtct gctgcacacc cagtggtgct acgagaagat ccaccgcgtc     480
caccacgagt tcacggctcc tacaggcttc gccatgtcgt acagccactg ggccgagaac     540
gtcgtccttt ctatcccggc cttggccggc ccagtgctcg tgccatgcca tgtcaccacg     600
cagtggctat ggttctccat ccgcctaatt gagggcatta acacgcacag cggttaccat     660
ttcccgttca gcccttgcag gctgattcca ttctacggag gggctgcata ccatgactac     720
catcactatg caggaggccg tagccaaagc aactttgcac ccctgttcac ctactgtgat     780
tatttatata ggacagacaa aggctacaga taccacaagc taaagcaaga gaagctgaag     840
agtctagcag aaaatagtgc ggataaagga ggcaactact cattcgacga agggaaaaag     900
aacagatatt tttgtgcctg a                                               921
```

<210> SEQ ID NO 20
<211> LENGTH: 882
<212> TYPE: DNA
<213> ORGANISM: Zea mays

<400> SEQUENCE: 20

```
atgatgccct acggcacggc ggcggaggca gaggcggcgc tggggcgctc catgacctgg      60
gcagaggccc tgtggttccg gtactcagcg gggatgccgg acctgtgtct gacgtggcac     120
gtctccctcg tctacctcgt cttgtacgcg ttggttccgc tgccggtcat ggttatccag     180
aagctcgcgc cggggtacgc cctgcggcac aagctgcagc ccggggtgcc ggagccctcg     240
ccggtttcca cctacgtcga atacataagg acagcaggg cgtcaccct ggccgccttg     300
ggcccgttcc cgctcatcta ctccatcgca ttcaagctgt tcggggtccg gacgggactc     360
cctttgccgt cggtctggga gactgcgacg cacctggcgg tgtattcgct ggtggaggac     420
tacacgtcgt actggctcca ccgcttcctg cacaccaggt gggggtacga gaagatccac     480
```

| | | |
|---|---|---|
| cgcgtccacc acgagaagac ggcgccgtcc gggttcgccg ccgcctacgc cacgggcact | 540 |
| gagctcagct tgtacctcac cacgctcttc cttgggccgg cgatcgtgcc cagccacgtc | 600 |
| accacgcact ggctcttgtt ctccatccgc ataatggagg ccttcgacac acacagcggg | 660 |
| taccacttcc cgttcagcct cgcgaggttc atcccgttct acgtggcgc ggaattccac | 720 |
| gactaccatc actacgccgg agagaagacc aggagcaatt tcagttccgt gttcacgtac | 780 |
| tgtgattata tatatgggac aaacaaaggc tacatgtacc acaagagaag cctagccgag | 840 |
| ctgaagacga aggaggccga acacagcggg aaagaagact ga | 882 |

<210> SEQ ID NO 21
<211> LENGTH: 855
<212> TYPE: DNA
<213> ORGANISM: Oryza sativa

<400> SEQUENCE: 21

| | |
|---|---|
| atgctcccgt acgcgacggc ggcggaggcg gaggcggcgg tggggcgggg cctgacgtgg | 60 |
| gcggaggcgg cctggttccg ctactcggcg gccatcccgg actactgcct ctactgccac | 120 |
| aacgtcccca tcctcctcct cgtctacacc ctcgcgccgc tccccctcgc gctgctcgag | 180 |
| ctccgccgcc acctgccgct gccgcacaag ctgcagcccg gcgtgcgcca cccgccggcc | 240 |
| gccttcctcc ggtgctacgc tgccaccgcg cgcgtgctgc cctcgccgt cgggccggtc | 300 |
| cagctggcgt cgttccctgc ggtgagggcg gtggggatac ggacggggct gccgctgccg | 360 |
| tcggcggggg agacggcggc gcaggtggcg gtgtacctgc tggtggagga ctacctgggc | 420 |
| tactggatcc accgcctgct gcacacgccg tgggcctacc accacatcca ccgagtccac | 480 |
| cacgagttca ccgcgcccat gggctacgcc gccccgtacg cccactgggc cgagatcctc | 540 |
| atcctcggct tcccggcctt cgccggccca gccatcgtgc cgtgccacat gaccaccttc | 600 |
| tggctctggt tcgtgcttcg ccacctcgag gccatccaca tccacagcgg gttcaagttg | 660 |
| ccgttcgatc cgaccaagta tatcccgttg tatggaggag tggagtacca tgactaccac | 720 |
| catttcgtgg aggacacag ccagagcaac ttctcttctg tcttcactttt ctgtgattac | 780 |
| atctacggga ctgacagagg ctacagatac cataaggcaa gcttgtcaaa gatgagaata | 840 |
| tttgttagag cttag | 855 |

<210> SEQ ID NO 22
<211> LENGTH: 907
<212> TYPE: DNA
<213> ORGANISM: Hordeum vulgare

<400> SEQUENCE: 22

| | |
|---|---|
| atgctgccgt acgcgacgac cggcgatgcg gaggcggcgc tcggccgcgc cctgacgtgg | 60 |
| gcggaggccg cgtggctccg ctactcggcg tccgtgccgg accgctacct ccactggccc | 120 |
| aacatcgcca tcacattggt cgtctacacg ctggcgccgc tgccgctcgc cctcttcgac | 180 |
| ctcgccgccc cggccgtcgc cgcgccgtac aagctgcagc ccaaggtgca gcacccgccc | 240 |
| gccaccttct ccgctgctca catggacgcc gttcgggtct cgctgctcat catcgggcca | 300 |
| taccagctca tctcctatcc cgccgcaaag ataatggaca tacggacggg acttccattg | 360 |
| ccgtcaatgg gggaaatagc agcgcaactg acgtatact tcttggtgga agactatctg | 420 |
| aactactggc tccatcggct gttgcacacc aaatggtgct atgaaaagat ccaccatgtt | 480 |
| caccatgagt tcacgcgcc catggcctat gccgcatggc atggacactg gctgagatg | 540 |
| ctcatccttg cggggccct ccttggccgg ccctgcactc gtccatgcc atgttaccac | 600 |

```
gctctggatc tggtttgcag cacgtttggt tgagagcctc aacatacata gcggatttaa      660
gttgccattc aacgctgaga agtacatacc attctacgga ggggcagagc accatgacta      720
ccatcactac ataggaggac agagcaagag caacttcgcc cctgttttca cctactgtga      780
ttacatatac ggaacggata aaggctacag atatcacaag gcaaccctgg caaagctgaa      840
ggagttggca ggaaacgagg ttcagaaagg agtcgacaac ggattcaaca gcggaaagca      900
ggagtag                                                              907

<210> SEQ ID NO 23
<211> LENGTH: 906
<212> TYPE: DNA
<213> ORGANISM: Zea mays

<400> SEQUENCE: 23
atgctgccct acgcgacggc ggcggaggcg gaggcggcgc ttggccggcc catgacgccc       60
gccgaggcgc tgtggttccg gtacaccgcg ggggtgtccg actaccacct ctactgctgc      120
aacatcctct tcctcttcgt cgtcttcacg gtggccccgc ttcccatcgc gctcctcgag      180
ctccgggccc cggccgcggt ctcgccgtac aaactgcagc cgcgggtgcg gctctccagg      240
gccgagttcg tccggtgcta caaggacgtc ctccgcatct tcttcctcgt catcggcccg      300
ctccagctcg tctcctaccc ggcggtcaag tttgtgggaa ttcacacgaa gttgcctttg      360
ccgtcccttg cggagttggc agcacagcta ctggtgtact ccttgttgga ggactacctc      420
aattactgga tccacaggtt tctccacggg gagtgggggt accagaatat ccaccgtgtt      480
caccatgagt tcactgcgcc aataggattc gcagctccat atgcacactg ggctgaggtg      540
ctgatactcg gcatcccctc cttcgtcggg ccagccattg ttccaggcca catgatcaca      600
ttctggctct ggattatact ccgtcaggtg gaggctatcg agacacatag cggctttgat      660
ttcccattca ccccgacaaa gtatattcca ttctatggag gagcagaata ccatgactat      720
catcattatg taggaggcca gagccaaagc aattttgctt ctgttttcac ttactgtgat      780
tacttatatg gcactgacaa aggttacaga ttccacaaaa catacctagc aaagctgaag      840
gatctggggc ataatgatgg ccagaaagga acggcagcg acccagcta tgtgaaactg      900 gattag                                                              906

<210> SEQ ID NO 24
<211> LENGTH: 900
<212> TYPE: DNA
<213> ORGANISM: Allium porrum

<400> SEQUENCE: 24
atgatcccct atccatctct gacagctgca gaagcggccc tgaaccgtcc gctaacctac       60
gccgaaacca tttggttcaa ttactccgcc acaatacccg atccgttgct gtattaccac      120
aatacgattt tcctttttgt tattttcacg ctagtacctc tcccttttggc tcttctcgag      180 ctctattggc cgtctgtttt gaagccgttc aagatccagc cgaaggtgta cctgtcgaaa      240
tctgagtttt tggaatgtta taagaatgtc attaaggttt tcttcttagt tgtttgcccg      300
cttcagcttc tgtcgtatcc tactgttaag ttcgtgggaa taaggactgg gctaccatta      360
ccatcagtat gggaagttgc atctcaatta gcagtgtact tcttgttgga ggattttgga      420
aattattgga ttcacagatg gctacatgga aaatgggggt acgagaagat tcacaaagtt      480
catcatgaat atactgcacc aataggtttt gctgctcctt acgccattg ggctgaggtg      540 ttgatccttg gtattccatc gtttcttgga cctgctattg ttcctggaca catgattact      600
```

```
ctttggttat ggatagctct gaggcaaatt gaggcactgg atacccatag cgggtacgac      660 ttcccttttga gttttaccaa gttcattcct ttctatggag gcgctgaata tcatgattat    720
catcattatg ttggagggca aagccagagc aatttcgctt ctgtgtttac gtattgtgac    780
tacgtatatg gaactgacaa gggttacagg tatcgaaagg catgcctctc gatgatgaag    840
gaagaatcgg aaaaccaaaa cggagttgag aattctttttc agaaccagaa atctgattga   900
```

<210> SEQ ID NO 25
<211> LENGTH: 897
<212> TYPE: DNA
<213> ORGANISM: Arabidopsis thaliana

<400> SEQUENCE: 25

```
atgattcctt acgctacagt cgaagaagct tcaatcgcac tgggacgaaa cctcacacgt     60
ctcgaaactc tatggttcga ttactccgcc acgaagtccg attactatct ctactgtcac   120
aacattttgt tcttgttcct cgtcttctct ctcgttcctc tccctctcgt tttcgtcgaa   180
ttggctcgat ctgcttctgg tttgtttaat cggtataaga tccagcctaa ggttaattac   240
tctttatctg atatgttcaa atgttacaaa gacgtcatga cgatgtttat cctcgtcgtt   300
ggtccattgc aactcgtttc ttatccttcg attcagatga ttgagatacg atctggatta   360
ccattaccaa caattacaga gatgctgtca cagttagtag tctacttctt gatagaagac   420
tacactaact actgggtaca tagattcttt catagtaaat ggggatacga taagattcat   480
cgagttcatc acgagtacac agctcctata ggatatgctg ctccttatgc acattgggct   540
gaagttttgc ttctcggaat cccgacgttt atgggaccag ctattgctcc tggtcatatg   600 ataaccttt ggttgtggat tgctttaagg caaatggaag ctattgagac tcacagtgga   660
tatgattttc catggagtcc aacaaaatac atcccttctct acggtggtgc tgagtaccat   720
gactatcatc actacgttgg aggacaaagt caaagcaact tcgcttcagt gttcacgtac   780
tgtgattaca tttatggaac tgacaagggt tacagattcc aaaagaagct tcttgagcag   840
atcaaggagt cgtcgaagaa gagcaacaag cataacggag gaataaaatc gattag       897
```

<210> SEQ ID NO 26
<211> LENGTH: 894
<212> TYPE: DNA
<213> ORGANISM: Arabidopsis thaliana

<400> SEQUENCE: 26

```
atgatcccat acgcaacaat cgaagaagcg tcgatcgcat tatctcgaaa cctcacatgg     60
ctagagactc tctggttcga ttactccgcc accaaatccg attactacct ctactgccac   120
aacattctct tcctcttcct catcttctct ctcgttcctc tccctctcgt tttcatcgaa   180
tcatctcaat ccacctcaga tttgttcaat cgctacaaaa tccaaccaaa agtgaaaaac   240
tcattctcat cgatgttcaa atgttacaaa gacgtcatga agatgttcat cctcgtcgtt   300
ggtccattac aactcgtttc ttatccttcg attcaggttg attttgtttt tcgtgtgttg   360
aaacagatga ttgagatacg aagtggatta ccattaccat catgtatgga gattgtagca   420
cagttagtgg tttacttctt ggtagaggat tatactaatt actgggttca tagattcttt   480
cattgtaaat ggggttatga agagtttcat catattcatc atgagtatac agctcctatt   540
ggttatgctg ctccttatgc tcattgggct gaggttttgc ttcttggcat tcccacgttt   600
cttggacctg ctattgctcc tggtcatatg attaccttt ggttgtggat tgctttacga   660
cagattgagg ctatcgaaac tcatagcgga tatgatttcc catggtctct gacaaagtac   720
```

| attccatttt | atggtggagc | tgagtatcat | gattaccatc | actacgttgg | aggacaaagc | 780 |
| cagagtaact | ttgcttcagt | ttttacttac | tgcgattaca | tctatggaac | tgataaaggt | 840 |
| taccgattcc | agaagaagct | tcttcagcag | gtaaataaat | actccataaa | ctga | 894 |

<210> SEQ ID NO 27
<211> LENGTH: 876
<212> TYPE: DNA
<213> ORGANISM: Arabidopsis thaliana

<400> SEQUENCE: 27

| atgatccctt | atccaaccgt | agaagatgcg | tccgtggcgt | taggacgaaa | ccttacttgg | 60 |
| ttcgagacgg | tttggttcga | ttactcagcc | accaaatcca | atttccatgt | atattgccac | 120 |
| accattctgg | ttctcttcct | tgtcttttca | ctagctcctt | ttcctcttgt | gattgtcgaa | 180 |
| tggaccggtt | ggttcgatca | gtttaagatt | cagaagaagg | ttaagtattc | gttgtctgat | 240 |
| atgttccaat | gttataaaga | agtcatgaag | ttgttccttc | tcgtcgtcgg | cacattgcaa | 300 |
| atcgtttctt | atccttccat | ccagatggtt | gggattcgaa | gtggtttgcc | attaccatcg | 360 |
| ttaatggaga | tagtagcaca | attagtggtt | tacttcttga | tagaagatta | cactaactac | 420 |
| tggatccata | gatggatgca | ttgcaaatgg | ggttacgaga | agattcatcg | aatccatcat | 480 |
| gagtacacat | cacctatcgg | atacgcatcg | ccgtatgcgc | attgggccga | gattttgatt | 540 |
| cttgggattc | cgacgtttct | tggaccggca | attgctcctg | gccatataat | gacgttttgg | 600 |
| ttatggatat | ctttacgaca | attcgaggcg | attgagaccc | acagcggata | tgattttcca | 660 |
| tggagtgtga | caaaattaat | tccatttac | ggtggacctg | agtatcatga | ctaccatcac | 720 |
| tacgttggag | acaaagcca | gagcaacttt | gcttcggttt | tcacttactg | cgattacatt | 780 |
| tatggaactg | ataaaggcta | tcgaatccat | aagaagcttc | ttcatcatca | gattaaagag | 840 |
| gaagctgaag | agaagagagt | aaggaaacac | gattag | | | 876 |

<210> SEQ ID NO 28
<211> LENGTH: 900
<212> TYPE: DNA
<213> ORGANISM: Arabidopsis thaliana

<400> SEQUENCE: 28

| atgatcccat | acgcaacaat | cgaagaagcg | tcgatcgcat | tatctcgaaa | cctcacatgg | 60 |
| ctagagactc | tctggttcga | ttactccgcc | accaaatccg | attactacct | ctactgccac | 120 |
| aacattctct | tcctcttcct | catcttctct | ctcgttcctc | tccctctcgt | tctcatcgaa | 180 |
| tcagctcaat | ccacctcaga | tttgttcaat | cgctacaaaa | tccaaccaaa | agtgaaaaac | 240 |
| tcgttctcat | cgatgttgaa | atgttacaaa | gacgtcatga | agatgttcat | cctcgtcgtt | 300 |
| ggtccattac | aactcgtttc | ttatccttcg | attcagatga | ttgagatacg | aagtggatta | 360 |
| ccattaccat | catgtatgga | gattgtagca | cagtttgtgg | tttacttctt | ggtagaggat | 420 |
| tatactaatt | actgggttca | tagattcttt | cattgtaaat | ggggttatga | aagtttcat | 480 |
| catattcatc | atgagtatac | agctcctatt | ggttatgctg | ctccttatgc | tcattgggct | 540 |
| gaggttttgc | ttcttggcat | tcccacgttt | cttggacctg | ctattgctcc | tggtcatatg | 600 |
| attaccttt | ggttgtggat | tgctttacga | cagattgagg | ctatcgaaac | tcatagcgga | 660 |
| tatgatttcc | catggtctct | gacaaagtac | attccatttt | atggtggagc | tgagtatcat | 720 |
| gattaccatc | actacgttgg | aggacaaagc | cagagtaact | ttgcttcagt | ttttacttac | 780 |
| tgcgattaca | tctatggaac | tgataaaggt | taccgattcc | agaagaagct | tcttcagcag | 840 |

```
atgaaggaga agtccaagaa gagcaacaag ctggttaatg gaggagagaa attcgattag    900
```

<210> SEQ ID NO 29
<211> LENGTH: 897
<212> TYPE: DNA
<213> ORGANISM: Brassica napus

<400> SEQUENCE: 29

```
atgatccctt acgcaacgat cgaagaggcc tctctggcgt taggccgaaa cctcacgacc     60
ctcgagactc tctggttcga ttactccgcc acgaagtcag attactacct atactgccac    120
aacatcctct tcctcttcct catcttctcc ctcgtccccc tccctctcgt cttcgtcgaa    180
ttggcgcgat ccgcctcggg atggttcgat cggtacaaga ttcagcccaa ggtcaagaac    240
tccttctccg acatgttccg ctgctacaga gatgtaatga gatgttcat cctcgttgtc     300
ggcccttttgc agctcgtgtc ctacccttca atccagatga ttgagattcg agtgggttg    360
ccgttaccgt ctttcgggga gattgcggcg cagttagtgg tgtacttctt ggtggaggac    420
tatacgaact attgggttca tagattcttt catagcaagt ggggttacga aagattcat     480
catatacatc atgagtacac tgctcctata gggtacgctg cgccttatgc gcattgggct    540
gaggttttgc ttcttggggt tccgacgttt cttggacctg ctattgctcc tggacacatg    600
attaccttct ggttgtggat tgcttttgcgc cagattgaag ccattgagac tcacagcgga    660
tatgatttc catggacact gacgaaattc attccattct atggtggagc tgagtatcat    720
gattaccatc attacgttgg aggacaaagc caaagcaact ttgcttcagt tttcacttac    780
tgcgattaca tctatggaac tgacaaaggt taccgattcc aaaagaagtt tcttcagcag    840
atcaagcagg agtccaagaa gagcaacatg cagaatggag gagataagtt agattag       897
```

<210> SEQ ID NO 30
<211> LENGTH: 894
<212> TYPE: DNA
<213> ORGANISM: Glycine max

<400> SEQUENCE: 30

```
atgctcccct acgcttccat cccggaggcc gtggcggcgc tgggccgcaa cctcaccttc     60
gcggagaccc tctggttcaa ctactccgcc gccaagtccg attacttcct ctactgccac    120
aacattctgt tcctcttcct cgtcttctcc ctcgtccccc tccccctcgt cttcctcgaa    180
ttcaagcgct ctccttcgt ctcttcccac aagatccaac caaagtccg cttgtccctg     240
gccgaaacct tcaagtgcta caagacgtc atgcgcatgt tcttcctcgt cgtcggcccc    300
ctccaactca tctcttaccc ttccatccag atgattggga tcaggacggg cttgccatta    360
ccttcgtggc gggagatcct ctcgcagctt ctggtgtact ttctcgtaga ggattacacc    420
aattactgga tccacaggtt tctgcacaac gattgggggt acgagaagat tcaccgcgtc    480
caccacgagt accatgcgcc cattggattc gccgcgccct atgcccactg gccgagatc    540
tgatcctcg ggattccctc ctttcttggg cctgccatgg ttcctggcca cattatcacc    600
ttctggctct ggatagcctt gcgccagatt gaagccattg acacgcacag cgggtatgac    660
tttcctagga gtatcacaaa atatattcca ttttatggtg gtgctgagta tcatgattac    720
catcattacg ttggaagaca aagccaaagc aattttgctt cagttttcac atactgtgat    780
tacatctatg gaactgacaa ggggtatagg tatcagaaaa aaatacttca gaagttgaag    840
gaagagttgg caaatggtgt tgagcagaac ggaggattat acaagactga ctga          894
```

<210> SEQ ID NO 31

<211> LENGTH: 764
<212> TYPE: DNA
<213> ORGANISM: Glycine max

<400> SEQUENCE: 31

| | | | | | |
|---|---|---|---|---|---:|
| atgctcccttt | accatacccct | tgaaggagca | caagttgcac | taggcagagg | actaacccttt | 60 |
| gctgagacaa | tatggttcaa | atactctgcc | aacaaacctg | attttgttct | tcattgccac | 120 |
| aacactctat | tcttgtgctt | attttactct | atagctccaa | ttcctttcgt | attaatggag | 180 |
| cttagtgggt | atgagaagct | aaacaaacac | aaaattcagc | cctcggttaa | gagatcattc | 240 |
| aaggaaatgt | tcaagtgcta | caaagatgtc | atggagacct | tgtcattgc | agttagccca | 300 |
| ctacagataa | tttcttatcc | caccatcaag | tggattggga | tcagaactgg | tttgtcattg | 360 |
| ccatcaggct | gggagttatt | ttggcaatta | tttatttact | ttgtcataga | agattttttcg | 420 |
| aattattgga | ttcataggat | gctccattgc | aagtgggcat | ttgagaagat | tcacaaggtc | 480 |
| catcatgaat | atgtagcacc | aattgggctc | tcagcacctt | atgcccattg | gccgagata | 540 |
| atcatattgg | gtatccccct | cgtttctagg | cccagcactg | gttcctgggc | atataacaac | 600 |
| ctattggcta | tggttcatttt | tgcgacagct | agaagccatc | gagactcata | gcgggtatga | 660 |
| ttttttcttgg | gaggcccaca | aaatatatac | cattttatgg | agggcctgca | taccatgact | 720 |
| accatcacta | cgttggtgga | aaaagtcaaa | gcaactttgc | ctca | | 764 |

<210> SEQ ID NO 32
<211> LENGTH: 918
<212> TYPE: DNA
<213> ORGANISM: Hordeum vulgare

<400> SEQUENCE: 32

| | | | | | |
|---|---|---|---|---|---:|
| atgctcccgt | gggcgacggc | ggcggaggcc | gaggcggcgc | tgggccggcc | catgacgccc | 60 |
| gcggaggcgc | tctggttccg | gtggaccgcc | gggacgcccg | actacggcct | ctactgcctc | 120 |
| aacatcctct | tcctcctcct | cgtcttcacg | ctcgcgccgc | tccccgtcgc | gctcctcgag | 180 |
| ctccgcgcgc | cgcggggccgt | cgggccgtac | aagctgcagc | cccgggtgcg | cctctcgcgg | 240 |
| gccgacttcc | tcaagtgcta | cggggacgtc | atgcgcatct | tcttcctcgt | catcggaccg | 300 |
| ctccagctcg | tctcctaccc | cgccgtcaag | atggtgggga | tccacaccgg | actgccgctg | 360 |
| ccgtctctgg | gggagatggc | ggcgcagctg | gtggtctact | tcctggtcga | ggactacctc | 420 |
| aactactgga | tccaccggct | gctgcacggt | gagtgggggct | atgagaagat | ccaccggatc | 480 |
| caccacgagt | acaccgcgcc | cattggcttc | gcagcgccat | acgctcactg | gcagaggtg | 540 |
| ctcatacttg | gcatcccctc | cttcgctggc | ccggccattg | caccaggcca | catgattacc | 600 |
| ttctggctct | ggattatact | tcgtcagatg | aagccattg | acacacacag | cggttttgat | 660 |
| ttcccattca | gcctgacaaa | gtatattccg | ttctatggag | gagcagaatc | ccatgattat | 720 |
| catcactacg | ttggaggcca | aagccagagc | atttttgctt | cggttttcac | gtactgtgat | 780 |
| ccctgtgtg | gcaccgacag | aggctacaga | ttccacaggg | cttccttacc | aatgttgagg | 840 |
| gccctggccc | ccccgccgc | caagaaagat | gccccatgg | gtttcagttc | cgcgaaggg | 900 |
| gattacgtgg | tcttatag | | | | | 918 |

<210> SEQ ID NO 33
<211> LENGTH: 906
<212> TYPE: DNA
<213> ORGANISM: Oryza sativa

<400> SEQUENCE: 33

```
atgctgccct acgcgacggc ggcggaggcg gaggcggcgc tggggagggc gatgacggcg    60
gcggagtcgc tgtggttcag gtactcggcg gggatcccgg actacgtcct cttctggcac   120
aacatcctct tcctcttcgt cgtcttcacg ctcgcgccgc tccccgtcgc gctcctcgag   180
ctccgcgcgc cggccgccgt ggggccgttc aagctgcagc ccaaggtgcg gctctcccgg   240
gaggagttct tccgctgcta cagggacgtc atgcgcctct tcttcctcgt catcggcccg   300
ctccagctcg tgtcctaccc taccgtcaag atggtgggaa tccacacagg ctgccactg    360 ccgtcgctgg gggagatggc ggcgcagctg ctggtgtact tcctggttga ggactacctc   420
aactactgga tccatcggtt gctacatggg gagtggggct atgagaagat ccaccgtgtc   480
caccatgagt tcacggcacc cattggattc gccgcgccat atgcacactg gctgaggtg    540 ctcatcctcg gcatcccctc ctttgtcggg ccagcgcttg cacctggtca catgatcacc   600
ttctggctct ggattgtact ccgccagatg gaggccatag agacacacag cggctttgat   660
ttcccgttca acctgacaaa gtatattcca ttctatggag cgcagaata  ccatgattat   720 catcactatg ttggacgcca gagtcagagc aatttcgctt ctgttttcac gtattgtgat   780
tatctatatg gaaccgacaa aggttacaga taccataagg cgtaccaagc aaagatgaag   840
gctctggggc aaacggaagg cgagaaagca gatagcaatg gattgagcta cgcgaagttg   900
gattaa                                                              906

<210> SEQ ID NO 34
<211> LENGTH: 906
<212> TYPE: DNA
<213> ORGANISM: Triticum sp.

<400> SEQUENCE: 34
atgctcccgt gggcgacggc ggcggaggcc gaggcggcgc tggagcgcgc catgacggcc    60
gcggaggcgc tctggttccg gtggaccgcg gaggcgtccg actactacct ctactgcctc   120
aacatcctct tcctcctcgt cgtcttcacg ctcgcgccgc tccccgtcgc gctcctcgag   180
ctccgcgcgc cgcggggccgt cgggccgtac aagctgcagc cccgggtgcg gctctcgcgg   240
gccgagttca tcaagtgcta cggcgacgtc atgcgcatct tcttcctcgt catcggcccg   300
cttcagctcg tctcctaccc cgccgtcaag atggtgggaa tccacaccgg actgccgctg   360
ccgtctctgg gggagatggc ggcacagctg ctggtctact tcctggttga ggactacctc   420
aactactgga tccaccggct gctgcacggt gagtgggggct atgagaagat ccaccggatc   480
caccatgagt acaccgcgcc cattggctt  gccgcgccat acgcacactg gcagaggtg    540 ctcatacttg gcatcccctc cttcgctggg ccggccattg caccaggcca catgataaca   600
ttctggctct ggattatact tcgtcagatg gaagccattg atacacacag cggttttgat   660
ttcccattca gcctgacaaa gtatattcca ttctatggag gagcagaata ccatgattat   720
catcactacg ttggaggcca aagccagagc aattttgctt ccgttttcac gtactgtgat   780
tacctatatg ggaccgacag aggttacaga ttccacaagg cttacttagc aaagttgaag   840
gatctggcgc caagcgacgg cgagaaagaa ggtgccgacg gattcgctta tgcaaagttg   900
gattag                                                              906

<210> SEQ ID NO 35
<211> LENGTH: 1384
<212> TYPE: DNA
<213> ORGANISM: Oryza sativa

<400> SEQUENCE: 35
```

-continued

```
ctcgaggtca ttcatatgct tgagaagaga gtcgggatag tccaaaataa aacaaaggta      60
agattacctg gtcaaaagtg aaaacatcag ttaaaaggtg gtataaagta aaatatcggt     120
aataaaaggt ggcccaaagt gaaatttact cttttctact attataaaaa ttgaggatgt     180
ttttgtcggt actttgatac gtcatttttg tatgaattgg tttttaagtt tattcgcttt     240
tggaaatgca tatctgtatt tgagtcgggt tttaagttcg tttgcttttg taaatacaga     300
gggatttgta taagaaatat ctttaaaaaa acccatatgc taatttgaca taattttga     360
gaaaaatata tattcaggcg aattctcaca atgaacaata ataagattaa aatagctttc     420
ccccgttgca gcgcatgggt atttttcta gtaaaaataa aagataaact tagactcaaa     480
acatttacaa aaacaacccc taaagtccta aagcccaaag tgctatccac gatccatagc     540
aagcccagcc caacccaacc caacccaacc caccccagtc cagccaactg gacaatagtc     600
tccacacccc cccactatca ccgtgagttg tccgcacgca ccgcacgtct cgcagccaaa     660
aaaaaaaaaa gaaagaaaaa aaagaaaaag aaaaacagc aggtgggtcc gggtcgtggg     720
ggccggaaac gcgaggagga tcgcgagcca gcgacgaggc cggccctccc tccgcttcca     780
aagaaacgcc cccatcgcc actatataca tacccccccc tctcctccca tcccccaac     840
cctaccacca ccaccaccac cacctcctcc cccctcgctg ccggacgacg agctcctccc     900
cctccccct ccgccgccgc cggtaaccac cccgcccctc tcctctttct ttctccgttt     960
ttttttccg tctcggtctc gatctttggc cttggtagtt tgggtgggcg agaggcggct    1020
tcgtgcgcgc ccagatcggt gcgcgggagg ggcgggatct cgcggctggg gctctcgccg    1080
gcgtggatcc ggcccggatc tcgcggggaa tgggctctc ggatgtagat ctgcgatccg    1140
ccgttgttgg gggagatgat gggggggttta aaatttccgc catgctaaac aagatcagga    1200
agaggggaaa agggcactat ggttatatt tttatatatt tctgctgctt cgtcaggctt    1260
agatgtgcta gatctttctt tcttcttttt gtgggtagaa tttgaatccc tcagcattgt    1320
tcatcggtag ttttcttttt catgatttgt gacaaatgca gcctcgtgcg gagctttttt    1380
gtag                                                                 1384
```

<210> SEQ ID NO 36
<211> LENGTH: 1316
<212> TYPE: DNA
<213> ORGANISM: Zea mays

<400> SEQUENCE: 36

```
ctgccacatc ggcatgtact tagggcgcta gctctccccc gctagacacg tagcactctg      60
ctacacccct cattgtacac ctggatcctc ttcttacgcc tataaaagga aggaccagga     120
ccctcttaga gagggttggc cgcgcgggga cgaggacgag acaggcgctc tcttggggcc     180
gctcgcttcc ctctcccgcg tggacgcttg taactcccta ctgcaagcgc acccgacctg     240
ggcgcgggc gaacacaaag gccgcgggat tcccacctct ctcacgccgg tctccggccg     300
cctcgcttct ctccccttcg cgctcgccct cgcgctcgac ccatctgggc tggagcacgc     360
gacgacactc actcgtcggc ccaagggacc ccccggtctc ggaacgcgac actatctttt     420
cacacttaga agctggcaag aaggtcaaac aaataaggtc ttatcgtgta tattatttt     480
gcattgcaga tagagtggag tttgaaataa aaggtgagat agcaggagtg gaaatgggct     540
caaaaattta tactataaaa ttgaatgatc aaatcgaatt aagatcggac tttatttgta     600
ttcattcttg aactaaaatt atttaactat cataatttat tgtggataaa catttggacc     660
acgattcatt gccatcgata ggaggtgttg taagagagcc agaaagctta ggacatgtaa     720
```

```
cccgattaaa taaagagtct tttgaagtgt ccctaagggc tacgtgaaaa aaaatcaaga    780
gacatactct ttgtgaagag tctgtctcta cacaaatctc tatataagtt gtgtctcaat    840
tacattatta tctagagact cagtgttgta tcacgtagtc ttttagtggt ctctttattt    900
tgaaatccgt tgcagagtcc cttatgtgca gagtttggac atcccacgcg gtagaagcga    960
cgtggcagtt gccacagtat actgacgtgt gggcccagaa aaccccactg tcaatggaga   1020
aagaccatcc aaagcacaga gacttctatt ttattcgtga ctcttccaga atcccgacca   1080
tcccacacag agccacggac gcgggacgcc tacgcctcgc cgcgcccggg ccccgcaca    1140 gtccacagcc tttcagaacc ttccgtcgcc ttccagaaga acagaagccc acccgtcgcc   1200
accaatataa atcgcccctc cagatcggca ctccgcacac caagaatcac atcacacagc   1260
gaaccgagaa accaacacag caacaagcaa agcagcgatc cgacatccga gagatg       1316

<210> SEQ ID NO 37
<211> LENGTH: 764
<212> TYPE: DNA
<213> ORGANISM: Zea mays

<400> SEQUENCE: 37
gtggagtggt ggacactagt gccgcggttc atctgacacg tgtcgccacg tgccgccatg     60
gcagcacctc agcccggccg gcgggccgac tgacgtcttg ggcaaagcgg cgagcgacgc    120
aggcggcgaa agccatccga tttgaccccct cgctagaccc ttcaagaacg aacgctgtgc   180
tgctcagatc agaccgtgtc tgcctcaaag cgatgccagg acgccacgtc caagcaaagc    240
acccgatgcc attgccacct cccagcactc acgcgtgagc gtgactataa aaaacgcacc    300
ctctgcatcc gccccgtct gcctgcccta ccgaatcttt cgccgtccca tcagcccagc    360
aattcttcgc tgttcgagga cccctcggtt tcgaccgaag cccagcaagc cgaccacaca   420
ccgctgccgt tggttccgtc ccaagagatg ggcaagtcct ggtcgctcat cagccacctc   480
cacaccgtcg ccgggtagtt tcactgttcc ctcgcagttc gtttccgat tcctcctcgt    540 ccatctattg ggctcgctcg acgctggatg cctgacgtgt gcgtttgctg cttctttgtc   600
ttgtctgtcc ctccctcccg tttcgcaggc caagcatcac cctgctgtac cctctgtaag   660
ttccttcatc accctaataa tagcagggac cagttttacc agtgcagcag tgaccgacca   720
cggtccacgg catacgtgag ctgagagcat cgtgctggga catg                    764

<210> SEQ ID NO 38
<211> LENGTH: 1380
<212> TYPE: DNA
<213> ORGANISM: Zea mays

<400> SEQUENCE: 38
cgacctgcag gcggccgcga attcactagt gattactata gggcacgcgt ggtcgacggc     60
ccgggctggt aagacttaaa aatcaacaat atcttcacat gacttaatta taatgtcttg    120
cttgagacgt tgttttgct actacataag ataaagttca aataaatgca tggtggagtt     180
cagcctaggc aaagtgatgg tccgaatgat taacaccca agcaagacat tataagtcat    240
gtgaagatct gcaagacgtg ctaagagtct ctgacacacc aacaagtgga agcccgaaca    300
aacaaaaacg aagccatcaa agttgagata aagaggtgga taaattgaaa attgtctcat    360
gattttggat atactcaaat cgacatgact tcatctctaa actatagaac ttttgatttg    420
cttttcaaaa agtccaagat caacaaaacg tgttggtggg tgcgggtttg gtcgttaacc    480
caataggttt tttctcgtgt gtatgaaaag gttgtaccca tgtgtgaccg agccagacag    540
```

```
gggtacgggc aaaccgaagg gaaaccactt aggtggatcc cttggctagc ctgagactga    600
cacaccataa gtgatcggcc gcttttaact acgcctggtg ccgagccaca atagagatgt    660
cggtctgtct cccacttatg acctacgaac ccctcgtact atggctcatc tatgggtcgt    720
gtgccccttg gcttactgcg cactcatgcc ctatcaaggc taggccagag tgcgtaggcc    780
gctttcagag atcactcggt gaaaaaatca ctcggtgatg aaaccggcga actgtcgttg    840
ggtgggtggg tcttactatc aaagaaaacg tattccagca aacgtattcc actctccaca    900
aaataaacat ttctgttcgg ttacctaggt gaggcatcct gtaagaactt ggctgtgttt    960
agtcacagca aacgtatacc actctccaca aaataaaata aaaacgggt cagtgaagct     1020
gcaattaatc ccttctcttg cttgctggtt gctgccaggg aaatggcatt agtgtttgtt    1080
cccgttccga agaccgcagc aaccccggga atcggaaacg cctgccccct gcagcaccaa    1140
agaccgtacc aaccccgca atcgcagttc gcaaaccaaa ctaatttgtg tacacaaacc     1200
ggccccgtct cggttctatt ctataaaacc cccgccagac cgctggcttg ttccgtcgcc    1260
tccgctgtcc gctgcacaga ctgtagtacc ggggcagggg caggggcagg ggcacaaaca    1320
gagccacacc acacacagac cccacctacg ctacgctacg cgcgtgctgg gcgagtgatg    1380
```

<210> SEQ ID NO 39
<211> LENGTH: 574
<212> TYPE: DNA
<213> ORGANISM: Zea mays

<400> SEQUENCE: 39

```
gtcctaattg gtactcctga gatactatac cctcctgttt taaaatagtt ggcattatcg     60
aattatcatt ttacttttta atgttttctc ttcttttaat atattttatg aattttaatg    120
tattttaaaa tgttatgcag ttcgctctgg acttttctcg tgcgcctaca cttgggtgta    180
ctgggcctaa attcagcctg accgaccgcc tgcattgaat aatggatgag caccggtaaa    240
atccgcgtac ccaactttcg agaagaaccg agacgtggcg ggccgggcca ccgacgcacg    300
gcaccagcga ctgcacacgt cccgccggcg tacgtgtacg tgctgttccc tcactggccg    360
cccaatccac tcatgcatgc ccacgtacac ccctgccgtg gcgcgcccag atcctaatcc    420
tttcgccgtt ctgcacttct gctgcctata aatggcggca tcgaccgtca cctgcttcac    480
caccggcgag ccacatcgag aacacgatcg agcacacaag cacgaagact cgtttaggag    540
aaaccacaaa ccaccaagcc gtgcaagcat catg                                574
```

<210> SEQ ID NO 40
<211> LENGTH: 571
<212> TYPE: DNA
<213> ORGANISM: Zea mays

<400> SEQUENCE: 40

```
ctcgagggta ctcctgagat actataccct cctgttttaa aatagttggc attatcgaat     60
tatcatttta cttttaatg ttttctcttc ttttaatata tttatgaat tttaatgtat     120
tttaaaatgt tatgcagttc gctctggact tttctgctgc cctacacttt gggtgtactg    180
ggcctaaatt cagcctgacc gaccgcctgc attgaataat ggatgagcac cggtaaaatc    240
cgcgtaccca actttcgaga agaaccgaga cgtggcgggc cgggccaccg acgcacggca    300
ccagcgactg cacacgtccc gccggcgtac gtgtacgtgc tgttccctca ctggccgccc    360
aatccactca tgcatgccca cgtacacccc tgccgtggcg cgcccagatc ctaatccttt    420
cgccgttctg cacttctgct gcctataaat ggcggcatcg accgtcacct gcttcaccac    480
```

| | |
|---|---|
| cggcgagcca catcgagaac acgatcgagc acacaagcac gaagactcgt ttaggagaaa | 540 |
| ccacaaacca ccaagccgtg caagcaccat g | 571 |

<210> SEQ ID NO 41
<211> LENGTH: 733
<212> TYPE: DNA
<213> ORGANISM: Oryza sativa

<400> SEQUENCE: 41

| | |
|---|---|
| tagcatatat aaaatcattt gtcagagtga acaacacat ccaaattaat gacaaatata | 60 |
| aattactaat ctactttgat ccatctcatc attttaaag aaaatactaa atccattaa | 120 |
| aagatcattt tggaaaatta aacttttatt gaaaataaac taactcatgt aaaattatac | 180 |
| cgttttcctg ttcatgtac aggatataaa ttaacagcgc gccttttggc gcgctgattt | 240 |
| tctagtcgaa aagttaaacc ggggtataag tgtagcacct tcgctccact caaagaaaat | 300 |
| gtaagccgaa gacttgagaa gcttccagaa tccagagatc gcagcagaaa aggagcgaac | 360 |
| aaggcaaacc tctcaaagga aaaagaaaa ataataaagg aggaaacctg tcaaacacca | 420 |
| ccctatgaca agtgggtccc actcgaacca accgtacggc cccccaccc aaacccgctc | 480 |
| ccccctcgct ccgaaaatat ccacctctct agatctttct cgtcgcaaac gcccttccgc | 540 |
| ccccgcctcg ccgcgcccat tccaccacct ttccgaacct tccactccct tccagactcc | 600 |
| acccccacgt caccccctatt taaacccctc ctcccaccga gcaatcaagc gacaagatcg | 660 |
| agaagccaca aaccccagcg cgatccgagg tagaagaaga agaagaagaa gaagaagaag | 720 |
| aggcgatcga gag | 733 |

<210> SEQ ID NO 42
<211> LENGTH: 1019
<212> TYPE: DNA
<213> ORGANISM: Oryza sativa

<400> SEQUENCE: 42

| | |
|---|---|
| aatataccat tcgctaaaaa atttgatttt tctatgacgg agaaagcagt agtgtaagca | 60 |
| gagcgcccgt aaacatatcc tcacttttgg ttcatctcat attttttgtaa gatggaggaa | 120 |
| acatgagtga aattagagca ccctgtaaac atatcctcat tttggttcgt ctatcagtca | 180 |
| cgtaactttg ttatttctgt cggttaccta gtactaatac ctaagatgat aatccactgt | 240 |
| aatgggaaga tgagcacggt tttatatctg aaactgaaaa tgggtctgtt ggtcataaaa | 300 |
| cttactacct ccgtttcgaa atatatcaaa ctagcttgta ttagattaga cacgatctat | 360 |
| tattcaattt ggacagagtc catatagcta tgatatgctt actatttcat attgctttca | 420 |
| tgaacttaac ttaagttttt ggaccacaat gaaagtttca gttcatatca tatggcatac | 480 |
| tacttctatt ctttttttt tgttaaaaaa aaactggagc tctcaatttt tttaaagttt | 540 |
| gtcctgttac aattttaatc agttctttat tattcctctc cacatcaaca atttttcctc | 600 |
| gatgatccgg ttcccttttg acctcactgc actgtcccag atctctcatt aatccaaccc | 660 |
| agaaaaaaaa aacagtacaa aataaaatac acaagattca acaaagcaac ctgacctggt | 720 |
| cggtgctgta ccacgtggca tctccctcc atgtcccaat cacttcgaga gacaaaagaa | 780 |
| acactcctcc agtggcatcc tgccatgtgt cctccattct tgtacttaat ctcttcttat | 840 |
| ttaaggcctc ataatctctt gctttccctt ccctagtaaa tcaaagaaca caaagcatcc | 900 |
| aaaacaacac caggaaactt cttttcaatc gatcactcca ctggtgagta gtgagtggct | 960 |
| agtgactggt cagttcatca cttgtgaagg ttttgcaatc aggaaaagtt cagaagatc | 1019 |

<210> SEQ ID NO 43
<211> LENGTH: 1500
<212> TYPE: DNA
<213> ORGANISM: Oryza sativa

<400> SEQUENCE: 43

```
tttgatttgg gacaaaaggt tggtgaaatg gacatatttt cacatatata tatgctatat      60
ttttcttctc agtttaccga aaagatgtac ccttatatct cgtcatcgat tttgggtcag     120
gccagaaaac cattggtaac agaatatatg catagttttc tttatcaata aaattaatgt     180
tttatttaaa aatcgataaa ggaacttttt acaaaattag gctagaaatg gtctgtctat     240
tatgacaagg taaacttttg cgacattaat ttggatggca acttcaacaa ttcaaattgt     300
cgttgtccac aaatctcttg gttgtagaag acccacgcgt ctgcaacatt tttgcgccga     360
aaacttaata cataaacttg atttgttggg atacatggtg cagaagatac gatcattaat     420
aattcaaaca gtgcatttca tggtccaact gactgccacg tcattgaacc cgtaatcatt     480
cgctaagcca aatcaaattg gcctcaaatg aattttcagc acgactttt acgccccaaa      540
aacctagtac tccctccagt tggaaatgta ccctaccaag aaacttgtgt ccgtcacgac     600
gcctgtatca tcaatctagt cctcttttgt aacaaaataa ttttagaaga tttctttttaa    660
tgccgtagaa attaaattaa tcctaatgaa aatcatgtaa aactcacccg ttataaaatg     720
tcactaaccc cctacacggt tggtgtcctc tttgtagccg aaatgcctcc tctttggcca     780
ctgcatctcc acccatttt caaacatctc caactaactt tttgttccat ttgcaaaaat      840
gcaaaatgcg aaatgttaac ttcacacaca cccccctacc actacaaaac tctccaccaa      900
cccaatctag ctatcagttc agaaagcacc ttcccttctt tccctattag agcaagtcta     960
atagtacagc tcactactag cttcaattta tctataacca atctaatagt caattcatac    1020
aatagttgct tattatacta ttaatatatg gtctcacctg tcatacacac agtgtgtctt    1080
atagtccgtg ctgcagctgg ctacatatct gtagcctgct agtcttctct ctcatcgttt    1140
atctcattaa aatatgttta tagctggcta atagcttgct aatagcatgc tattgtacct    1200
gctcttacca ccttctttcc cttttggcaa atggcaatga gtgcaaaaat gcttggaaaa    1260
ataaccccc cccccccacc cccacctgat tatttccagt agggccaaaa tccgggccca    1320
cgtccgcaac ccatgtgggc cccacatccc ccacaccaac cctctgcacc caaaatcccc    1380
atccccccac tatatataat ccccgccgtt ggatcatcgc cctcagcaga gcagcgcatc    1440
tgcatccaaa accaaaccca aactcgtctt ctccaccgga gcagagcagc ggcggcggca    1500
```

<210> SEQ ID NO 44
<211> LENGTH: 1180
<212> TYPE: DNA
<213> ORGANISM: Oryza sativa

<400> SEQUENCE: 44

```
aaaacctctt ctttaacatg taaacgacct ggaggatgtc aactctgaca cgctggcgaa      60
atcatccacc tatgtctttg ccgcggtata ggatgaacat gggtagagaa aaaaatcggg     120
gtgatccaaa gtgcaataga cgtgacccaa aaagtgtaat tcactaaaaa aaacttacca    180
acgaagcaat gctttggcag tgattttac ctttcagtca tgggcatgac ctgcattgta      240
aaataacgtg gttgtgaatt caaactcaaa tgtgtttttc tttcacaagt tgccgttaaa     300
aatatgtttc gcaagagact cactgctccc agtgaaagca gtgaattgaa gcattcccga     360
aacccactgg aatgatctag tactcactct acgatgtaca gtgaagtaat acttcaaaac     420
```

```
tggtgtaatt tggtatgcca aaaggactcc atagtttcac gacatatttc caaacggttc      480
aggatcagta ctgcccatct gcctgggggcc cacactagcg ggcaattggt tctcgtagtt     540
tctcgttctc aatcaatcat tccatactcg ctatcccctc catcacagaa taaatgcaac     600
aatgagtttc cgtgtacaaa tttaatcgtt cgtcttattt aaaatatttt ttaaaaaact     660
aaaaaacaaa agtcacgcat aaagtactat tcatgtttta taatctaata acagtataaa     720
tactaatcat aaaaaaaaat tcaaataaga tggacgatta agttgaaaca ctgaaattca     780
tggctgcttt tgttttgaga ctgagggagt acacgataag atttgatcgc aatcaaagta     840
acctacatca aagaagcaag atatgtgggg gaaaaatgaa tactctagag caaattaagg     900
tgagccccgc tttgtagagg ctgatggagt actggagcga cggaagcgaa gcagatcgag     960
tgtgctgtaa agcgaaacga gcaagaacca gagaagtcca gagatttcag gacagattag    1020
ttgtgaacct ataaatatcc tgcctcattc cccaacctcc atccatcgag ccaagactga    1080
agcatttgat cgagctccaa acaaacactc gttccaaact tcctccaatc cacttcatac    1140
aaagaaacct aagcagctag cgatccacga caaaccaaca                          1180

<210> SEQ ID NO 45
<211> LENGTH: 339
<212> TYPE: DNA
<213> ORGANISM: Oryza sativa

<400> SEQUENCE: 45
gttcgtgact tttggcaagg gatcgaatcg gaagcgaatg ggtgggccca aaacgggccg      60 gttatttac tgggactaaa gatatcggcc catctgaatt gtgcgttccg ccggataagg     120
gataactgaa ggcggcgctc agtcccgcgc cttctggaac cttcccgtgg aaggggcata    180
cagccttgca gcggcagctt ccggaagctt ctgaattctt ctccaagatt tgccgcgacg    240
ataaatcctc tcgtttctcc gctcgctgat tcattctcaa cgcaaaatcc aaaagataag    300
cacagttacg cggcgagagc gagagaggag tggagagcc                           339

<210> SEQ ID NO 46
<211> LENGTH: 991
<212> TYPE: DNA
<213> ORGANISM: Oryza sativa

<400> SEQUENCE: 46
tgcttgccct tgtcctcatg tacacaatca gcttgcttat ctctcccata ctggtcgttt      60
gtttcccgtg gccgaaatag aagaagacag aggtaggttt tgttagagaa ttttagtggt     120
attgtagcct atttgtaatt tgttgtact ttattgtatt aatcaataaa ggtgtttcat      180
tctattttga ctcaatgttg aatccattga tctcttggtg ttgcactcag tatgttagaa     240
tattacattc cgttgaaaca atcttggtta agggttggaa catttttatc tgttcgtgaa     300
acatccgtaa tattttcgtt gaaacaattt ttatcgacag caccgtccaa caatttacac     360
caatttggac gtgtgataca tagcagtccc caagtgaaac tgaccaccag ttgaaaggta     420
tacaaagtga acttattcat ctaaaagacc gcagagatgg gccgtgggcc gtggcctgcg     480
aaacgcagcg ttcaggccca tgagcattta ttttttaaaa aatatttca caacaaaaaa     540 gagaacggat aaaatccatc gaaaaaaaaa actttcctac gcatcctctc ctatctccat     600
ccacggcgag cactcatcca aaccgtccat ccacgcgcac agtacacaca catagttatc     660
gtctctcccc ccgatgagtc accaccgtg tcttcgagaa acgccgcc cgacaccgta       720 cgtggcgcca ccgccgcgcc tgccgcctgg acacgtccgg ctcctctcca cgccgcgctg     780
```

-continued

| | |
|---|---|
| gccaccgtcc accggctccc gcacacgtct ccctgtctcc ctccacccat gccgtggcaa | 840 |
| tcgagctcat ctcctcgcct cctccggctt ataaatggcg ccaccacct tcacctgctt | 900 |
| gcacaccaca gcaagagcta agtgagctag ccactgatca aagaacacc tcgatctccg | 960 |
| agagtttttt ttcagcttta gcttaagcag g | 991 |

<210> SEQ ID NO 47
<211> LENGTH: 368
<212> TYPE: DNA
<213> ORGANISM: Zea mays

<400> SEQUENCE: 47

| | |
|---|---|
| atctctctct ctctctctaa aagaaggaac acgtatcggt agatcgattc cagacgctta | 60 |
| ccatcgcatc gttatcatag agttaaaatc gtctgtgtcg cgtaacattt ctgaaaataa | 120 |
| tttcggaaga tgaagataat gtttctgtta cgtaattttc cgtcccttgt tgttcacatg | 180 |
| tgcgtaccca cgtgtcagag tgagagatgt accagtataa agaagcgcag agcccccaag | 240 |
| agccggagct gccatgaggc ccgaacagtt gaagctacta gcgtgtagct agggaagaga | 300 |
| agcgcgcgag tagctagcag acgtacgtag gcagaagcct agctgggttt gaagggcccc | 360 |
| gatcgatg | 368 |

<210> SEQ ID NO 48
<211> LENGTH: 2091
<212> TYPE: DNA
<213> ORGANISM: Zea mays

<400> SEQUENCE: 48

| | |
|---|---|
| atccacgctc gctcgggtgt cgggtcagat cgatccagtt ggcgcacgta ataatccttt | 60 |
| tccccagaag gagtcgaacc cctcctcccc gtccaatcca atcaaagcga ccaatcgact | 120 |
| ggctgtccta cacacacaca aaaccgaccg aggcgacaca ccgcagcagt gatcattctg | 180 |
| agcatttgca gaaaaaggag aacgtcccga atcctggtg gttgtattgt gtgattgctc | 240 |
| actcagtccg tgcagggtca gggtgaagcc aagccaacaa cccaacgctc gctgggagta | 300 |
| gggtccaccg gatttattgg cagtacatcg ctgtttggtc ctcctgccct tcgcttattt | 360 |
| tttaattcgg cagacgtgca cagacagggc accaccggac caaggaaggg cgcacaccgt | 420 |
| cgtcagtcac caggtgggtg tgatcagcag ccgcttctct tgtgctgctt tatagcgtat | 480 |
| gaaattccag tgtccctgtt ccacctgcat gcaattggtt tgactgaaca acatgatagc | 540 |
| aagtgatact atatatattt ttatagagga acacagtgaa aaaatattta gtattattac | 600 |
| gtgcatgaaa ttgtattcac agttatccct gatgcaacgc aattgttcaa tatatagcag | 660 |
| tatatattat acgaagtata tatgtatatc taattttatg agaccgggag aaggtgtatt | 720 |
| cacagtacag tgcagggcca tggccatgca gcccttgggg cctgaaaagg gtcgcgtgaa | 780 |
| gtggccaacg ctgtgcaatt gcaaccaaac aaacttttgg tggcgggtc cctgtccctg | 840 |
| gccggctttg cccacaggcc acagcgcatc acaccaccgc tttatagcgc caccccacca | 900 |
| ccctcgtctc tcccccccgtc gagcacacaa cacaccctcc tcgtcctcca atccaatcaa | 960 |
| cctggtagac tcgcttcgct tctcccccca gctcggacgg agctcctcgc agcagccgcc | 1020 |
| gatcaacctg cgctcgggct cagcgctgga aggtgagagc tcagtgcctc gtcccgcccg | 1080 |
| ccccaaatct ggttcttgtg ctggctctgg ctgtgcgctg cacgaattct gcatctggtt | 1140 |
| ctttcgagac gcaattcccg gaccgtgggc tttggtttcg gaggggccg agagtaaggc | 1200 |
| gttaggactt tctccgagct gcaaggccgc tcgtcgttgc ggcattttc gtttcgcttg | 1260 |

| | |
|---|---|
| tcctgtgatg agagatgtgc atttcccttt ggcgggctta ccgttccctg ctcgtctgta | 1320 |
| tgtgtgtatg tttgtgtgac cttttccctca acgccaggct cttctcccct cttgctgttt | 1380 |
| cttttcagcag tacagacgcg catctgtaca gcgcctttct tcggtcctgg gttatgattg | 1440 |
| atccgttaac agttggtcac caagtgctgg ctgtttaata tgtactataa gcttcttggt | 1500 |
| gccgctgcct ctgcctatac gactttatgc gctgcctgca caagtctcag ccatctgtgg | 1560 |
| gaacgtgtgt ctctcaccta cctttcatat tgcactagct ggattgaatc attctgcttt | 1620 |
| ggagagatgt ccggtcattt ttttttaaat cattttcatc tcgcgtacta gttttttgttt | 1680 |
| tgttttgcga gagagtaatt ttttttaat atttactgtc tcctgtccca tttgctgttt | 1740 |
| ctttacccag aaatttccac cagattcagt caaacgaaac tcctgtgctc ttttttttct | 1800 |
| ccctttcaaa agggtgtgta accgactacc gactcagata atataagtgc ggtcacatat | 1860 |
| cacatgatat catctcgcct ctctcccttc tcctgtgttt tattttcctt ttttctaacc | 1920 |
| acagcgtgat gaacttcttt tttttttggg ggggggggg gggtaacta cagcttagcg | 1980 |
| aacatgaatg ggtagtttta caactaatgc aacggctggt tcactgaaca actgtaggtg | 2040 |
| ttggaagaga atagcctgaa ggttcacagt aaccttcatc tgtcggaagc c | 2091 |

<210> SEQ ID NO 49
<211> LENGTH: 1106
<212> TYPE: DNA
<213> ORGANISM: Zea mays

<400> SEQUENCE: 49

| | |
|---|---|
| atccacgctc gctcgggtgt cgggtcagat cgatccagtt ggcgcacgta ataatccttt | 60 |
| tccccagaag gagtcgaacc cctcctcccc gtccaatcca atcaaagcga ccaatcgact | 120 |
| ggctgtccta cacacacaca aaaccgaccg aggcgacaca ccgcagcagt gatcattctg | 180 |
| agcatttgca gaaaaggag aacgtcccga aatcctggtg gttgtattgt gtgattgctc | 240 |
| actcagtccg tgcagggtca gggtgaagcc aagccaacaa cccaacgctc gctgggagta | 300 |
| gggtccaccg gatttattgg cagtacatcg ctgtttggtc ctcctgccct tcgcttattt | 360 |
| tttaattcgg cagacgtgca cagacagggc accaccggac caaggaaggg cgcacaccgt | 420 |
| cgtcagtcac caggtgggtg tgatcagcag ccgcttctct tgtgctgctt tatagcgtat | 480 |
| gaaattccag tgtccctgtt ccacctgcat gcaattggtt tgactgaaca acatgatagc | 540 |
| aagtgatact atatatattt ttatagagga acacagtgaa aaaatattta gtattattac | 600 |
| gtgcatgaaa ttgtattcac agttatccct gatgcaacgc aattgttcaa tatatagcag | 660 |
| tatatattat acgaagtata tatgtatatc taatttatg agaccgggag aaggtgtatt | 720 |
| cacagtacag tgcagggcca tggccatgca gcccttgggg cctgaaaagg gtcgcgtgaa | 780 |
| gtggccaacg ctgtgcaatt gcaaccaaac aaacttttgg tggcggggtc cctgtccctg | 840 |
| gccggctttg cccacaggcc acagcgcatc acaccaccgc tttatagcgc cacccacca | 900 |
| ccctcgtctc tccccccgtc gagcacacaa cacaccctcc tcgtcctcca atccaatcaa | 960 |
| cctggtagac tcgcttcgct tctcccccca gctcggacgg agctcctcgc agcagccgcc | 1020 |
| gatcaacctg cgctcgggct cagcgctgga aggtgttgga agagaatagc ctgaaggttc | 1080 |
| acagtaacct tcatctgtcg gaagcc | 1106 |

<210> SEQ ID NO 50
<211> LENGTH: 1597
<212> TYPE: DNA
<213> ORGANISM: Zea mays

<400> SEQUENCE: 50

```
gatccacgct cgctcgggtg tcgggtcaga tcgatccagt tggcgcacgt aataatcctt      60
ttccccagaa ggagtcgaac ccctcctccc cgtccaatcc aatcaaagcg accaatcgac     120
tggctgtcct acacacacac aaaaccgacc gaggcgacac accgcagcag tgatcattct     180
gagcatttgc agaaaaagga aacgtcccg aaatcctggt ggttgtattg tgtgattgct      240
cactcagtcc gtgcagggtc agggtgaagc caagccaaca acccaacgct cgctgggagt     300
agggtccacc ggatttattg gcagtacatc gctgtttggt cctcctgccc ttcgcttatt     360
ttttaattcg gcagacgtgc acagacaggg caccaccgga ccaaggaagg cgcacaccg      420
tcgtcagtca ccaggtgggt gtgatcagca gccgcttctc ttgtgctgct ttatagcgta     480
tgaaattcca gtgtccctgt tccacctgca tgcaattggt tgactgaac  aacatgatag     540
caagtgatac tatatatatt tttatagagg aacacagtga aaaaatattt agtattatta     600
cgtgcatgaa attgtattca cagttatccc tgatgcaacg caattgttca atatatagca     660
gtatatatta tacgaagtat atatgtatat ctaattttat gagaccggga aaggtgtat     720
tcacagtaca gtgcagggcc atggccatgc agcccttggg gcctgaaaag ggtcgcgtga    780
agtggccaac gctgtgcaat tgcaaccaaa caaactttg gtggcggggt ccctgtccct     840
ggccggcttt gcccacaggc cacagcgcat cacaccaccg ctttatagcg ccaccccacc     900
accctcgtct ctcccccgt cgagcacaca acacaccctc ctcgtcctcc aatccaatca     960
acctggtaga ctcgcttcgc ttctccccc agctcggacg gagctcctcg cagcagccgc    1020
cgatcaacct gcgctcgggc tcagcgctgg aaggtgttgg aagagaatag cctgaaggtt    1080
cacagtaacc ttcatctgtc ggaagccctc cgccgccgcc ggtaaccacc ccgcccctct    1140
cctctttctt tctccgtttt tttttccgtc tcggtctcga tctttggcct tggtagtttg    1200
ggtgggcgag aggcggcttc gtgcgcgccc agatcggtgc gcgggagggg cgggatctcg    1260
cggctggggc tctcgccggc gtggatccgg cccggatctc gcggggaatg gggctctcgg    1320
atgtagatct gcgatccgcc gttgttgggg gagatgatgg ggggtttaaa atttccgccg    1380
tgctaaacaa gatcaggaag aggggaaaag ggcactatgg tttatatttt tatatatttc    1440
tgctgcttcg tcaggcttag atgtgctaga tctttctttc ttcttttttgt gggtagaatt    1500
tgaatccctc agcattgttc atcggtagtt tttcttttca tgatttgtga caaatgcagc    1560
ctcgtgcgga gcttttttgt aggtagaagt gatcaac                             1597
```

<210> SEQ ID NO 51
<211> LENGTH: 907
<212> TYPE: DNA
<213> ORGANISM: Zea mays

<400> SEQUENCE: 51

```
atccacgctc gctcgggtgt cgggtcagat cgatccagtt ggcgcacgta ataatccttt      60
tccccagaag gagtcgaacc cctcctcccc gtccaatcca atcaaagcga ccaatcgact     120
ggctgtccta cacacacaca aaaccgaccg aggcgacaca ccgcagcagt gatcattctg     180
agcatttgca gaaaaaggag aacgtcccga aatcctggtg gttgtattgt gtgattgctc     240
actcagtccg tgcagggtca gggtgaagcc aagccaacaa cccaacgctc gctgggagta    300
gggtccaccg gatttattgg cagtacatcg ctgtttggtc ctcctgccct tcgcttattt     360
tttaattcgg cagacgtgca cagacagggc accaccggac caaggaaggg cgcacaccgt     420
cgtcagtcac caggtgggtg tgatcagcag ccgcttctct tgtgctgctt tatagcgtat     480
```

```
gaaattccag tgtccctgtt ccacctgcat gcaattggtt tgactgaaca acatgatagc      540
aagtgatact atatatattt ttatagagga acacagtgaa aaaatattta gtattattac      600
gtgcatgaaa ttgtattcac agttatccct gatgcaacgc aattgttcaa tatatagcag      660
tatatattat acgaagtata tatgtatatc taatttatg agaccgggag aaggtgtatt       720
cacagtacag tgcagggcca tggccatgca gcccttgggg cctgaaaagg gtcgcgtgaa      780
gtggccaacg ctgtgcaatt gcaaccaaac aaacttttgg tggcggggtc cctgtccctg      840
gccggctttg cccacaggcc acagcgcatc acaccaccgc tttatagcgc caccccacca      900
ccctcgt                                                                907

<210> SEQ ID NO 52
<211> LENGTH: 1039
<212> TYPE: DNA
<213> ORGANISM: Zea mays

<400> SEQUENCE: 52
gtgagagctc agtgcctcgt cccgcccgcc ccaaatctgg ttcttgtgct ggctctggct       60
gtgcgctgca cgaattctgc atctggttct ttcgagacgc aattcccgga ccgtgggctt      120
tggtttcgga gggggccgag agtaaggcgt taggactttc tccgagctgc aaggccgctc      180
gtcgttgcgg cattttcgt ttcgcttgtc ctgtgatgag agatgtgcat ttcccttgg        240 cgggcttacc gttccctgct cgtctgtatg tgtgtatgtt tgtgtgacct ttccctcaac      300
gccaggctct ctcccctct tgctgttct ttcagcagta cagacgcgca tctgtacagc        360 gccttttcttc ggtcctgggt tatgattgat ccgttaacag ttggtcacca agtgctggct    420
gtttaatatg tactataagc ttcttggtgc cgctgcctct gcctatacga ctttatgcgc      480
tgcctgcaca agtctcagcc atctgtggga acgtgtgtct ctcacctacc tttcatattg      540
cactagctgg attgaatcat tctgctttgg agagatgtcc ggtcatttt ttttaaatca       600 ttttcatctc gcgtactagt ttttgttttg ttttgcgaga gagtaatttt tttttaatat      660
ttactgtctc ctgtcccatt tgctgtttct tacccagaa atttccacca gattcagtca       720
aacgaaactc ctgtgctctt ttttttctcc ctttcaaaag ggtgtgtaac cgactaccga      780
ctcagataat ataagtgcgg tcacatatca catgatatca tctcgcctct ctcccttctc      840 ctgtgttta ttttccttt ttctaaccac agcgtgatga acttctttt tttttggggg         900 ggggggggg ggtaactaca gcttagcgaa catgaatggg tagtttaca actaatgcaa        960 cggctggttc actgaacaac tgtaggtgtt ggaagagaat agcctgaagg ttcacagtaa     1020
ccttcatctg tcggaagcc                                                  1039

<210> SEQ ID NO 53
<211> LENGTH: 3530
<212> TYPE: DNA
<213> ORGANISM: Oryza sativa

<400> SEQUENCE: 53
ggcttcccgc tgtgagagaa gtggctgcct ctcggttctc accaagcagt cgaaaatgcc       60
agaacagcga ccagatagga tcatcgtgcc atgcaggcat gcagcctttg agaactgaaa      120
gagccggtga aagtcctgca aagcgaaaag caaatgaaca acatctgcc tgtgctgctg       180 cctcgcctcg ctgtccttttt ccggtgggtt gccgctgcta acctctgcct ccgcgatacg     240
tgacacgtca tcctccccc accccacccc atgcttgcac cccccccccc ccccctccct      300
cccttattac caccaccccc ctcctccatc ctcctctgct cctccaacct ggctcagttt      360
```

-continued

```
cctcctgttc ttgagagaac tgaatctgct gtccagctgc tgctccggct ggtctctgag    420
ttgaaggtaa ggttaatcgg tgtctctcag cctgaatgaa tttgtctatc tcctatggct    480
ttgtggtggt tgaattttgc gttctgggga tgttaggacc ttcttgttgg acaatttct    540 gagattctgg cttgctttgg atgggttggg ggaagagtta ggtgcttgct ggtgtgtatt    600
tcttttgcat ttcggttgtc ctgtgaagga tgcgtgttct cggcatttcc agctcattgt    660
gtctttgccc ttcagataac agttatcctc gtgcttttcc ttttcttc agcaaaacat    720 atctggactt ctgtacaagt gcttttttt tcttctttgg acgatatttt gttttgcatt    780
ctagtgattc tgtacaagtg ccatctgata gcatatcatc attcggcaac tggtgatttc    840
ccctatgcgg tctttcatgt acttgcatga ttgaacatat ggcagtgctt ctgtcggatg    900
ctatcgatgt tttacttgcg aaaggccggg aacttttg cagatcttga ggttttagt    960 agtgatgcag tcattcaaaa agataacctt gtgctggtcc ttttgccttt cggctgcact   1020
tgcatgtgcg ttttctcaga gatgctgcat ctccagctca gcttctgtca tcagtcatta   1080
gtcattgcca tcttttatgt ggataaagtc aaagttaatt tagcaccgct gttttggagt   1140
tgtttggtca ttttatatat tttcatcagg tgttgtttac tgttcctggt actaaaattt   1200
cgaatttaca aatgactacc tcattctcct ttctttttt ccttttcct tgtggcagac   1260 cggttcctga agaatattc ttttcatgaa atgtacttcc ggtttttaa atagaatgat   1320 taaattacag taggatgaat aactaaattt gtcgatatgc cttgtaccgg tactccttgt   1380
tagttcttag tgaatctatg tatactattg cttgtcaaat tgtgaatttt actatcagct   1440
gtatgtatgt ctattgaaga actctcaaca gttctaactt cctaagatgt tttaatcaat   1500
tcttgctacc aacctggata cagtattctc cgtagttttt tcttcatttt ttttttaaag   1560
agatctattg agagtccttg gtacccatct tctgtagaat tgtccatgtg aacagttgct   1620
tcaagatttc tgctgcatct gtgatacggt atcactgata ctgtagtgat cagatccaaa   1680
acacatatat agttcgccac cattctaaaa cacatgtttg tgtgatcaga tctagctcgc   1740
caccatatat agttcaggtt ttcaagttgt aatatcactt gccttttgcg atagatatga   1800
caacacactt tgtgtcaggc tgtcccaatt ttctctgaat tttctctcat atatcatgat   1860
ttagttatgg cttttgttcc ttgacatttc aatgtctaat tgtccaatgt taagtaaatc   1920
cttttcatag cctgatttat tgaatacttg caggtacttg ataacttga aggttcctag   1980 gaaccttcat ttgttggaag atgtataggg ctaagagggc tgcattatct ccaaaggtga   2040
agcgccgtgt agggaagtat gagctcgggc gcaccattgg agaaggaacc tttgcaaagg   2100
tccggtttgc gaagaacact gaaaatgacg aaccagttgc tatcaaaatc cttgacaagg   2160
agaaggttca gaagcacaga ttggttgaac agattaggcg tgaaatttgt actatgaagt   2220
tagtaaagca tcctaatgtt gttcggctgt tcgaggtcat gggaagtaaa gcaagaattt   2280
tcattgttct ggaatatgtt actggaggag agctctttga aatcattgca actaatggaa   2340
ggttgaagga ggaggaagca cgaaaatact ttcaacaact tatcaatgca gttgactact   2400
gccacagtag gggtgtgtac cacagagact tgaagttaga aaatttgctg cttgatgctt   2460
ctggaaacct gaaagtatct gactttggtt tgagtgcttt aaccgagcaa gtgaaggctg   2520
acggtttgct gcacacgaca tgtggaactc ctaattatgt tgctccagag gtgattgagg   2580
acagaggcta tgatggggca gctgcagata tctggtcttg tggggtaatc ctttatgttc   2640
tgcttgctgg gttttttacca tttgaggatg acaacatcat tgctctttat aaaaagatct   2700
ctgaagctca gtttacctgt ccctcttggt tttctactgg agctaagaag ctgatcacca   2760
```

| | | | | |
|---|---|---|---|---|
| gaattctgga | tcccaaccct | acaactagga | tcaccatttc | tcaaatactg gaagatcctt | 2820 |
| ggttcaaaaa | gggttacaaa | ccgcctgtat | ttgacgagaa | atatgaaact agttttgacg | 2880 |
| atgtcgatgc | tgcttttgga | gactccgaag | accggcatgt | caaagaagaa actgaagatc | 2940 |
| agcctacctc | tatgaacgcg | tttgaactca | tttcactgaa | tcaggcactg aatctggaca | 3000 |
| atttgttcga | ggcaaaaaag | gagtataaaa | gagagacaag | attcacatca caatgtcctc | 3060 |
| caaaagaaat | tatcaccaag | attgaagaag | ctgcaaagcc | acttggattt gatattcaaa | 3120 |
| agaaaaatta | caagatgcgc | atggagaacc | tgaaagcagg | tagaaaaggc aatctcaatg | 3180 |
| ttgcaactga | ggttttccaa | gtagctccat | ccttacatgt | ggttgagctc aagaaggcaa | 3240 |
| aggggggacac | tctggagttc | caaaaggtgc | cattctttga | caccggaaat tcgctatttt | 3300 |
| ccaacttgct | atttactgcc | aagtttaacc | aaaatcaatt | ctgctgtgaa caacagttc | 3360 |
| tacagaaccc | tgtcgaccca | gctcaaggac | gtggtctgga | agtgcgacgg cgaggtcgaa | 3420 |
| ggcaacggcg | ccgcggcgtg | aacgtggttt | tgccatggc | tttcggggca ccggttcttc | 3480 |
| gtgtacatag | ctgctctgcc | atcatcaatg | gggtgttcgc | cgtagagtag | 3530 |

<210> SEQ ID NO 54
<211> LENGTH: 769
<212> TYPE: DNA
<213> ORGANISM: Rice tungro bacilliform virus

<400> SEQUENCE: 54

| | | | | |
|---|---|---|---|---|
| gatctcctac | aaaagggagt | agtaatattt | aatgagcttg | aaggaggata tcaactctct | 60 |
| ccaaggttta | ttggagacct | ttatgctcat | ggttttatta | aacaaataaa cttcacaacc | 120 |
| aaggttcctg | aagggctacc | gccaatcata | gcggaaaaac | ttcaagacta taagttccct | 180 |
| ggatcaaata | ccgtcttaat | agaacgagag | attcctcgct | ggaacttcaa tgaaatgaaa | 240 |
| agagaaacac | agatgaggac | caacttatat | atcttcaaga | attatcgctg tttctatggc | 300 |
| tattcaccat | taaggccata | cgaacctata | actcctgaag | aatttgggtt tgattactac | 360 |
| agttgggaaa | atatggttga | tgaagacgaa | ggagaagttg | tatacatctc caagtatact | 420 |
| aagattatca | aagtcactaa | agagcatgca | tgggcttggc | cagaacatga tggagacaca | 480 |
| atgtcctgca | ccacatcaat | agaagatgaa | tggatccatc | gtatggacaa tgcttaaaga | 540 |
| agctttatca | aaagcaactt | taagtacgaa | tcaataaaga | aggaccagaa gatataaagc | 600 |
| gggaacatct | tcacatgcta | ccacatggct | agcatcttta | ctttagcatc tctattattg | 660 |
| taagagtgta | taatgaccag | tgtgcccctg | gactccagta | tataaggagc accagagtag | 720 |
| tgtaatagat | catcgatcaa | gcaagcgaga | cgtcaaactt | ctaagagag | 769 |

<210> SEQ ID NO 55
<211> LENGTH: 697
<212> TYPE: DNA
<213> ORGANISM: Zea mays

<400> SEQUENCE: 55

| | | | | |
|---|---|---|---|---|
| cggcccgggc | tggtaaatat | cggaatatta | gcatgtcaac | ttgcactctc taaggctcct | 60 |
| ttggaaagca | ggatttaga | aaaaaaatc | atataaattt | tttacatgaa tcagtttatt | 120 |
| ttcggattat | gaaatatttt | ctcataacag | tataacacat | attttgtata taagttatta | 180 |
| tgttattata | tataaccgtt | gcaacgtacg | ggcattcacc | tagtaaagaa agaagattaa | 240 |
| ttattctctg | gtggagattg | tgcccgagcc | cgaaggtcat | gatatggacg ttgcaaaccc | 300 |
| acttcacgag | gggacaaaaa | agaaataggg | ttaccacttt | catcagttaa agggcgtgac | 360 |

-continued

| | |
|---|---|
| atggacgtgt tgaagatccg gcacattccc tgcgaaatat acacgtcatg gtactaacga | 420 |
| ggcatgaaac tggccacatg gccatggacg cgtgaagcgt gccatgcatt ggacatgcgg | 480 |
| catccgaact tctgaagatc atatcagaga gacactgatg tacgaactgc cgtaacattc | 540 |
| tattctatat atacccctcag tccctgttcc agttctcgtt aagctagcag caccaagttg | 600 |
| tcgaacactt gcctgctctt gagctcgatc aagctatcat cagctgcgtc ttgcgcacag | 660 |
| caacagcttc ccaactgcaa ccgtagcagc cagatct | 697 |

<210> SEQ ID NO 56
<211> LENGTH: 1455
<212> TYPE: DNA
<213> ORGANISM: Coix lacryma-jobi

<400> SEQUENCE: 56

| | |
|---|---|
| cggtacctcg cgaatgcatc tagatcccct ttccgcgggc aattcgatag gtagaaatcc | 60 |
| gccgggttga taccccctgca atcgtagcgt gatgagggtg tgaatgttgc cgatgtgtgg | 120 |
| acttcgagga aaatgatagc ccctggaatg ccgagatagc cgaagtcgag gtggtcgtgg | 180 |
| tcgggagaca cgcagcagta gcctattctt tggtaggggt cgatgttcaa gcgtcaacga | 240 |
| tcggctgggc gacataaaaa ttagcaccag ggtgaccttc ttgcttcttc gatcgtctgg | 300 |
| acgtcgagga gccccgcggc agcgcacgcg tctgcaccgt tatggtggcc gcgctcgcga | 360 |
| tggaatagaa ggggtaatga tggatccggc caggaaggcc acgacatcga cggatccaac | 420 |
| cggcaagacg cgatccggt taaatagacg acggatctag ctgggaaggt agactctata | 480 |
| ttaaatgagg ttgtacatgc cctaataact ttataaatct aatttattca gaggcaaggt | 540 |
| agtagtatta tctttcccaa cggatagtta tctgatctgc cgttcagctt gatcgataac | 600 |
| tttataaatc taatttattc agaggccggc ggcagcgcac acgtctgcac cagtaatgtt | 660 |
| agccgcgcct gtggcgtaat agaagggta acgatggatc cgaccagaaa ggcctcgaca | 720 |
| tcgacggatc cagacggcga tccggtcaaa gagacgacga atctagccga aaggtagat | 780 |
| ctctcgagag agttcatatt aaatgatgtt gtacatgcca taataactct ataaatctaa | 840 |
| tttattcata ggcgaaggta gtagtattat ctttcccagc ggatcgttat ctgatctgcc | 900 |
| gttcagcttg atcgatccac gtcgtttgat ctcggcgagc agcacatggc ggctcttctt | 960 |
| gtgtacaggt ctcactctct gctacttcag tgcaaggcgg agtgaacgca cacaataacg | 1020 |
| tgagtattgt gggaactacc ttgtagatgc aaacgatgta atccacctg ctccaccaag | 1080 |
| tgcccgcccg gctctatcca ttccattcgt caacatgcag gttcaagact ggcccgtgct | 1140 |
| ggaccagtga gcggtgccgg tggaccccaa tgcaagcgaa gcgagtgacc atcggggaag | 1200 |
| cctcccgtgc tgcccccaca tggcttgcct gaatgcctct ctctcgccgc agtgccctct | 1260 |
| ctctctcctc ctcctctccg tcgaagggcg tcacgagagc ccagagggca tccgaggccc | 1320 |
| ccaccccacc ccttcctccc gtgtatataa gcagtggcag ggtgagcgtc tctcctcaga | 1380 |
| ccaccactgc gccattggcc agctagagcc aaccagaaga gcttgcagtt actgagagtg | 1440 |
| tgtgagagag agagg | 1455 |

<210> SEQ ID NO 57
<211> LENGTH: 5365
<212> TYPE: DNA
<213> ORGANISM: Artificial
<220> FEATURE:
<223> OTHER INFORMATION: Synthetic fusion sequence from multiple
    organisms

<400> SEQUENCE: 57

| | |
|---|---|
| aggattttc ggcgctgcgc tacgtccgcg accgcgttga gggatcaagc cacagcagcc | 60 |
| cactcgacct tctagccgac ccagacgagc caagggatct ttttggaatg ctgctccgtc | 120 |
| gtcaggcttt ccgacgtttg ggtggttgaa cagaagtcat tatcgcacgg aatgccaagc | 180 |
| actcccgagg ggaaccctgt ggttggcatg cacatacaaa tggacgaacg gataaacctt | 240 |
| ttcacgccct tttaaatatc cgattattct aataaacgct cttttctctt aggtttaccc | 300 |
| gccaatatat cctgtcaaac actgatagtt taaactgaag gcgggaaacg acaatctgat | 360 |
| ccccatcaag ctagcttctg caggtcctgc tcgaggtcat tcatatgctt gagaagagag | 420 |
| tcgggatagt ccaaaataaa acaaaggtaa gattacctgg tcaaaagtga aaacatcagt | 480 |
| taaaaggtgg tataaagtaa aatatcggta ataaaaggtg gcccaaagtg aaatttactc | 540 |
| ttttctacta ttataaaaat tgaggatgtt tttgtcggta ctttgatacg tcattttgt | 600 |
| atgaattggt ttttaagttt attcgctttt ggaaatgcat atctgtattt gagtcgggtt | 660 |
| ttaagttcgt ttgcttttgt aaatacagag ggatttgtat aagaaatatc tttaaaaaaa | 720 |
| cccatatgct aatttgacat aattttgag aaaaatatat attcaggcga attctcacaa | 780 |
| tgaacaataa taagattaaa atagcttcc cccgttgcag cgcatgggta tttttttctag | 840 |
| taaaaataaa agataaactt agactcaaaa catttacaaa acaaccccct aaagtcctaa | 900 |
| agcccaaagt gctatccacg atccatagca agcccagccc aacccaaccc aacccaaccc | 960 |
| accccagtcc agccaactgg acaatagtct ccacacccc ccactatcac cgtgagttgt | 1020 |
| ccgcacgcac cgcacgtctc gcagccaaaa aaaaaaaaag aaagaaaaaa aagaaaaaga | 1080 |
| aaaacagca ggtgggtccg ggtcgtgggg gccggaaacg cgaggaggat cgcgagccag | 1140 |
| cgacgaggcc ggccctccct ccgcttccaa agaaacgccc cccatcgcca ctatatacat | 1200 |
| acccccccct ctcctcccat ccccccaacc ctaccaccac caccaccacc acctcctccc | 1260 |
| ccctcgctgc cggacgacga gctcctcccc cctcccccctc cgccgccgcc ggtaaccacc | 1320 |
| ccgcccctct cctctttctt tctccgttt ttttttccgt ctcggtctcg atctttggcc | 1380 |
| ttggtagttt gggtgggcga gaggcggctt cgtgcgcgcc cagatcggtg cgcgggaggg | 1440 |
| gcgggatctc gcggctgggg ctctcgccgg cgtggatccg gcccggatct cgcggggaat | 1500 |
| ggggctctcg gatgtagatc tgcgatccgc cgttgttggg ggagatgatg gggggttaa | 1560 |
| aatttccgcc atgctaaaca agatcaggaa gagggaaaa gggcactatg gtttatattt | 1620 |
| ttatatattt ctgctgcttc gtcaggctta gatgtgctag atctttcttt cttcttttg | 1680 |
| tgggtagaat ttgaatccct cagcattgtt catcggtagt ttttcttttc atgatttgtg | 1740 |
| acaaatgcag cctcgtgcgg agctttttg taggtagacc atggtccct acgcgactgc | 1800 |
| ggcggaggcg gagggagcac tggggcgcac catgacgtgg gctgagacag catggtacga | 1860 |
| gtactcggcg gtgatgccag attcctggct gcactgccac accacattta tcctgttcgt | 1920 |
| catctacagc atcgcccgc tgcccctgct actcctagag cagttcgctc cgtccgtcgt | 1980 |
| gctgccgtac aagctgcagc ccgggtacg gctgccccg gcagcctccc tcagctgcta | 2040 |
| catgacgcg gcctgcatct ttccgctcgc cgttggcctt cagttcgtct cctatcctgc | 2100 |
| ggtcgccaag atactaagga cccgaatggg actgccgttg ccgtcggtga gggagaccat | 2160 |
| cgcgcagcta gtcgtatact ctctagtgga ggattacctc agctactgga tgcaccgtct | 2220 |
| gctgcacacc cagtggtgct acgagaagat ccaccgcgtc caccacgagt tcacggctcc | 2280 |
| tacaggcttc gccatgtcgt acagccactg ggccgagaac gtcgtccttt ctatcccggc | 2340 |
| cttggccggc ccagtgctcg tgccatgcca tgtcaccacg cagtggctat ggttctccat | 2400 |

```
ccgcctaatt gagggcatta acacgcacag cggttaccat ttcccgttca gcccttgcag    2460
gctgattcca ttctacggag gggctgcata ccatgactac catcactatg caggaggccg    2520
tagccaaagc aactttgcac ccctgttcac ctactgtgat tatttatata ggacagacaa    2580
aggctacaga taccacaagc taaagcaaga gaagctgaag agtctagcag aaaatagtgc    2640
ggataaagga ggcaactact cattcgacga agggaaaaag aacagatatt tttgtgcctg    2700
agcgtacgaa gaataatcaa ggctattact tcgtcctgtt cgaagggccc ggggatcca    2760 ctagttctag ctatatcatc aatttatgta ttacacataa tatcgcactc agtctttcat    2820
ctacggcaat gtaccagctg atataatcag ttattgaaat atttctgaat ttaaacttgc    2880
atcaataaat ttatgttttt gcttggacta taatacctga cttgttattt tatcaataaa    2940
tatttaaact atatttcttt caagatatca ttctttacaa gtatacgtgt ttaaattgaa    3000
taccataaat ttttattttt caaatacatg taaaattatg aaatgggagt ggtggcgacc    3060
gagctcaagc acacttcaat tcctataacg gaccaaatcg caaaaattat aataacatat    3120
tatttcatcc tggattaaaa gaaagtcacc ggggattatt ttgtgacgcc gattacatac    3180
ggcgacaata aagacattgg aaatcgtagt acatattgga atacactgat tatattaatg    3240
atgaatacat actttaatat ccttacgtag gatcgatccg aattcgcgac acgcggccgc    3300
tctagaacta gtggatcccc cccttaatta aggggggctgc aggaattcat aacttcgtat    3360
aatgtatgct atacgaagtt atagcttggt cgagtggaag ctagcttttcc gatcctacct    3420 gtcacttcat caaaggaca gtagaaaagg aaggtggcac ctacaaatgc catcattgcg    3480
ataaaggaaa ggctatcatt caagatgcct ctgccgacag tggtcccaaa gatggacccc    3540
cacccacgag gagcatcgtg gaaaaagaag acgttccaac cacgtcttca aagcaagtgg    3600
attgatgtga tacttccact gacgtaaggg atgacgcaca atcccactat ccttcgcaag    3660
acccttcctc tatataagga agttcatttc atttggagag gacacgctga atcaccagt    3720 ctctctctac aagatcgggg atctctagct agacgatcgt ttcgcatgat tgaacaagat    3780
ggattgcacg caggttctcc ggccgcttgg gtggagaggc tattcggcta tgactgggca    3840
caacagacaa tcggctgctc tgatgccgcc gtgttccggc tgtcagcgca ggggcgcccg    3900
gttctttttg tcaagaccga cctgtccggt gccctgaatg aactgcagga cgaggcagcg    3960
cggctatcgt ggctggccac gacgggcgtt ccttgcgcag ctgtgctcga cgttgtcact    4020
gaagcgggaa gggactggct gctattgggc gaagtgccgg gcaggatct cctgtcatct    4080 caccttgctc ctgccgagaa agtatccatc atggctgatg caatgcggcg gctgcatacg    4140
cttgatccgg ctacctgccc attcgaccac caagcgaaac atcgcatcga gcgagcacgt    4200
actcggatgg aagccggtct tgtcgatcag gatgatctgg acgaagagca tcagggctc    4260 gcgccagccg aactgttcgc caggctcaag gcgcgcatgc ccgacggcga ggatctcgtc    4320
gtgacgcatg gcgatgcctg cttgccgaat atcatggtgg aaaatggccg cttttctgga    4380
ttcatcgact gtggccggct gggtgtggcg gaccgctatc aggacatagc gttggctacc    4440
cgtgatattg ctgaagagct tggcggcgaa tgggctgacc gcttcctcgt gctttacggt    4500
atcgccgctc ccgattcgca gcgcatcgcc ttctatcgcc ttcttgacga gttcttctga    4560
gcgggactct ggggttcgat ccccaattcc cgatcgttca acatttggc aataaagttt    4620 cttaagattg aatcctgttg ccggtcttgc gatgattatc atataatttc tgttgaatta    4680
cgttaagcat gtaataatta acatgtaatg catgacgtta tttatgagat gggttttat    4740 gattagagtc ccgcaattat acatttaata cgcgatagaa aacaaaatat agcgcgcaaa    4800
```

```
ctaggataaa ttatcgcgcg cggtgtcatc tatgttacta gatcggggat cgggccactc    4860
gaccaagcta taacttcgta taatgtatgc tatacgaagt tatcgcgcca aatcgtgaag    4920
tttctcatct aagcccccat ttggacgtga atgtagacac gtcgaaataa agatttccga    4980
attagaataa tttgtttatt gctttcgcct ataaatacga cggatcgtaa tttgtcgttt    5040
tatcaaaatg tactttcatt ttataataac gctgcggaca tctacatttt tgaattgaaa    5100
aaaaattggt aattactctt tcttttctc catattgacc atcatactca ttgctgatcc    5160
atgtagattt cccggacatg aagccattta caattgaata tatcctgccg ccgctgccgc    5220
tttgcacccg gtggagcttg catgttggtt tctacgcaga actgagccgg ttaggcagat    5280
aatttccatt gagaactgag ccatgtgcac cttcccccca acacggtgag cgacggggca    5340
acggagtgat ccacatggga ctttt                                         5365
```